US011814437B2

(12) United States Patent
Satijn et al.

(10) Patent No.: US 11,814,437 B2
(45) Date of Patent: Nov. 14, 2023

(54) ANTIBODIES BINDING TO CD30 AND CD3

(71) Applicant: GENMAB A/S, Valby (DK)

(72) Inventors: David Satijn, Utrecht (NL); Patrick Engelberts, Amersffoort (NL); Kristel Kemper, Utrecht (NL); Esther C. W. Breij, Driebergen (NL); Simone Oostindie, Utrecht (NL); Farshid Alemdehy, Utrecht (NL)

(73) Assignee: GENMAB A/S, Valby (DK)

( * ) Notice: Subject to any disclaimer, the term of this patent is extended or adjusted under 35 U.S.C. 154(b) by 0 days.

(21) Appl. No.: 17/938,523

(22) Filed: Oct. 6, 2022

(65) Prior Publication Data

US 2023/0132049 A1    Apr. 27, 2023

(30) Foreign Application Priority Data

Oct. 8, 2021 (EP) .................................... 21201712

(51) Int. Cl.
*C07K 16/28* (2006.01)
*A61P 35/00* (2006.01)
*C12N 15/63* (2006.01)

(52) U.S. Cl.
CPC .......... *C07K 16/2878* (2013.01); *A61P 35/00* (2018.01); *C07K 16/2809* (2013.01); *C12N 15/63* (2013.01); *C07K 2317/31* (2013.01); *C07K 2317/526* (2013.01); *C07K 2317/565* (2013.01)

(58) Field of Classification Search
CPC ........ C07K 2317/565; C07K 2317/526; C07K 2317/31; C07K 16/2809; C07K 16/2878; C12N 15/63; A61P 35/00
See application file for complete search history.

(56) References Cited

U.S. PATENT DOCUMENTS

| 8,257,706 | B2 | 9/2012 | McDonagh et al. |
| 9,150,663 | B2 | 10/2015 | Labrijn et al. |
| 9,212,230 | B2 | 12/2015 | Schuurman et al. |
| 10,344,050 | B2 | 7/2019 | Gramer et al. |
| 10,407,501 | B2 | 9/2019 | Van Den Brink et al. |
| 10,465,006 | B2 | 11/2019 | Van Den Brink et al. |
| 10,590,206 | B2 | 3/2020 | Labrijn et al. |
| 10,597,464 | B2 | 3/2020 | Labrijn et al. |
| 10,906,991 | B2 | 2/2021 | Schuurman et al. |
| 11,485,796 | B2 | 11/2022 | Labrijn et al. |
| 11,492,371 | B2 | 11/2022 | Gramer et al. |
| 11,613,575 | B2 | 3/2023 | Van Den Brink et al. |
| 2010/0105874 | A1 | 4/2010 | Schuurman et al. |
| 2010/0239571 | A1 | 9/2010 | McDonagh et al. |
| 2011/0123440 | A1* | 5/2011 | Hansen ............ C07K 14/70535 424/1.49 |
| 2013/0039913 | A1 | 2/2013 | Labrijn et al. |
| 2014/0303356 | A1 | 10/2014 | Gramer et al. |
| 2015/0337049 | A1 | 11/2015 | Labrijn et al. |
| 2016/0046727 | A1 | 2/2016 | Labrijn et al. |
| 2016/0159930 | A1 | 6/2016 | Schuurman et al. |
| 2016/0168247 | A1 | 6/2016 | Van Den Brink et al. |
| 2016/0333095 | A1 | 11/2016 | Van Den Brink et al. |
| 2017/0073421 | A1 | 3/2017 | Kjaergaard et al. |
| 2017/0233497 | A1 | 8/2017 | Labrijn et al. |
| 2018/0371086 | A1* | 12/2018 | Cihlar .................... G01N 33/53 |
| 2019/0284278 | A1 | 9/2019 | Rademaker et al. |
| 2020/0048304 | A1 | 2/2020 | Gramer et al. |
| 2020/0095330 | A1 | 3/2020 | Medin et al. |
| 2020/0123255 | A1 | 4/2020 | Van Den Brink et al. |
| 2020/0199229 | A1 | 6/2020 | Van Den Brink et al. |
| 2020/0262932 | A1 | 8/2020 | Labrijn et al. |
| 2020/0332022 | A1 | 10/2020 | Labrijn et al. |
| 2021/0009718 | A1 | 1/2021 | Ambrogelly et al. |
| 2021/0163594 | A1 | 6/2021 | Bailey et al. |
| 2023/0227495 | A1 | 7/2023 | Gramer et al. |

FOREIGN PATENT DOCUMENTS

| WO | 03059202 | A2 | 7/2003 | |
| WO | WO-03059282 | A2 * | 7/2003 | ........... A61K 39/395 |
| WO | 2005035584 | A8 | 1/2006 | |
| WO | 2006105062 | A2 | 10/2006 | |
| WO | 2007040653 | A2 | 4/2007 | |
| WO | 2008119567 | A2 | 10/2008 | |
| WO | WO-2011131746 | A2 * | 10/2011 | ............. A61K 38/17 |
| WO | 2014006217 | A1 | 1/2014 | |
| WO | 2016177846 | A1 | 11/2016 | |
| WO | WO-2017009442 | A1 * | 1/2017 | ............. A61P 31/00 |
| WO | 2019025545 | A1 | 2/2019 | |

(Continued)

OTHER PUBLICATIONS

Tsuchiya et al. (Protein Science vol. 25, Issue 4, pp. 815-825. Apr. 2016) (Year: 2016).*
Rabia et al. (Understanding and overcoming trade-offs between antibody affinity, specificity, stability and solubility. Biochem Eng J. Sep. 15, 2018;137:365-374.) (Year: 2018).*
Liu, et al. ("Fc-Engineering for Modulated Effector Functions—Improving Antibodies for Cancer Treatment." Antibodies 2020, 9, 64) (Year: 2020).*
Bowen, M.A. et al., "Structure and Expression of Murine CD30 and Its Role in Cytokine Production," The Journal of Immunology, vol. 156: 442-449 (1996).
Dürkop et al., "Molecular Cloning and Expression of a New Member of the Nerve Growth Factor Receptor Family That Is Characteristic for Hodgkin's Disease," Cell, vol. 68:421-427 (1992).
Frizzera, Glauco, "The distinction of Hodgkin's disease from anaplastic large cell lymphoma," Seminars in Diagnostic Pathology, vol. 9: 291-296 (1992).

(Continued)

*Primary Examiner* — Gyan Chandra
(74) *Attorney, Agent, or Firm* — Nelson Mullins Riley & Scarborough LLP; Jane E. Remillard, Esq.; Christopher L. Frank

(57) ABSTRACT

The invention relates to multispecific antibodies binding to CD3 and CD30. The invention further provides pharmaceutical compositions comprising antibodies of the invention, nucleic acids encoding the antibodies, host cells that produce the antibodies, methods of producing the antibodies and uses of the antibodies, in particular for cancer therapy.

16 Claims, 40 Drawing Sheets

Specification includes a Sequence Listing.

(56) References Cited

FOREIGN PATENT DOCUMENTS

WO 2020068774 A1 4/2020

OTHER PUBLICATIONS

Giacomelli, R. et al., "Serum levels of soluble CD30 are increased in ulcerative colitis (UC) but not in Crohn's disease (CD)," Clin Exp Immunol., vol. 111:532-535 (1998).

Goulet, D.R. et al., "Kinetic mechanism of controlled Fab-arm exchange for the formation of bispecific immunoglobulin G1 antibodies," Journal of Biological Chemistry, vol. 293(2): 651-661 (2017).

Hansen, H.P. et al., "Ectodomain shedding of CD30 is specifically regulated by peptide motifs in its cysteine-rich domains 2 and 5," The FASEB Journal, pp. 1-17 (2004).

Josimovic-Alasevic, O. et al., "Ki-1 (CD30) antigen is released by Ki-I-positive tumor cells in vitro and in vivo I. Partial characterization of soluble Ki-1 antigen and detection of the antigen in cell culture supernatants and in serum by an enzyme-linked immunosorbent assay," Eur J. Immunol., vol. 19: 157-162 (1989).

Klein, C. et al., "Progress in overcoming the chain association issue in bispecific heterodimeric IgG antibodies," Mabs, vol. 6(6): 653-663 (2012).

Nagata, S. et al., "Cell membrane-specific epitopes on CD30: Potentially superior targets for immunotherapy," PNAS, vol. 102: 7946-7951 (2005).

Oldham, R. A. A et al., "T Cells Armed with Nove Anti-CD30/Anti-CD3 Bispecific Antibodies for immunotherapy of CD30+ Magnancies," Molecular Therapy, vol. 27 (Issue 4) p. 387 (2019).

Pohl. C. et al., "CD30-Antigen-Specific Targeting and Activation of T Cells via Murine Bispecific Monoclonal Antibodies Against (CD30 and CD28: Potential Use for the Treatment of Hodgkin's Lymphoma," Int. J. Cancer, vol. 54: 820-827 (1993).

Pro, B. et al., "Five-year results of brentuximab vedotin in patients with relapsed or refractory systemic anaplastic large cell lymphoma," Blood, vol. 130: 2709-2717 (2017).

Rothe, A. et al., "A phase 1 study of the bispecific anti-CD30/CD16A antibody construct AFM13 in patients with relapsed or refractory Hodgkin lymphoma," Blood, vol. 26: 4024-4031 (2015).

Schwartz, C. L. et al., "Development of an alpha-CD30 bispecific antibody immunotherapy for hodgkin lymphoma," HemaSphere, vol. 2: p. 3 abstract (2018).

Shaneback, K. D. et al., "Regulation of murine B cell growth and differentiation by CD30 ligand," Eur. J. Immunol., vol. 25: 2147-2153 (1995).

Shea, Lauren and Mehta-Shah, Neha, "Brentuximab Vedotin in the Treatment of Peripheral T Cell Lymphoma and Cutaneous T Cell Lymphoma," Current Hematologic Malignancy Reports, vol. 15: 9-19 (2020).

Smith, C.A et al., "The TNF Receptor Superfamily of Cellular and Viral Proteins: Activation, Costimulation and death," Cell, vol. 76: 959-962 (1994).

Younes, A. et al., "Results of a Pivotal Phase II Study of Brentuximab Vedotin for Patients With Relapsed or Refractory Hodgkin's Lymphoma," J Clin Oncol., vol. 30 :2183-9 (2012).

U.S. Appl. No. 14/934,956, filed Nov. 6, 2015, Janine Schuurman, U.S. Pat. No. 10,906,991.

U.S. Appl. No. 12/593,759, filed Jan. 6, 2010, Janine Schuurman, U.S. Pat. No. 9,212,230.

U.S. Appl. No. 16/777,053, filed Jan. 30, 2020, Aran Frank Labrijn, US 20200262932.

U.S. Appl. No. 15/414,122, filed Jan. 24, 2017, Aran Frank Labrijn, U.S. Pat. No. 10,597,464.

U.S. Appl. No. 14/830,336, filed Aug. 19, 2015, Aran Frank Labrijn, US 2016-0046727.

U.S. Appl. No. 13/642,253, filed Oct. 24, 2012, Aran Frank Labrijn, U.S. Pat. No. 9,150,663.

U.S. Appl. No. 17/939,736, filed Sep. 7, 2022, Michael Gramer.

U.S. Appl. No. 16/426,647, filed May 30, 2019, Michael Gramer, U.S. Pat. No. 11,492,371.

U.S. Appl. No. 14/353,962, filed Apr. 24, 2014, Michael Gramer, U.S. Pat. No. 10,344,050.

U.S. Appl. No. 17/950,350, filed Sep. 22, 2022, Aran Frank Labrijn.

U.S. Appl. No. 16/783,720, filed Feb. 6, 2020, Aran Frank Labrijn, U.S. Pat. No. 11,485,796.

U.S. Appl. No. 14/760,157, filed Jul. 9, 2015, Aran Frank Labrijn, U.S. Pat. No. 10,590,206.

U.S. Appl. No. 16/582,428, filed Sep. 25, 2019, Edward Van Den Brink, US 20200123255.

U.S. Appl. No. 14/902,757, filed Jan. 4, 2016, Edward Van Den Brink, U.S. Pat. No. 10,465,006.

U.S. Appl. No. 18/109,708, filed Feb. 14, 2023, Edward Norbert Van Den Brink.

U.S. Appl. No. 16/544,376, filed Aug. 19, 2019, Edward Norbert Van Den Brink, US 20200199229.

U.S. Appl. No. 15/110,414, filed Jul. 8, 2016, Edward Norbert Van Den Brink, U.S. Pat. No. 10,407,501.

* cited by examiner

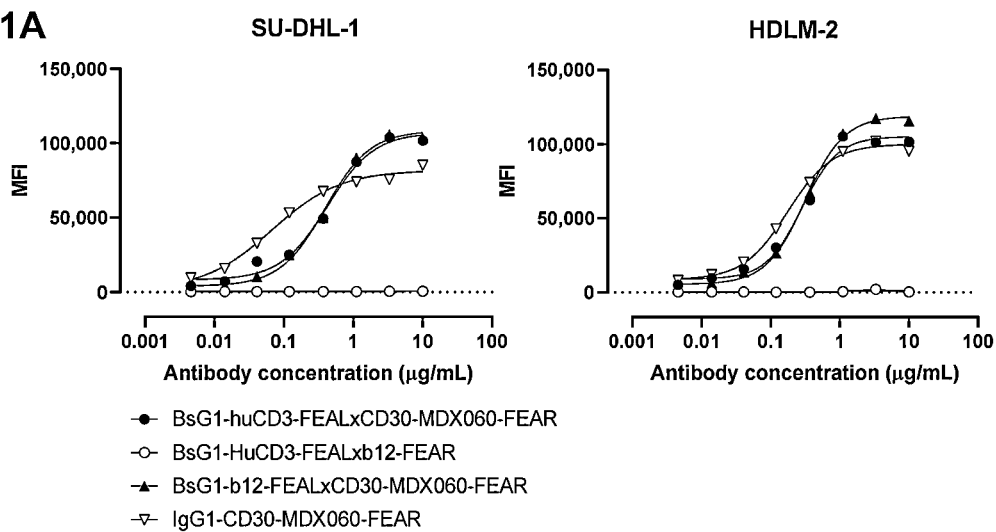
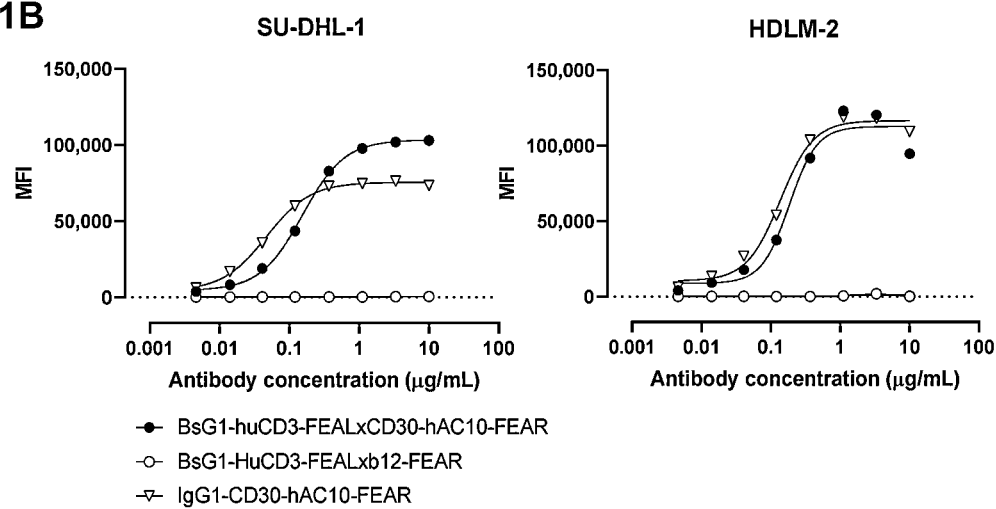
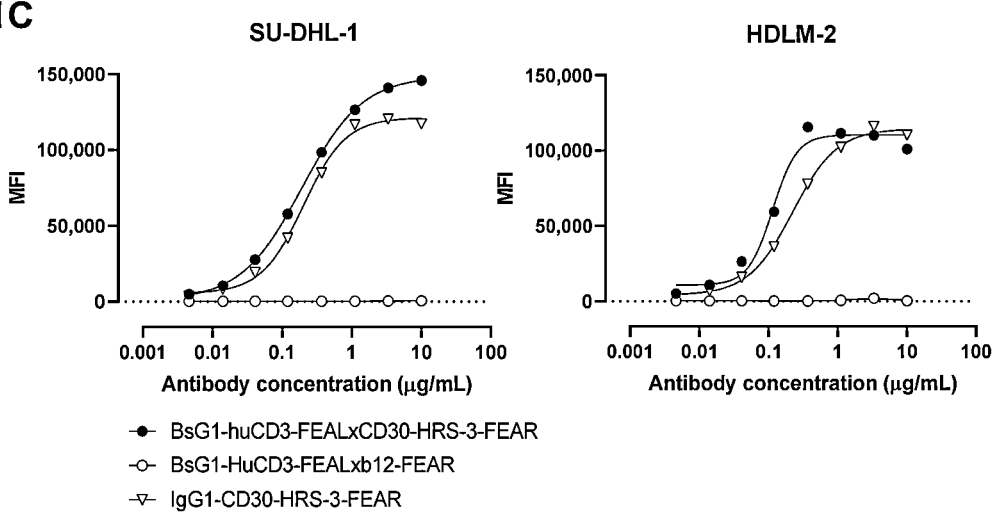

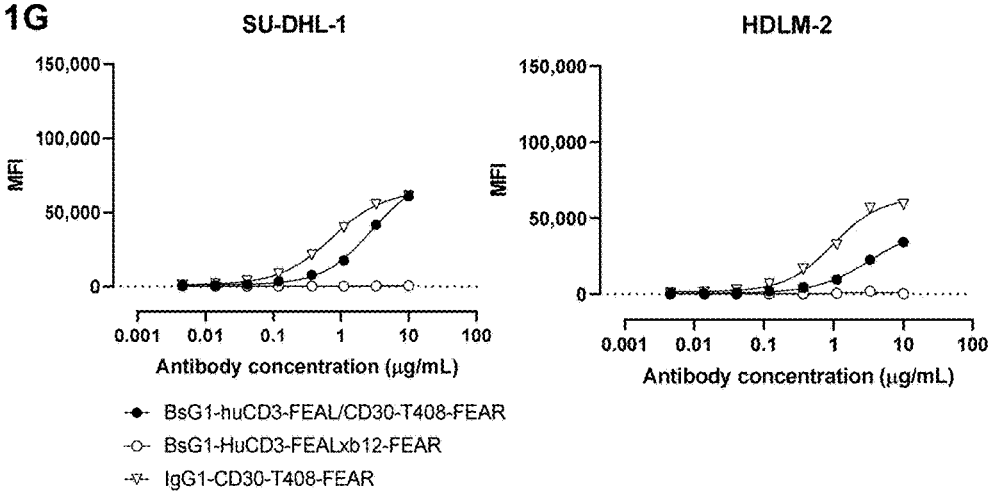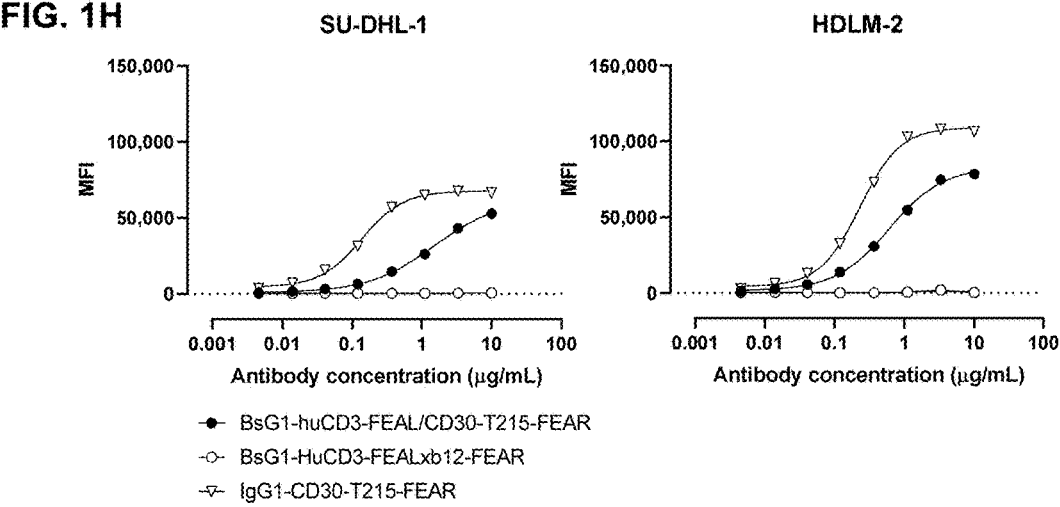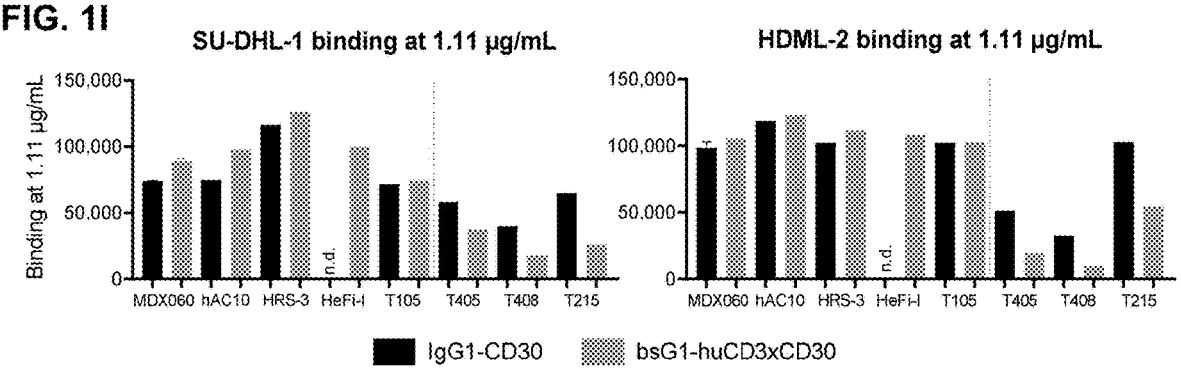

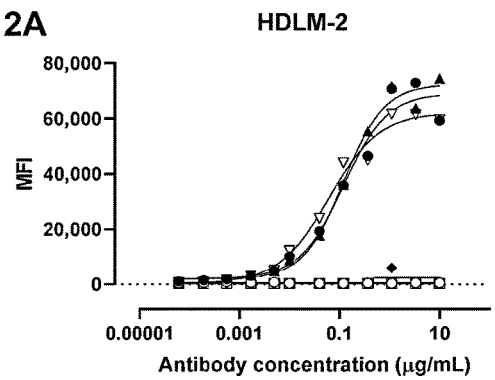
FIG. 2A HDLM-2
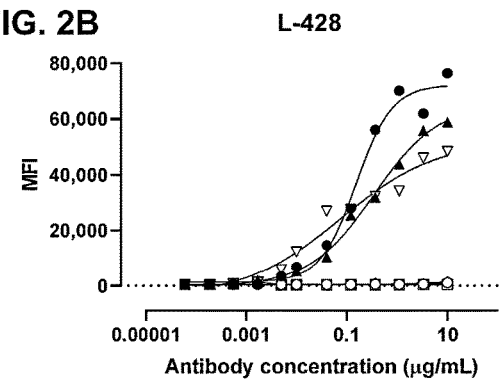
FIG. 2B L-428
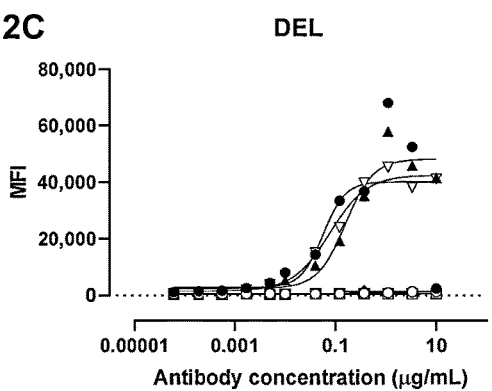
FIG. 2C DEL
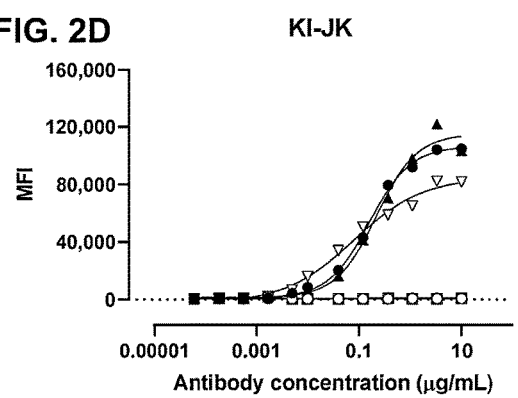
FIG. 2D KI-JK
- BsG1-huCD3-FEALxCD30-MDX060-FERR
- BsG1-HuCD3-FEALxb12-FERR
- BsG1-b12-FEALxCD30-MDX060-FEAR
- IgG1-CD30-MDX060-FERR
- IgG1-huCD3-FEAL
- IgG1-b12-FEAL

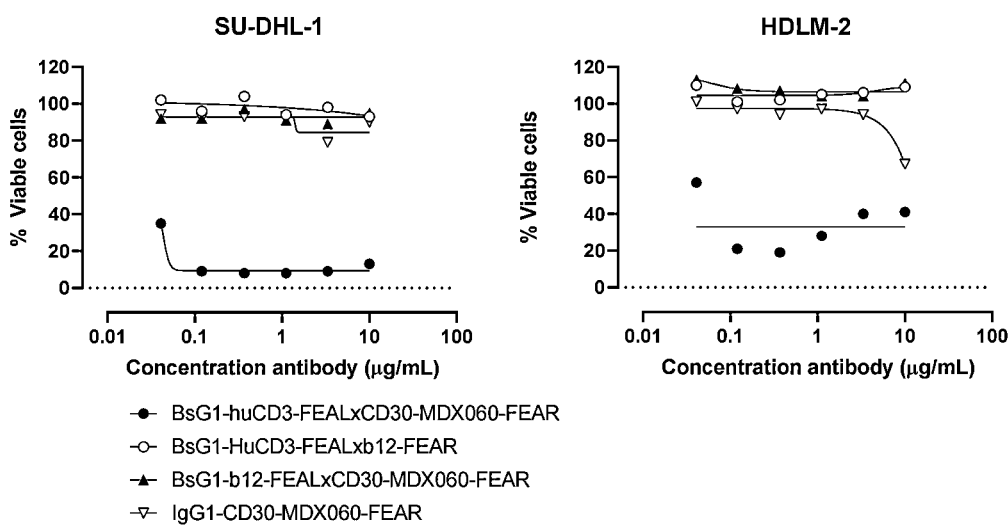
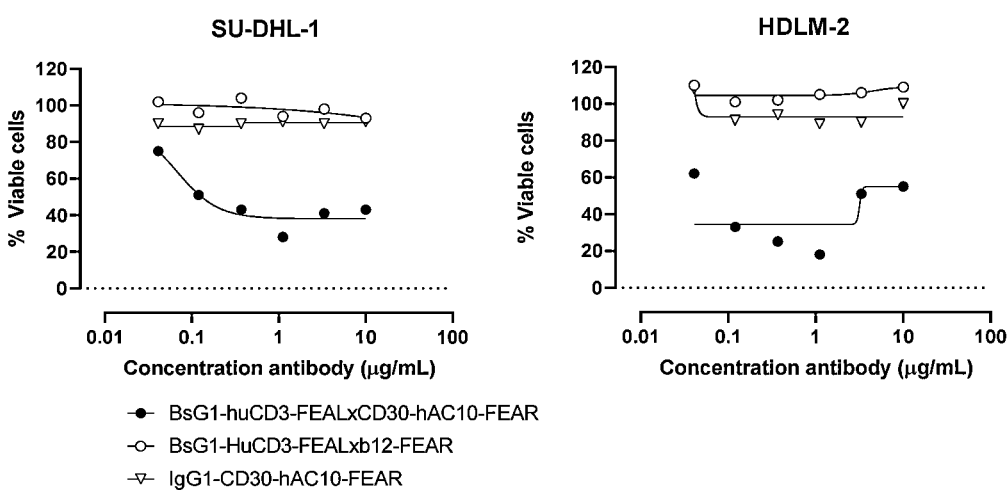
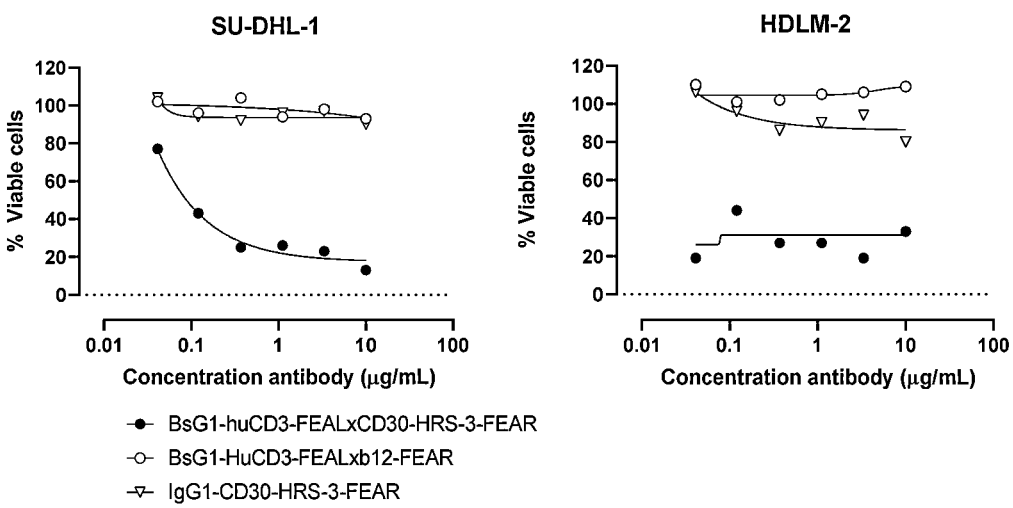

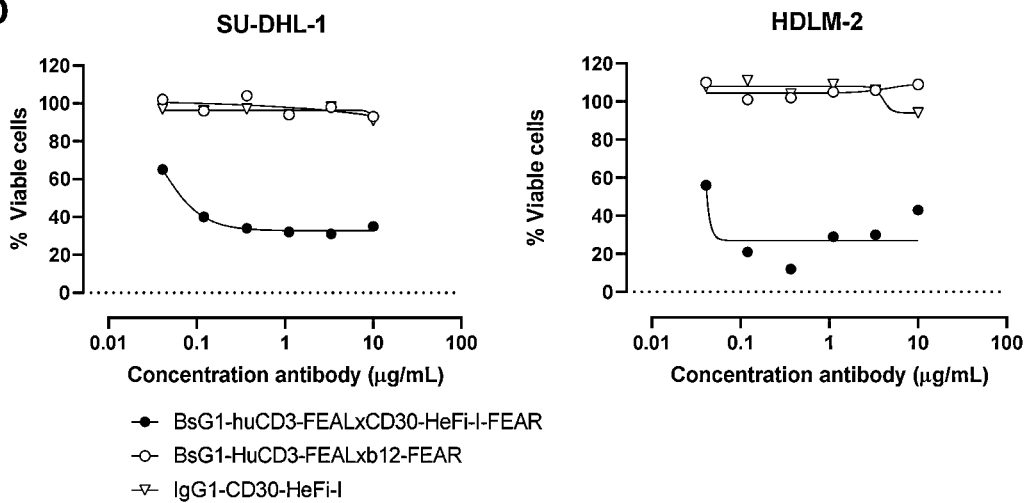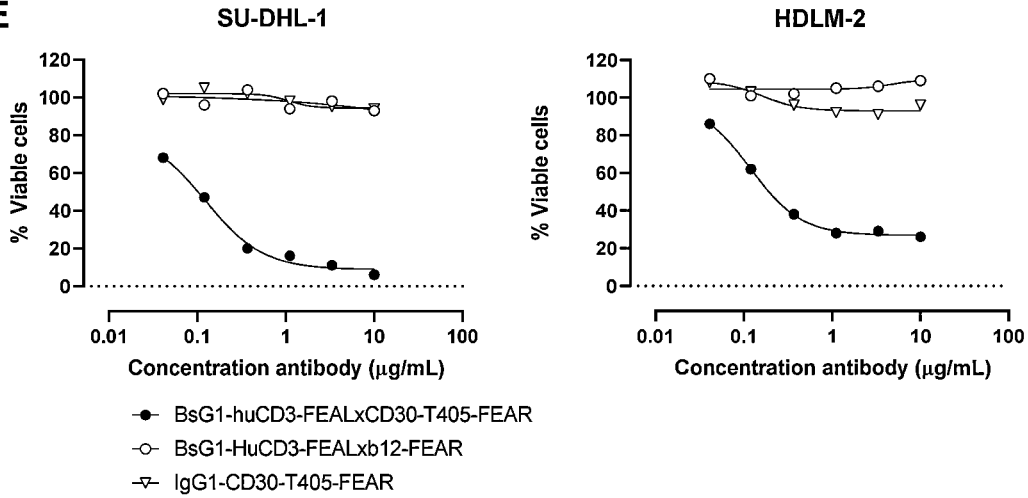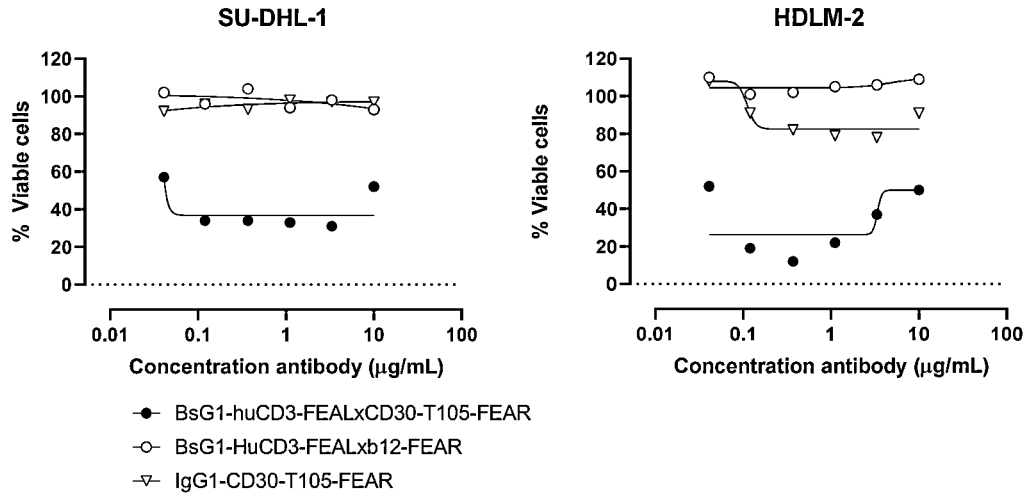

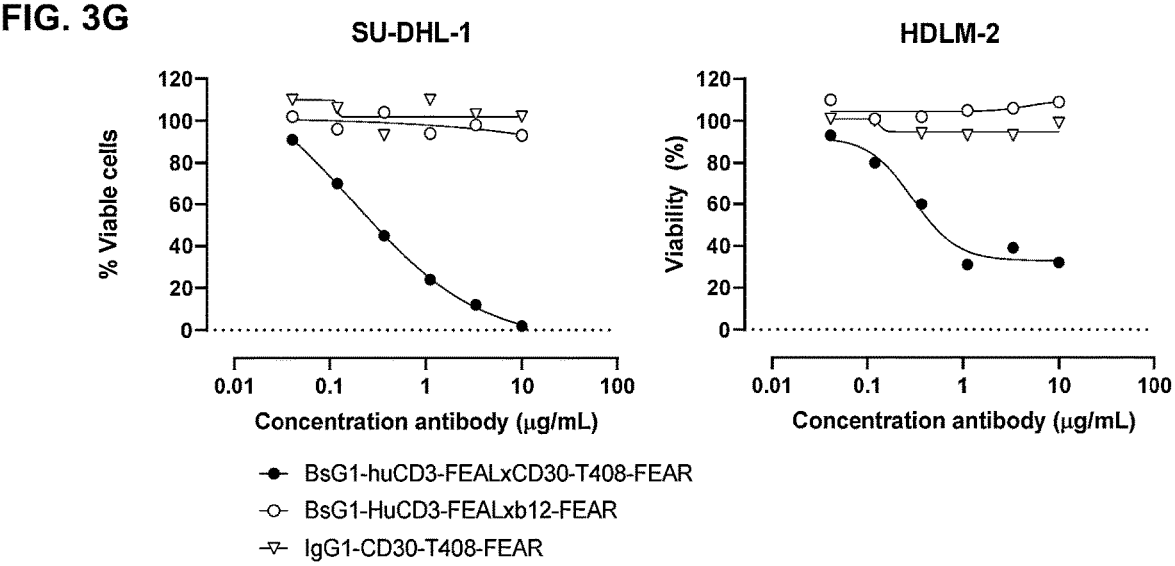
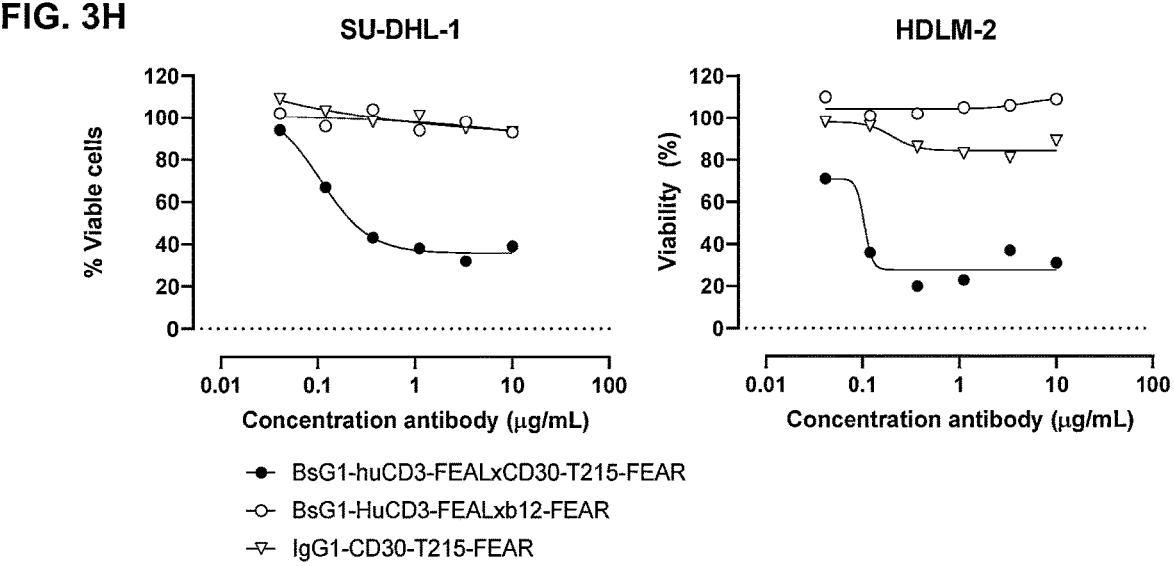

FIG. 4A
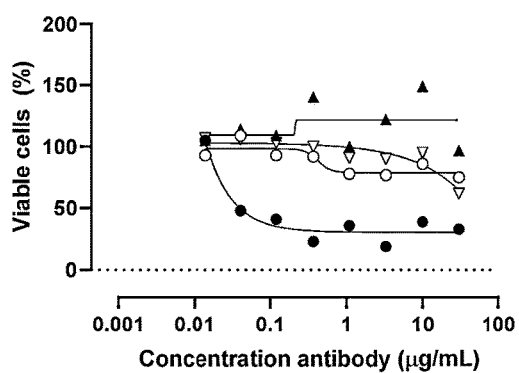
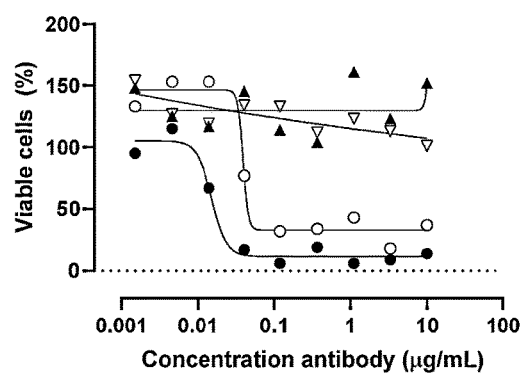
FIG. 4B
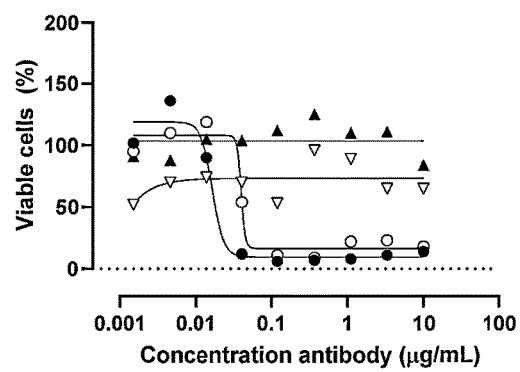
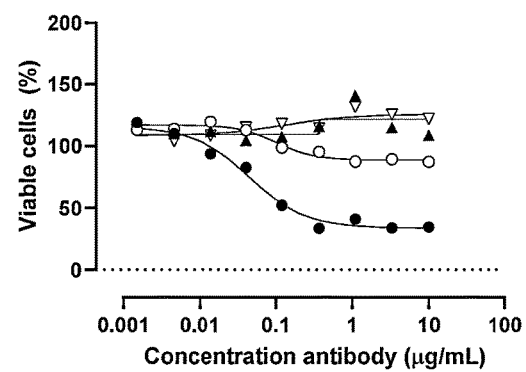
- ● BsG1-huCD3-FEALxCD30-MDX060-FEAR
- ○ BsG1-huCD3-H101G-FEALxCD30-MDX060-FEAR
- ▲ IgG1-huCD3-FEAL
- ▽ IgG1-b12-FEAR

FIG. 4C
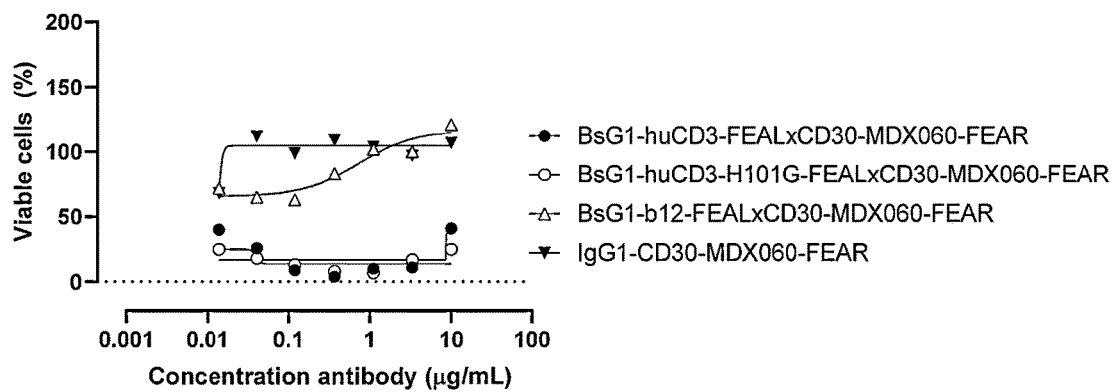
FIG. 4D
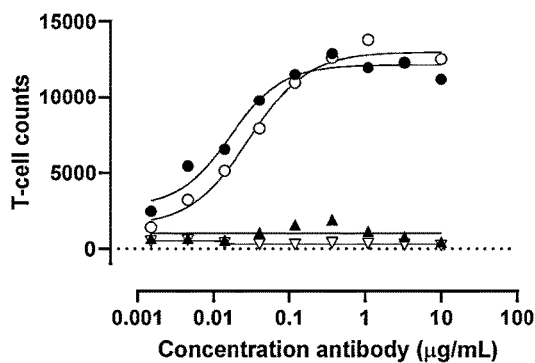
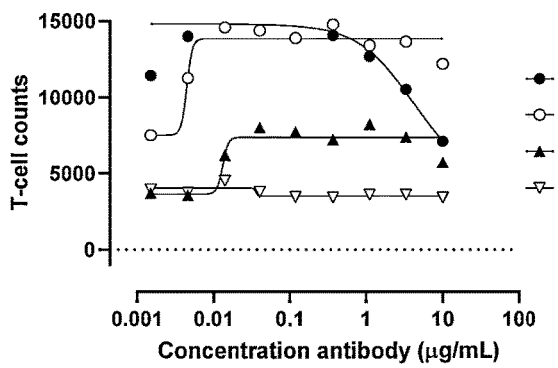

wild-type Expi293F cells

▽ IgG1-CD30-MDX060-FEAR
● BsG1-huCD3-FEALxCD30-MDX060-FEAR
▼ BsG1-huCD3-H101G-FEALxCD30-MDX060-FEAR
▲ BsG1-b12-FEALxCD30-MDX060-FEAR
○ BsG1-huCD3-FEALxb12-FEAR

Expi293F-huCD30 cells

Expi293F-mfCD30 cells

FIG. 6A
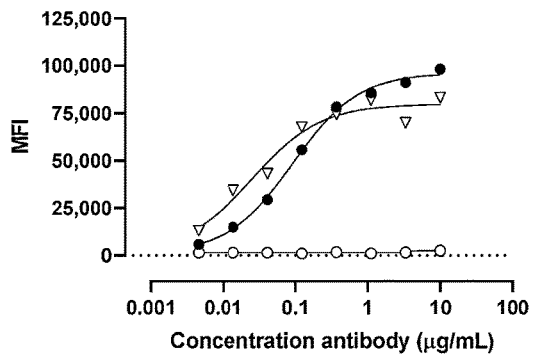
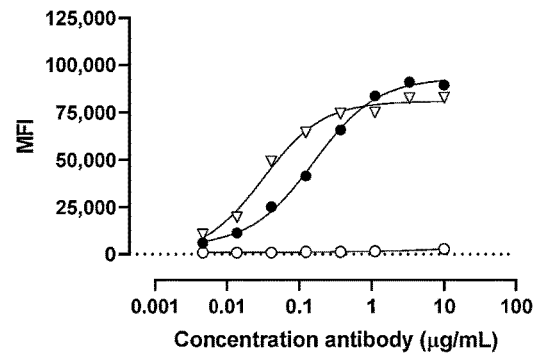
- BsG1-huCD3-FEALxCD30-MDX060-FEAR
- BsG1-huCD3-FEALxb12-FEAR
- IgG1-CD30-MDX060-FEAR
FIG. 6B
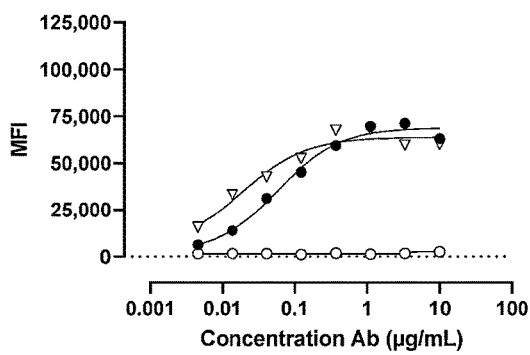
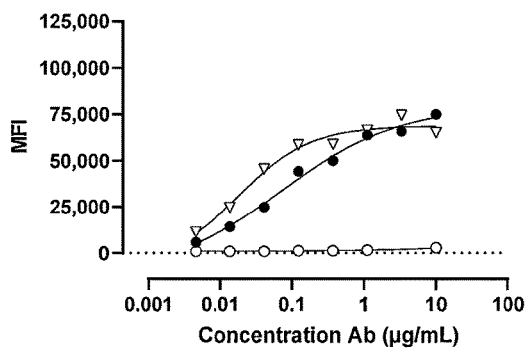
- BsG1-huCD3-FEALxCD30-hAC10-FEAR
- BsG1-huCD3-FEALxb12-FEAR
- IgG1-CD30-hAC10-FEAR

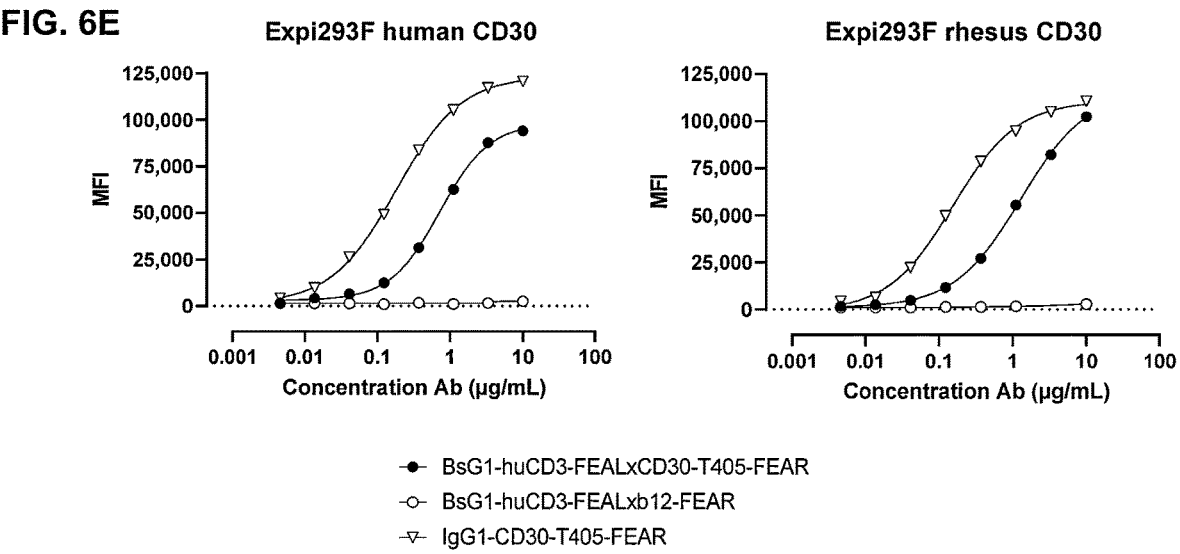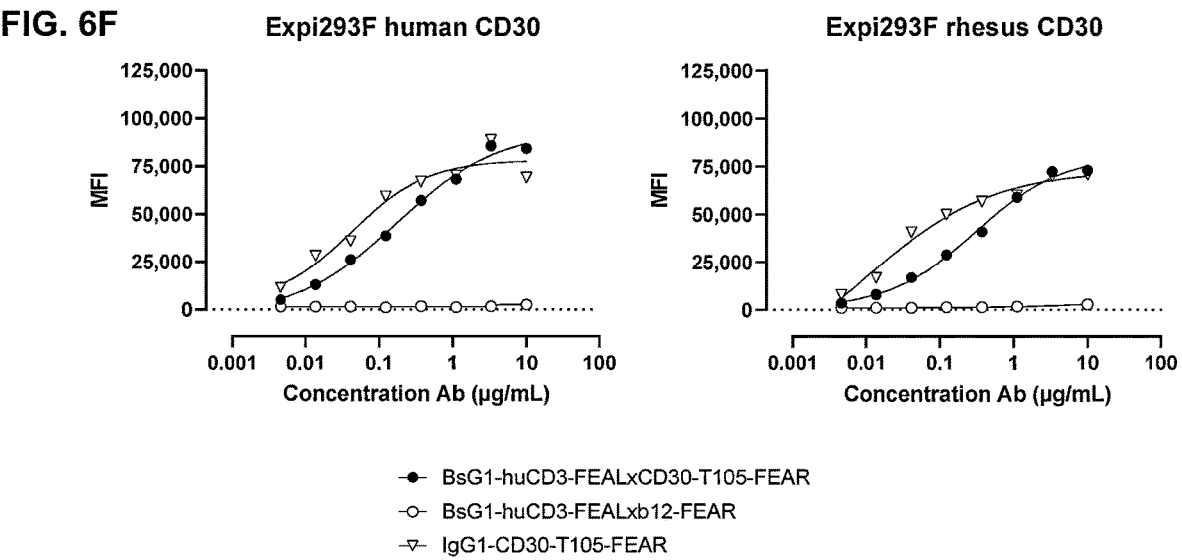

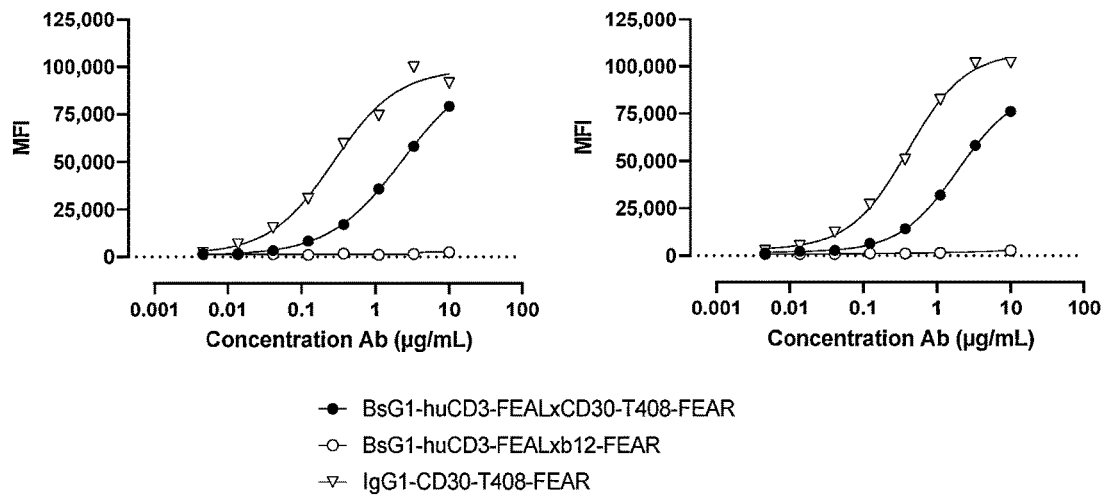
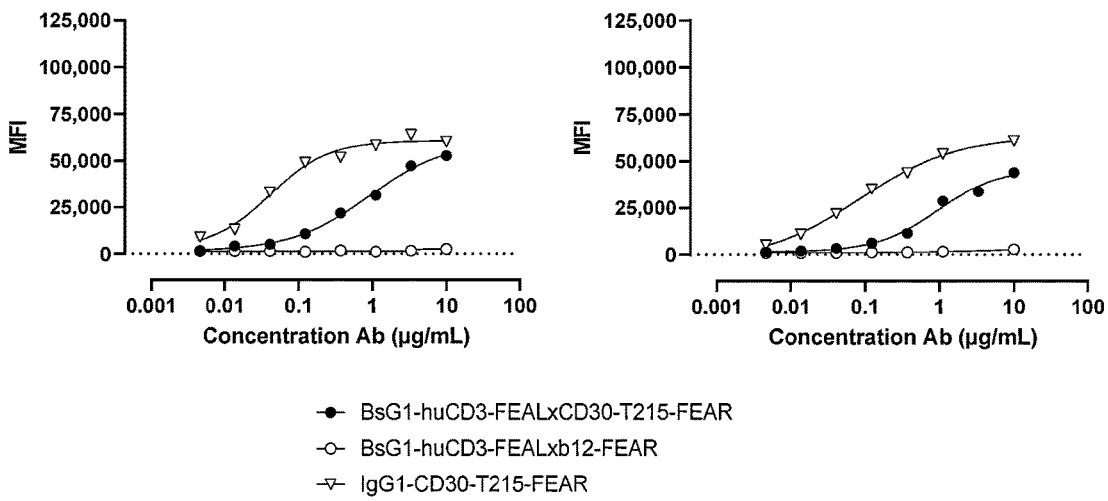

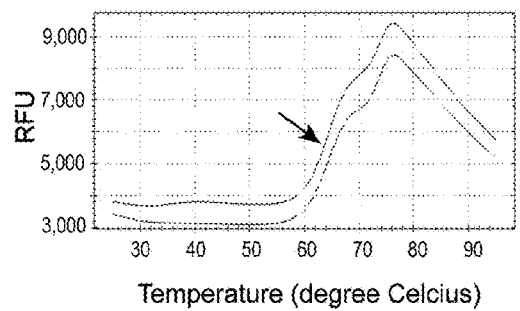
FIG. 7A IgG1-CD30-MDX060-FEAR
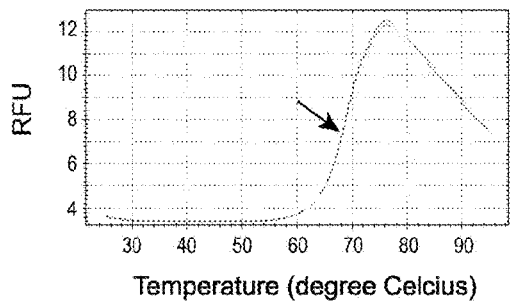
FIG. 7B IgG1-CD30-MDX060-FERR
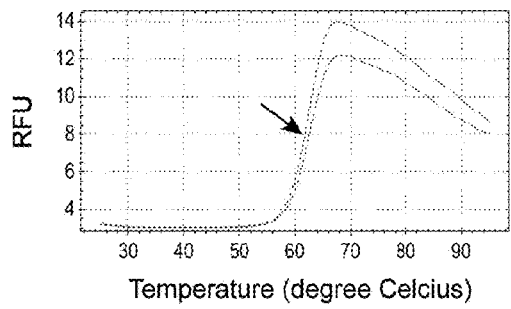
FIG. 7C IgG1-huCD3-FEAL
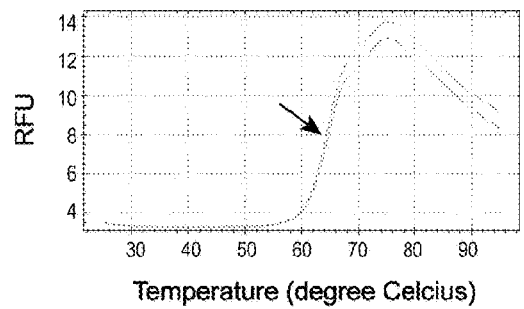
FIG. 7D bsG1-huCD3-FEALxCD30-MDX060-FERR

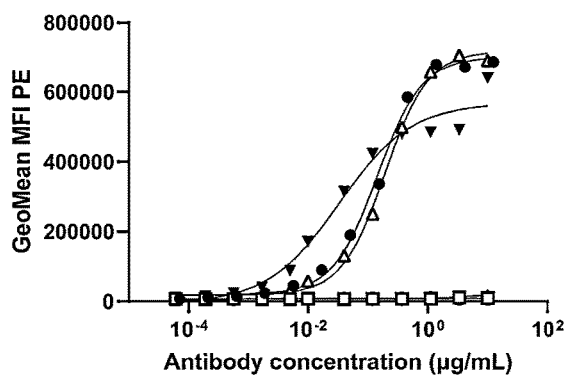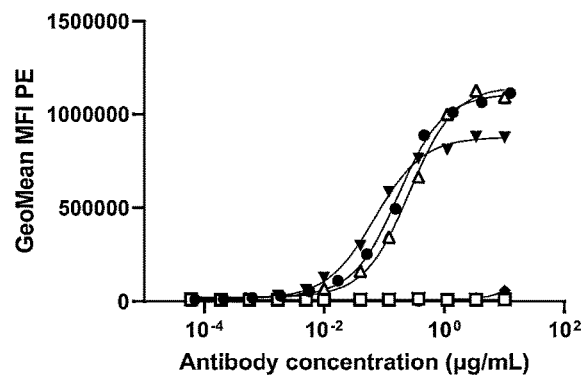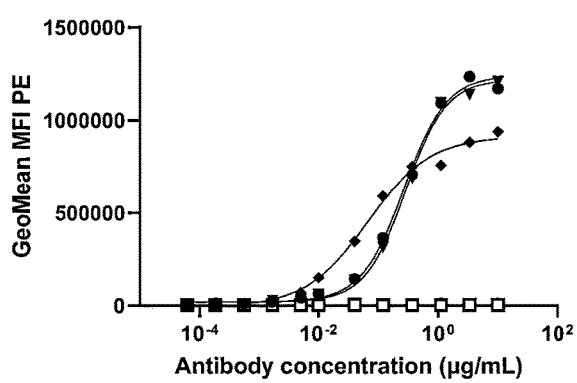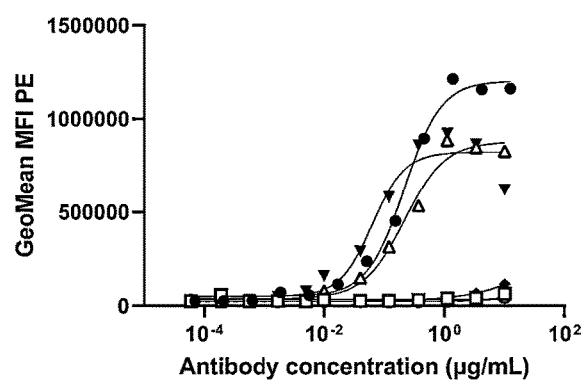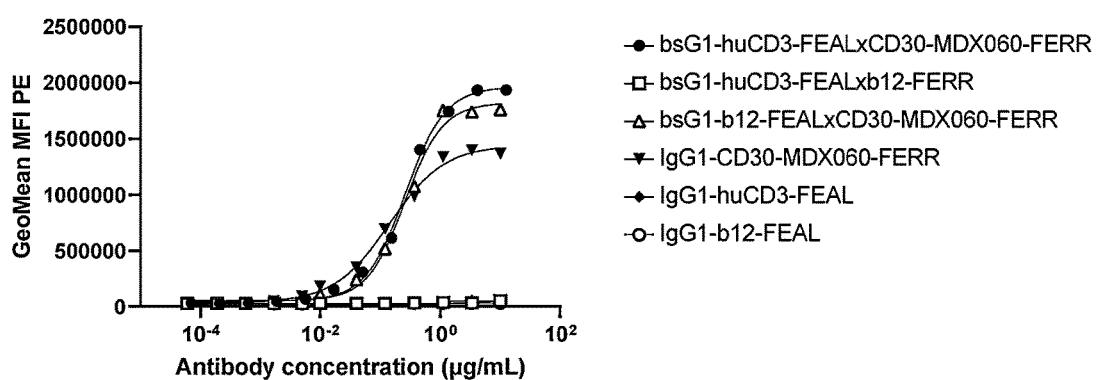

FIG. 10A SUP-T1
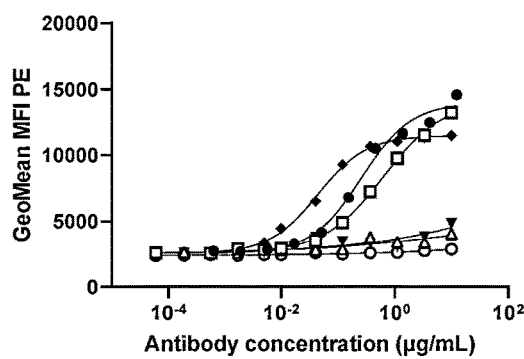
FIG. 10B JVM-2
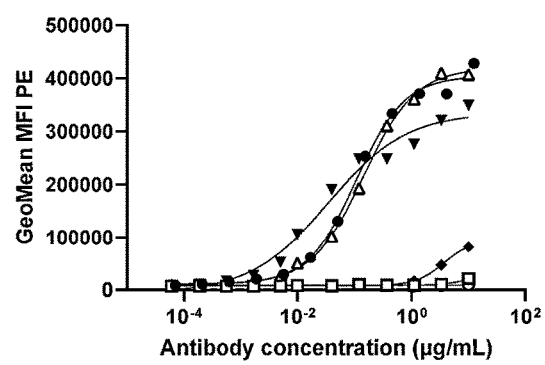
FIG. 10C HH
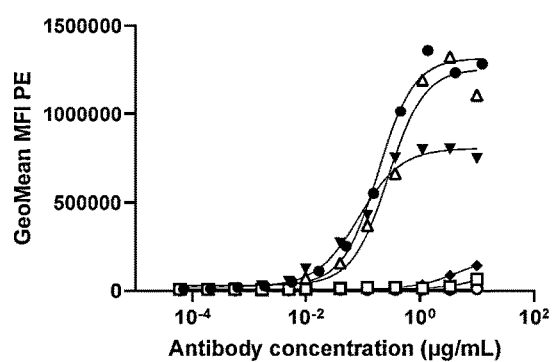
FIG. 10D NCEB-1
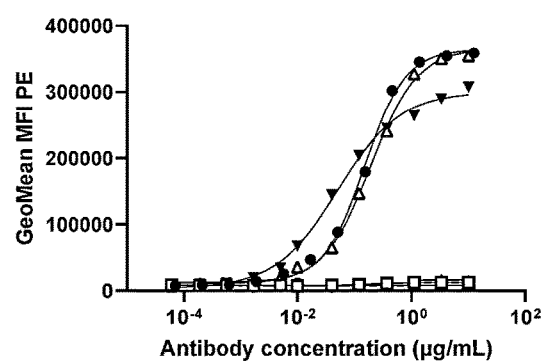
- ●  bsG1-huCD3-FEALxCD30-MDX060-FERR
- □  bsG1-huCD3-FEALxb12-FERR
- △  bsG1-b12-FEALxCD30-MDX060-FERR
- ▼  IgG1-CD30-MDX060-FERR
- ◆  IgG1-huCD3-FEAL
- ○  IgG1-b12-FEAL

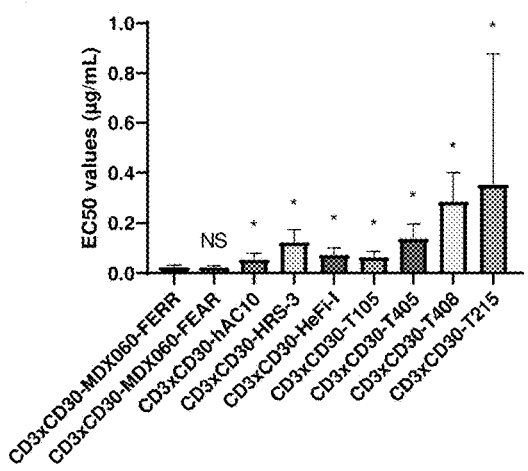
FIG. 13E PD-1 expression in CD4+ T cells
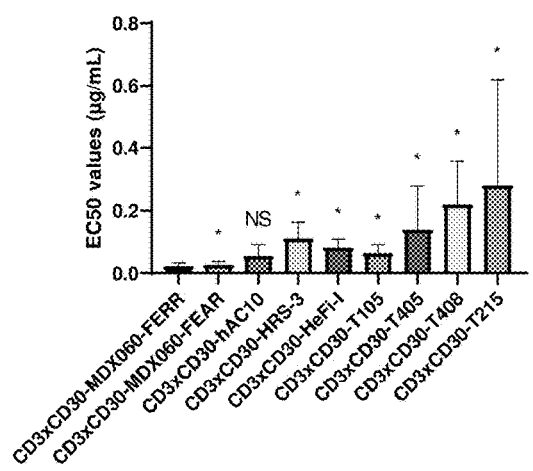
FIG. 13F PD-1 expression in CD8+ T cells

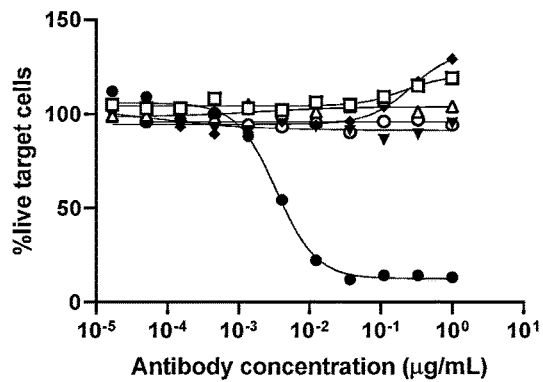
FIG. 14A L-428
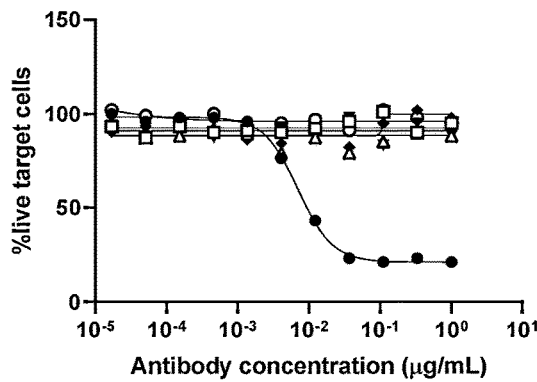
FIG. 14B KM-H2
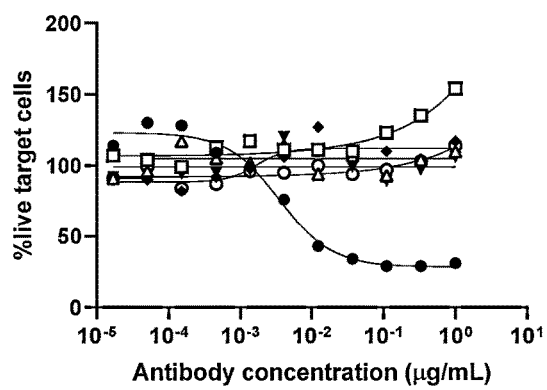
FIG. 14C SUP-M2
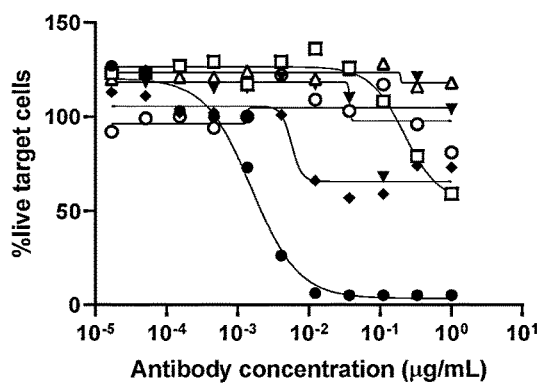
FIG. 14D KI-JK
- ●  bsG1-huCD3-FEALxCD30-MDX060-FERR
- □  bsG1-huCD3-FEALxb12-FERR
- △  bsG1-b12-FEALxCD30-MDX060-FERR
- ▼  IgG1-CD30-MDX060-FERR
- ◆  IgG1-huCD3-FEAL
- ○  IgG1-b12-FEAL

FIG. 15A L-428 CD4+ T cells
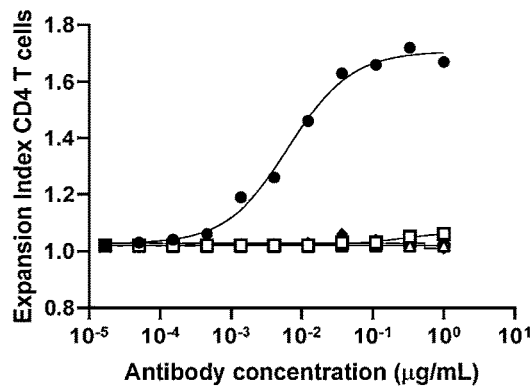
FIG. 15B L-428 CD8+ T cells
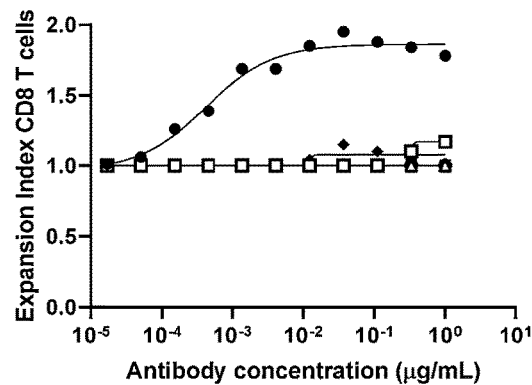
FIG. 15C KI-JK CD4+ T cells
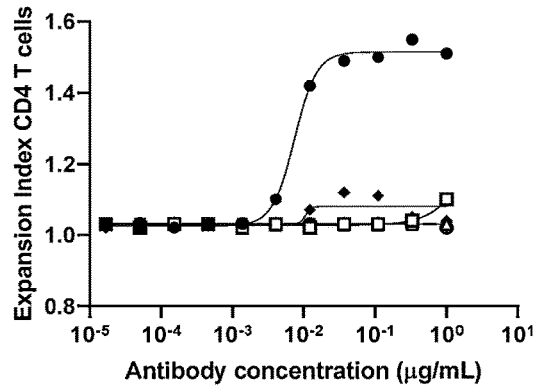
FIG. 15D KI-JK CD8+ T cells
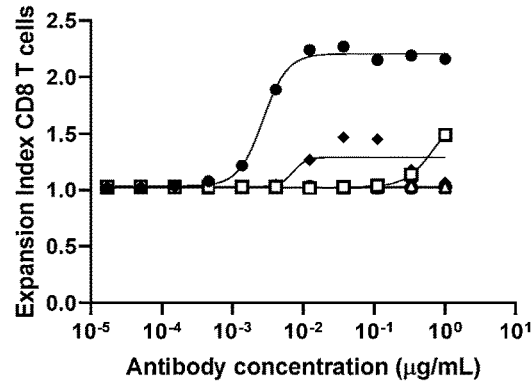
- ● bsG1-huCD3-FEALxCD30-MDX060-FERR
- □ bsG1-huCD3-FEALxb12-FERR
- △ bsG1-b12-FEALxCD30-MDX060-FERR
- ▼ IgG1-CD30-MDX060-FERR
- ◆ IgG1-huCD3-FEAL
- ○ IgG1-b12-FEAL

- ●  bsG1-huCD3-FEALxCD30-MDX060-FERR
- □  bsG1-huCD3-FEALxb12-FERR
- △  bsG1-b12-FEALxCD30-MDX060-FERR
- ▼  IgG1-CD30-MDX060-FERR
- ◆  IgG1-huCD3-FEAL
- ○  IgG1-b12-FEAL

- ● bsG1-huCD3-FEALxCD30-MDX060-FERR
- □ bsG1-huCD3-FEALxb12-FERR
- △ bsG1-b12-FEALxCD30-MDX060-FERR
- ▼ IgG1-CD30-MDX060-FERR
- ◆ IgG1-huCD3-FEAL
- ○ IgG1-b12-FEAL

- ●  bsG1-huCD3-FEALxCD30-MDX060-FERR
- □  bsG1-huCD3-FEALxb12-FERR
- △  bsG1-b12-FEALxCD30-MDX060-FERR
- ▼  IgG1-CD30-MDX060-FERR
- ◆  IgG1-huCD3-FEAL
- ○  IgG1-b12-FEAL

FIG. 25A T-cell mediated cytotoxicity
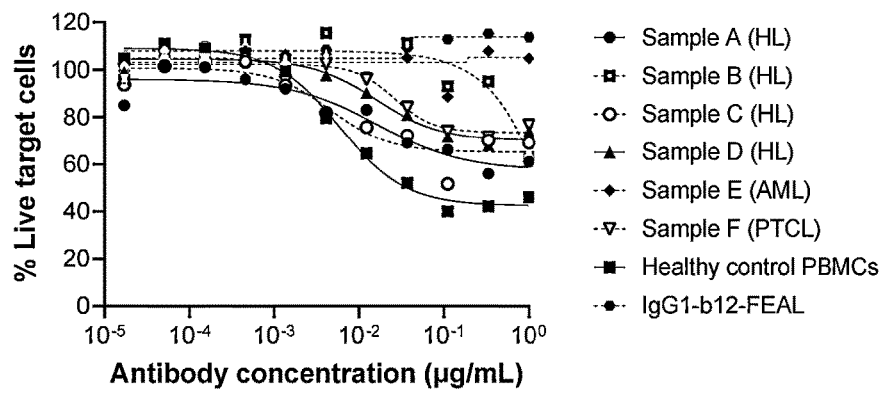
FIG. 25B T-cell activation - CD4$^+$CD25$^+$
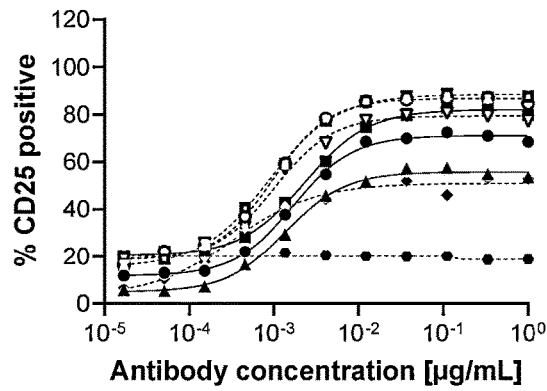
T-cell activation - CD8$^+$CD25$^+$
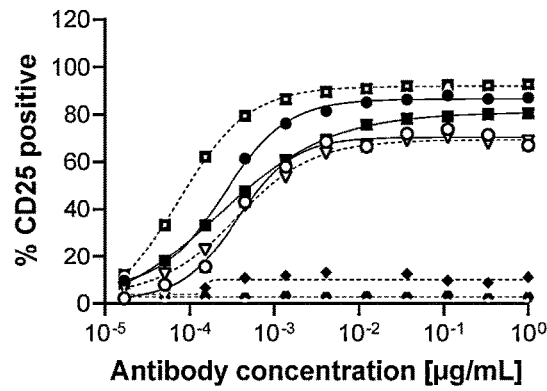

FIG. 25C T-cell activation - $CD4^+CD69^+$
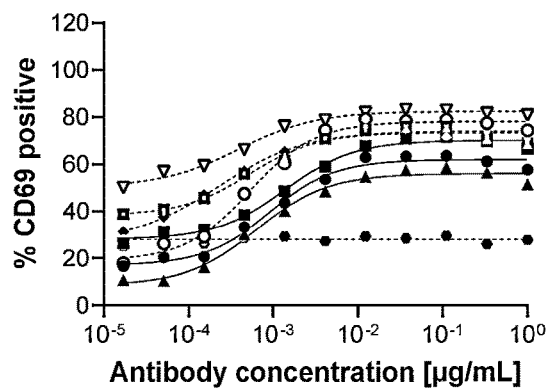
T-cell activation - $CD8^+CD69^+$
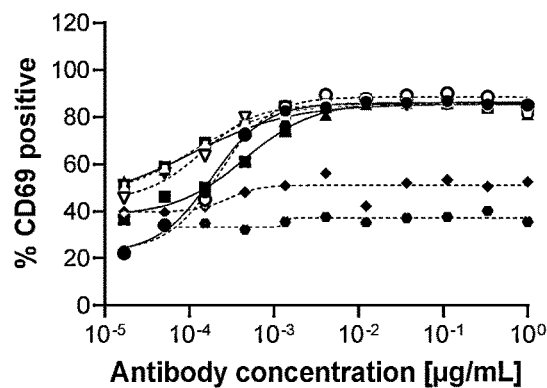
FIG. 25D T-cell activation - $CD4^+PD\text{-}1^+$
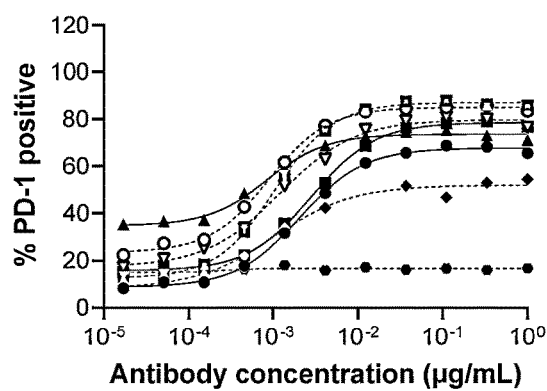
T-cell activation - $CD8^+PD\text{-}1^+$
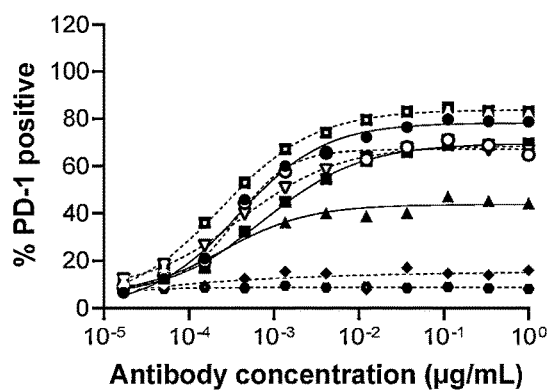
- Sample A (HL)
- Sample B (HL)
- Sample C (HL)
- Sample D (HL)
- Sample E (AML)
- Sample F (PTCL)
- Healthy control PBMCs
- IgG1-b12-FEAL

SEQUENCE LISTING

```
Sequence total quantity: 55
SEQ ID NO: 1              moltype = AA  length = 8
FEATURE                   Location/Qualifiers
REGION                    1..8
                          note = VH CDR1
source                    1..8
                          mol_type = protein
                          organism = synthetic construct
SEQUENCE: 1
GGSFSAYY                                                                    8

SEQ ID NO: 2              moltype = AA  length = 7
FEATURE                   Location/Qualifiers
REGION                    1..7
                          note = VH CDR2
source                    1..7
                          mol_type = protein
                          organism = synthetic construct
SEQUENCE: 2
INHGGGT                                                                     7

SEQ ID NO: 3              moltype = AA  length = 6
FEATURE                   Location/Qualifiers
REGION                    1..6
                          note = VH CDR3
source                    1..6
                          mol_type = protein
                          organism = synthetic construct
SEQUENCE: 3
ASLTAY                                                                      6

SEQ ID NO: 4              moltype = AA  length = 6
FEATURE                   Location/Qualifiers
REGION                    1..6
                          note = VL CDR1
source                    1..6
                          mol_type = protein
                          organism = synthetic construct
SEQUENCE: 4
QGISSW                                                                      6

SEQ ID NO: 5              moltype =    length =
SEQUENCE: 5
000

SEQ ID NO: 6              moltype = AA  length = 9
FEATURE                   Location/Qualifiers
REGION                    1..9
                          note = VL CDR3
source                    1..9
                          mol_type = protein
                          organism = synthetic construct
SEQUENCE: 6
QQYDSYPIT                                                                   9

SEQ ID NO: 7              moltype = AA  length = 8
FEATURE                   Location/Qualifiers
REGION                    1..8
                          note = VH CDR1
source                    1..8
                          mol_type = protein
                          organism = synthetic construct
SEQUENCE: 7
GFTFNTYA                                                                    8

SEQ ID NO: 8              moltype = AA  length = 10
FEATURE                   Location/Qualifiers
REGION                    1..10
                          note = VH CDR2
source                    1..10
                          mol_type = protein
                          organism = synthetic construct
SEQUENCE: 8
IRSKYNNYAT                                                                 10

SEQ ID NO: 9              moltype = AA  length = 16
FEATURE                   Location/Qualifiers
REGION                    1..16
```

```
                        note = VH CDR3
VARIANT                 3
                        note = H or G
source                  1..16
                        mol_type = protein
                        organism = synthetic construct
SEQUENCE: 9
VRXGNFGNSY VSWFAY                                                    16

SEQ ID NO: 10           moltype = AA  length = 9
FEATURE                 Location/Qualifiers
REGION                  1..9
                        note = VL CDR1
source                  1..9
                        mol_type = protein
                        organism = synthetic construct
SEQUENCE: 10
TGAVTTSNY                                                             9

SEQ ID NO: 11           moltype =    length =
SEQUENCE: 11
000

SEQ ID NO: 12           moltype = AA  length = 9
FEATURE                 Location/Qualifiers
REGION                  1..9
                        note = VL CDR3
source                  1..9
                        mol_type = protein
                        organism = synthetic construct
SEQUENCE: 12
ALWYSNLWV                                                             9

SEQ ID NO: 13           moltype = AA  length = 112
FEATURE                 Location/Qualifiers
REGION                  1..112
                        note = VH
source                  1..112
                        mol_type = protein
                        organism = synthetic construct
SEQUENCE: 13
QVQLQQWGAG LLKPSETLSL TCAVYGGSFS AYYWSWIRQP PGKGLEWIGD INHGGGTNYN    60
PSLKSRVTIS VDTSKNQFSL KLNSVTAADT AVYYCASLTA YWGQGSLVTV SS           112

SEQ ID NO: 14           moltype = AA  length = 107
FEATURE                 Location/Qualifiers
REGION                  1..107
                        note = VL
source                  1..107
                        mol_type = protein
                        organism = synthetic construct
SEQUENCE: 14
DIQMTQSPTS LSASVGDRVT ITCRASQGIS SWLTWYQQKP EKAPKSLIYA ASSLQSGVPS    60
RFSGSGSGTD FTLTISSLQP EDFATYYCQQ YDSYPITFGQ GTRLEIK                 107

SEQ ID NO: 15           moltype = AA  length = 125
FEATURE                 Location/Qualifiers
REGION                  1..125
                        note = VH
VARIANT                 101
                        note = H or G
source                  1..125
                        mol_type = protein
                        organism = synthetic construct
SEQUENCE: 15
EVKLVESGGG LVQPGGSLRL SCAASGFTFN TYAMNWVRQA PGKGLEWVAR IRSKYNNYAT    60
YYADSVKDRF TISRDDSKSS LYLQMNNLKT EDTAMYYCVR XGNFGNSYVS WFAYWGQGTL   120
VTVSS                                                               125

SEQ ID NO: 16           moltype = AA  length = 109
FEATURE                 Location/Qualifiers
REGION                  1..109
                        note = VL
source                  1..109
                        mol_type = protein
                        organism = synthetic construct
SEQUENCE: 16
QAVVTQEPSF SVSPGGTVTL TCRSSTGAVT TSNYANWVQQ TPGQAFRGLI GGTNKRAPGV    60
PARFSGSLIG DKAALTITGA QADDESIYFC ALWYSNLWVF GGGTKLTVL               109
```

```
SEQ ID NO: 17            moltype = AA  length = 441
FEATURE                  Location/Qualifiers
REGION                   1..441
                         note = Heavy chain
source                   1..441
                         mol_type = protein
                         organism = synthetic construct
SEQUENCE: 17
QVQLQQWGAG LLKPSETLSL TCAVYGGSFS AYYWSWIRQP PGKGLEWIGD INHGGGTNYN    60
PSLKSRVTIS VDTSKNQFSL KLNSVTAADT AVYYCASLTA YWQGSLVTV SSASTKGPSV    120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKRV EPKSCDKTHT CPPCPAPEFE RGPSVFLFPP   240
KPKDTLMISR TPEVTCVVVD VSHEDPEVKF NWYVDGVEVH NAKTKPREEQ YNSTYRVVSV   300
LTVLHQDWLN GKEYKCKVSN KALPAPIEKT ISKAKGQPRE PQVYTLPPSR EEMTKNQVSL   360
TCLVKGFYPS DIAVEWESNG QPENNYKTTP PVLDSDGSFF LYSRLTVDKS RWQQGNVFSC   420
SVMHEALHNH YTQKSLSLSP G                                             441

SEQ ID NO: 18            moltype = AA  length = 214
FEATURE                  Location/Qualifiers
REGION                   1..214
                         note = Light chain
source                   1..214
                         mol_type = protein
                         organism = synthetic construct
SEQUENCE: 18
DIQMTQSPTS LSASVGDRVT ITCRASQGIS SWLTWYQQKP EKAPKSLIYA ASSLQSGVPS    60
RFSGSGSGTD FTLTISSLQP EDFATYYCQQ YDSYPITFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 19            moltype = AA  length = 454
FEATURE                  Location/Qualifiers
REGION                   1..454
                         note = Heavy chain
source                   1..454
                         mol_type = protein
                         organism = synthetic construct
SEQUENCE: 19
EVKLVESGGG LVQPGGSLRL SCAASGFTFN TYAMNWVRQA PGKGLEWVAR IRSKYNNYAT    60
YYADSVKDRF TISRDDSKSS LYLQMNNLKT EDTAMYYCVR HGNFGNSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
EFEGGPSVFL FPPKPKDTLM ISRTPEVTCV VVASHEDPE VKFNWYVDGV EVHNAKTKPR    300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFLLYSKLTV   420
DKSRWQQGNV FSCSVMHEAL HNHYTQKSLS LSPG                               454

SEQ ID NO: 20            moltype = AA  length = 215
FEATURE                  Location/Qualifiers
REGION                   1..215
                         note = Light chain
source                   1..215
                         mol_type = protein
                         organism = synthetic construct
SEQUENCE: 20
QAVVTQEPSF SVSPGGTVTL TCRSSTGAVT TSNYANWVQQ TPGQAFRGLI GGTNKRAPGV    60
PARFSGSLIG DKAALTITGA QADDESIYFC ALWYSNLWVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                              215

SEQ ID NO: 21            moltype = AA  length = 446
FEATURE                  Location/Qualifiers
REGION                   1..446
                         note = Heavy chain
source                   1..446
                         mol_type = protein
                         organism = synthetic construct
SEQUENCE: 21
QVQLVQSGAE VKKPGASVKV SCKASGYTFT DYYITWVRQA PGQGLEWMGW IYPGSGNTKY    60
NEKFKGRVTM TRDTSISTAY MELSRLRSDD TAVYYCANYG NYWFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APEFEGGPSV   240
FLFPPKPKDT LMISRTPEVT CVVVAVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSRL TVDKSRWQQG   420
NVFSCSVMHE ALHNHYTQKS LSLSPG                                        446

SEQ ID NO: 22            moltype = AA  length = 218
```

```
FEATURE            Location/Qualifiers
REGION             1..218
                   note = Light chain
source             1..218
                   mol_type = protein
                   organism = synthetic construct
SEQUENCE: 22
DIVMTQSPDS LAVSLGERAT INCKASQSVD FDGDSYMNWY QQKPGQPPKL LIYAASNLES   60
GVPDRFSGSG SGTDFTLTIS SLQAEDVAVY YCQQSNEDPW TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 23      moltype = AA   length = 452
FEATURE            Location/Qualifiers
REGION             1..452
                   note = Heavy chain
source             1..452
                   mol_type = protein
                   organism = synthetic construct
SEQUENCE: 23
QVQLQQSGAE LARPGASVKM SCKASGYTFT TYTIHWVRQR PGHDLEWIGY INPSSGYSDY   60
NQNFKGKTTL TADKSSNTAY MQLNSLTSED SAVYYCARRA DYGNYEYTWF AYWGQGTTVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEF  240
EGGPSVFLFP PKPKDTLMIS RTPEVTCVVV AVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSRLTVDK  420
SRWQQGNVFS CSVMHEALHN HYTQKSLSLS PG                                452

SEQ ID NO: 24      moltype = AA   length = 214
FEATURE            Location/Qualifiers
REGION             1..214
                   note = Light chain
source             1..214
                   mol_type = protein
                   organism = synthetic construct
SEQUENCE: 24
DIVMTQSPKF MSTSVGDRVT VTCKASQNVG TNVAWFQQKP GQSPKVLIYS ASYRYSGVPD   60
RFTGSGSGTD FTLTISNVQS EDLAEYFCQQ YHTYPLTFGG GTKLEINRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 25      moltype = AA   length = 454
FEATURE            Location/Qualifiers
REGION             1..454
                   note = Heavy chain
source             1..454
                   mol_type = protein
                   organism = synthetic construct
SEQUENCE: 25
EVKLVESGGG LVQPGGSLRL SCATSGFTFS DYYMNWVRQP PGKALEWLGF IRNKANGYTT   60
EFSASVMGRF TISRDDSQSI LYLQMNTLRA EDSATYYCAR DPPYGNPHYY AMDYWGQGTS  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCDK THTCPPCPAP  240
EFEGGPSVFL FPPKPKDTLM ISRTPEVTCV VVAVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFFLYSRLTV  420
DKSRWQQGNV FSCSVMHEAL HNHYTQKSLS LSPG                              454

SEQ ID NO: 26      moltype = AA   length = 218
FEATURE            Location/Qualifiers
REGION             1..218
                   note = Light chain
source             1..218
                   mol_type = protein
                   organism = synthetic construct
SEQUENCE: 26
DIVLTQSPAS LAVSLGQRAT ISCRASKSVS ASGYNYMHWY QQKAGQPPKL LIHLASNLES   60
GVPARFSGSG SGTDFTLNIH PVEEEDSATY YCQHSGELPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 27      moltype = AA   length = 441
FEATURE            Location/Qualifiers
REGION             1..441
                   note = Heavy chain
source             1..441
                   mol_type = protein
                   organism = synthetic construct
```

```
SEQUENCE: 27
QVQLQQIGAE LVRPGASVKL SCKASGYTFN NYWINWVKQR PGQGLEWIGN IYPSDSRSNY    60
NQKFKDKATL TVDKPSSTAY MQLSSPTSED SAVYYCTLGS YWQGTLVTV  SAASTKGPSV   120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKRV EPKSCDKTHT CPPCPAPEFE GGPSVFLFPP   240
KPKDTLMISR TPEVTCVVVA VSHEDPEVKF NWYVDGVEVH NAKTKPREEQ YNSTYRVVSV   300
LTVLHQDWLN GKEYKCKVSN KALPAPIEKT ISKAKGQPRE PQVYTLPPSR EEMTKNQVSL   360
TCLVKGFYPS DIAVEWESNG QPENNYKTTP PVLDSDGSFF LYSRLTVDKS RWQQGNVFSC   420
SVMHEALHNH YTQKSLSLSP G                                            441

SEQ ID NO: 28           moltype = AA  length = 219
FEATURE                 Location/Qualifiers
REGION                  1..219
                        note = Light chain
source                  1..219
                        mol_type = protein
                        organism = synthetic construct
SEQUENCE: 28
DVVMTQTPLT LSVTIGQPAS ISCKSSQSLS DSDGKTYLNW LLQRPGQSPK RLIYLVSKLD    60
SGVPDRFTGS GSGTDFTLKI SRVEAEDLGV YYCWQGAHFP RTFGGGTKLE IKRTVAAPSV   120
FIFPPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 29           moltype = AA  length = 450
FEATURE                 Location/Qualifiers
REGION                  1..450
                        note = Heavy chain
source                  1..450
                        mol_type = protein
                        organism = synthetic construct
SEQUENCE: 29
QVTLKESGPG ILQPSQTLSL TCSFSGFSLS TSGMGVSWIR QPSGKDLEWL AHIYWDDDKR    60
YNPSLKSRLT ISKDTSSNQV FLKITSVDTA DTATYYCARR ADGLYFYLDV WGAGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVAV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSRLTVDKSR   420
WQQGNVFSCS VMHEALHNHY TQKSLSLSPG                                    450

SEQ ID NO: 30           moltype = AA  length = 214
FEATURE                 Location/Qualifiers
REGION                  1..214
                        note = Light chain
source                  1..214
                        mol_type = protein
                        organism = synthetic construct
SEQUENCE: 30
DIVMTQSQKF MSTSVGDRVS VTCKASQNVN TNVAWYQQKP GQSPEALIYS ASYRYSGVPD    60
RFTGSGSGTD FTLTISNVQS EDLAEYFCQQ YNSYPLTFGS GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 31           moltype = AA  length = 441
FEATURE                 Location/Qualifiers
REGION                  1..441
                        note = Heavy chain
source                  1..441
                        mol_type = protein
                        organism = synthetic construct
SEQUENCE: 31
QVQLQQPGAE LVRPGASVKL SCKASGYTFT SYWINWVKQR PGQGLEWIGN IYPSDSYSNY    60
NQKFKDKATL TVDKSSSTAY MQLSSPTSED SAVYYCTLGS YWQGTLVTV  SAASTKGPSV   120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKRV EPKSCDKTHT CPPCPAPEFE GGPSVFLFPP   240
KPKDTLMISR TPEVTCVVVA VSHEDPEVKF NWYVDGVEVH NAKTKPREEQ YNSTYRVVSV   300
LTVLHQDWLN GKEYKCKVSN KALPAPIEKT ISKAKGQPRE PQVYTLPPSR EEMTKNQVSL   360
TCLVKGFYPS DIAVEWESNG QPENNYKTTP PVLDSDGSFF LYSRLTVDKS RWQQGNVFSC   420
SVMHEALHNH YTQKSLSLSP G                                            441

SEQ ID NO: 32           moltype = AA  length = 219
FEATURE                 Location/Qualifiers
REGION                  1..219
                        note = Light chain
source                  1..219
                        mol_type = protein
                        organism = synthetic construct
SEQUENCE: 32
DVVMTQTPLT LSVTIGQPAS ISCKSSQSLS DSDGKTYLNW LLQRPGQSPK RLIYLVSKLD    60
```

```
SGVPDRFTGS GSGTDFTLKI SRVEAEDLGV YYCWQGAHFP RTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 33           moltype = AA   length = 452
FEATURE                 Location/Qualifiers
REGION                  1..452
                        note = Heavy chain
source                  1..452
                        mol_type = protein
                        organism = synthetic construct
SEQUENCE: 33
QVTLKESGPG ILQPSQTLSL TCSFSGFSLS VSGMGVSWIR QPSGKGLEWL AHIHWDDDRR   60
SNPSLRSRLT ISKDTSNNQV FLKITSVDTA DTATYYCARR PDLYGNYFFF DFWGQGTTLT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEF  240
EGGPSVFLFP PKPKDTLMIS RTPEVTCVVV AVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSRLTVDK  420
SRWQQGNVFS CSVMHEALHN HYTQKSLSLS PG                                452

SEQ ID NO: 34           moltype = AA   length = 214
FEATURE                 Location/Qualifiers
REGION                  1..214
                        note = Light chain
source                  1..214
                        mol_type = protein
                        organism = synthetic construct
SEQUENCE: 34
DIVMTQSQKF MSTSVGDRVS VTCKASQNVF TNVAWYQQKL GQSPKPLIYS ASYRYSGVPD   60
RFTGSGSGTD FTLTISDVQS EDLAEYFCQQ YNSYPVTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 35           moltype = AA   length = 454
FEATURE                 Location/Qualifiers
REGION                  1..454
                        note = Heavy chain
source                  1..454
                        mol_type = protein
                        organism = synthetic construct
SEQUENCE: 35
EVKLVESGGG LVQPGGSLRL SCAASGFTFN TYAMNWVRQA PGKGLEWVAR IRSKYNNYAT   60
YYADSVKDRF TISRDDSKSS LYLQMNNLKT EDTAMYYCVR GGNFGNSYVS WFAYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCDK THTCPPCPAP  240
EFEGGPSVFL FPPKPKDTLM ISRTPEVTCV VVAVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFLLYSKLTV  420
DKSRWQQGNV FSCSVMHEAL HNHYTQKSLS LSPG                              454

SEQ ID NO: 36           moltype = AA   length = 456
FEATURE                 Location/Qualifiers
REGION                  1..456
                        note = Heavy chain
source                  1..456
                        mol_type = protein
                        organism = synthetic construct
SEQUENCE: 36
QVQLVQSGAE VKKPGASVKV SCQASGYRFS NFVIHWVRQA PGQRFEWMGW INPYNGNKEF   60
SAKFQDRVTF TADTSANTAY MELRSLRSAD TAVYYCARVG PYSWDDSPQD NYYMDVWGKG  120
TTVIVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKRVEPKSC DKTHTCPPCP  240
APEFEGGPSV FLFPPKPKDT LMISRTPEVT CVVVAVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLTCLVK GFYPSDIAVE WESNGQPENN YKTTPPVLDS DGSFLLYSKL  420
TVDKSRWQQG NVFSCSVMHE ALHNHYTQKS LSLSPG                            456

SEQ ID NO: 37           moltype = AA   length = 215
FEATURE                 Location/Qualifiers
REGION                  1..215
                        note = Light chain
source                  1..215
                        mol_type = protein
                        organism = synthetic construct
SEQUENCE: 37
EIVLTQSPGT LSLSPGERAT FSCRSSHSIR SRRVAWYQHK PGQAPRLVIH GVSNRASGIS   60
DRFSGSGSGT DFTLTITRVE PEDFALYYCQ VYGASSYTFG QGTKLERKRT VAAPSVFIFP  120
PSDEQLKSGT ASVVCLLNNF YPREAKVQWK VDNALQSGNS QESVTEQDSK DSTYSLSSTL  180
```

```
TLSKADYEKH KVYACEVTHQ GLSSPVTKSF NRGEC                              215

SEQ ID NO: 38           moltype = AA  length = 456
FEATURE                 Location/Qualifiers
REGION                  1..456
                        note = Heavy chain
source                  1..456
                        mol_type = protein
                        organism = synthetic construct
SEQUENCE: 38
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APEFERGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFFLYSRL   420
TVDKSRWQQG NVFSCSVMHE ALHNHYTQKS LSLSPG                             456

SEQ ID NO: 39           moltype = AA  length = 577
FEATURE                 Location/Qualifiers
source                  1..577
                        mol_type = protein
                        organism = Homo sapiens
SEQUENCE: 39
FPQDRPFEDT CHGNPSHYYD KAVRRCCYRC PMGLFPTQQC PQRPTDCRKQ CEPDYYLDEA    60
DRCTACVTCS RDDLVEKTPC AWNSSRVCEC RPGMFCSTSA VNSCARCFFH SVCPAGMIVK   120
FPGTAQKNTV CEPASPGVSP ACASPENCKE PSSGTIPQAK PTPVSPATSS ASTMPVRGGT   180
RLAQEAASKL TRAPDSPSSV GRPSSDPGLS PTQPCPEGSG DCRKQCEPDY YLDEAGRCTA   240
CVSCSRDDLV EKTPCAWNSS RTCECRPGMI CATSATNSCA RCVPYPICAA ETVTKPQDMA   300
EKDTTFEAPP LGTQPDCNPT PENGEAPAST SPTQSLLVDS QASKTLPIPT SAPVALSSTG   360
KPVLDAGPVL FWVILVLVVV VGSSAFLLCH RRACRKRIRQ KLHLCYPVQT SQPKLELVDS   420
RPRRSSTQLR SGASVTEPVA EERGLMSQPL METCHSVGAA YLESLPLQDA SPAGGPSSPR   480
DLPEPRVSTE HTNNKIEKIY IMKADTVIVG TVKAELPEGR GLAGPAEPEL EEEELEADHTP   540
HYPEQETEPP LGSCSDVMLS VEEEGKEDPL PTAASGK                            577

SEQ ID NO: 40           moltype = AA  length = 487
FEATURE                 Location/Qualifiers
source                  1..487
                        mol_type = protein
                        organism = Macaca fascicularis
SEQUENCE: 40
FPQDRPFEDT CRGNPGHYYD KAVRRCCYRC PTGTAQKNTV CEPASPGVSP ACASPENCKE    60
PSSGTIPQAK PTPVSPATSN ASTMPLRGGT RLAQEAASKL TRAPGSPSSV GRPSSDPGLS   120
PTQPCPQGSG DCRKQCEPDY YLDEAGRCTA CVSCSRDDLV EKTPCAWNSS RICECRPGMI   180
CATSATNSCA RCVPYPICAA ETGTKPQDMA EKDTTFEAPP VGTQPDCSPT PENGEAPAST   240
SPTLSSLVDS QASKTLPIPT SAPIALSSTG KPVLDAGPVL FWVILVLAVV VGSSTFLLCH   300
RRACRKRIRQ KLHLCYPVQT SRPKLELVDS RPRRSSTQFE SGTFVTKPSA EELGLMSLPP   360
KETCRNVGAA CPESLPLWDA SPAGGPSSPR DLPEPRVSTE HTNRIEKIY IMKADTVIVG   420
TVKAELPEGQ GLAGPAEPEL EEEELEADHAP HYPEQETEPP LGSCSDVMLS VEEEGKEDPL   480
PTAASGK                                                             487

SEQ ID NO: 41           moltype = AA  length = 577
FEATURE                 Location/Qualifiers
source                  1..577
                        mol_type = protein
                        organism = Macaca mulatta
SEQUENCE: 41
FPQDRPFEDT CRGNPGHYYD KAVRRCCYRC PMGLFPTQQC PQRPADCRKQ CEPDYYLDEA    60
GRCTACVSCS RDDLVEKMPC AWNSSRVCEC QPGMFCAVSV VNSCARCFFH SVCPAGMIVK   120
FPGTAQKNTV CEPASPGVSP ACASPENCKE PSSGTIPQAK PTPVSPATSN ASTMPLRGGT   180
RLAQEAASKL TRAPGSPSSV GRPSSDPGLS PTQPCPQGSG DCRKQCEPDY YLDEAGRCTA   240
CVSCSRDDLV EKTPCAWNSS RICECRPGMI CATSATNSCA RCVPYPICAA ETGTKPQDMA   300
EKDTTFEAPP VGTQPDCSPT PENGEAPAST SPTLSSLVDS QASKTLPIPT SAPIALSSTG   360
KPVLDAGPVL FWVILVLAVV VGSSTFLLCH RRACRKRIRQ KLHLCYPVQT SRPKLELVDS   420
RPRRSSTQFE SGTFVTKPSA EELGLMSLPP KETCRNVGAA CPESLPLWDA SPAGGPSSPR   480
DLPEPRVSTE HTNNKIEKIY IMKADTVIVG TVKAELPEGQ GLAGPAEPEL EEEELEADHAP   540
HYPEQETEPP LGSCSDVMLS VEEEGKEDPL PTAASGK                            577

SEQ ID NO: 42           moltype = AA  length = 186
FEATURE                 Location/Qualifiers
source                  1..186
                        mol_type = protein
                        organism = Homo sapiens
SEQUENCE: 42
QDGNEEMGGI TQTPYKVSIS GTTVILTCPQ YPGSEILWQH NDKNIGGDED DKNIGSDEDH    60
LSLKEFSELE QSGYYVCYPR GSKPEDANFY LYLRARVCEN CMEMDVMSVA TIVIVDICIT   120
GGLLLLLVYYW SKNRKAKAKP VTRGAGAGGR QRGQNKERPP PVPNPDYEPI RKGQRDLYSG   180
LNQRRI                                                              186
```

```
SEQ ID NO: 43           moltype = AA   length = 177
FEATURE                 Location/Qualifiers
source                  1..177
                        mol_type = protein
                        organism = Macaca fascicularis
SEQUENCE: 43
QDGNEEMGSI TQTPYQVSIS GTTVILTCSQ HLGSEAQWQH NGKNKEDSGD RLFLPEFSEM    60
EQSGYYVCYP RGSNPEDASH HLYLKARVCE NCMEMDVMAV ATIVIVDICI TLGLLLLVYY   120
WSKNRKAKAK PVTRGAGAGG RQRGQNKERP PPVPNPDYEP IRKGQQDLYS GLNQRRI      177

SEQ ID NO: 44           moltype = AA   length = 329
FEATURE                 Location/Qualifiers
REGION                  1..329
                        note = Constant region
source                  1..329
                        mol_type = protein
                        organism = synthetic construct
SEQUENCE: 44
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 45           moltype = AA   length = 329
FEATURE                 Location/Qualifiers
REGION                  1..329
                        note = Constant region
source                  1..329
                        mol_type = protein
                        organism = synthetic construct
SEQUENCE: 45
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 46           moltype = AA   length = 329
FEATURE                 Location/Qualifiers
REGION                  1..329
                        note = Constant region
source                  1..329
                        mol_type = protein
                        organism = synthetic construct
SEQUENCE: 46
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFEGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 47           moltype = AA   length = 329
FEATURE                 Location/Qualifiers
REGION                  1..329
                        note = Constant region
source                  1..329
                        mol_type = protein
                        organism = synthetic construct
SEQUENCE: 47
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFLLY SKLTVDKSRW   300
QQGNVFSCSV MHEALHNHYT QKSLSLSPG                                    329

SEQ ID NO: 48           moltype = AA   length = 329
FEATURE                 Location/Qualifiers
REGION                  1..329
                        note = Constant region
source                  1..329
                        mol_type = protein
                        organism = synthetic construct
SEQUENCE: 48
```

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYCKVSNKA LPAPIEKTIS KAKGQPREPQ VYTLPPSREE   240
MTKNQVSLTC LVKGFYPSDI AVEWESNGQP ENNYKTTPPV LDSDGSFFLY SRLTVDKSRW   300
QQGNVFSCSV MHEALHNHYT QKSLSLSPG                                    329

SEQ ID NO: 49          moltype = AA  length = 329
FEATURE                Location/Qualifiers
REGION                 1..329
                       note = Constant region
source                 1..329
                       mol_type = protein
                       organism = synthetic construct
SEQUENCE: 49
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFERG   120
PSVFLFPPKP KDTLMISRTP EVTCVVVDVS HEDPEVKFNW YVDGVEVHNA KTKPREEQYN   180
STYRVVSVLT VLHQDWLNGK EYCKVSNKA LPAPIEKTIS KAKGQPREPQ VYTLPPSREE   240
MTKNQVSLTC LVKGFYPSDI AVEWESNGQP ENNYKTTPPV LDSDGSFLLY SKLTVDKSRW   300
QQGNVFSCSV MHEALHNHYT QKSLSLSPG                                    329

SEQ ID NO: 50          moltype = AA  length = 329
FEATURE                Location/Qualifiers
REGION                 1..329
                       note = Constant region
source                 1..329
                       mol_type = protein
                       organism = synthetic construct
SEQUENCE: 50
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFERG   120
PSVFLFPPKP KDTLMISRTP EVTCVVVDVS HEDPEVKFNW YVDGVEVHNA KTKPREEQYN   180
STYRVVSVLT VLHQDWLNGK EYCKVSNKA LPAPIEKTIS KAKGQPREPQ VYTLPPSREE   240
MTKNQVSLTC LVKGFYPSDI AVEWESNGQP ENNYKTTPPV LDSDGSFFLY SRLTVDKSRW   300
QQGNVFSCSV MHEALHNHYT QKSLSLSPG                                    329

SEQ ID NO: 51          moltype = AA  length = 329
FEATURE                Location/Qualifiers
REGION                 1..329
                       note = Constant region
source                 1..329
                       mol_type = protein
                       organism = synthetic construct
SEQUENCE: 51
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFEGG   120
PSVFLFPPKP KDTLMISRTP EVTCVVVAVS HEDPEVKFNW YVDGVEVHNA KTKPREEQYN   180
STYRVVSVLT VLHQDWLNGK EYCKVSNKA LPAPIEKTIS KAKGQPREPQ VYTLPPSREE   240
MTKNQVSLTC LVKGFYPSDI AVEWESNGQP ENNYKTTPPV LDSDGSFLLY SKLTVDKSRW   300
QQGNVFSCSV MHEALHNHYT QKSLSLSPG                                    329

SEQ ID NO: 52          moltype = AA  length = 329
FEATURE                Location/Qualifiers
REGION                 1..329
                       note = Constant region
source                 1..329
                       mol_type = protein
                       organism = synthetic construct
SEQUENCE: 52
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFEGG   120
PSVFLFPPKP KDTLMISRTP EVTCVVVAVS HEDPEVKFNW YVDGVEVHNA KTKPREEQYN   180
STYRVVSVLT VLHQDWLNGK EYCKVSNKA LPAPIEKTIS KAKGQPREPQ VYTLPPSREE   240
MTKNQVSLTC LVKGFYPSDI AVEWESNGQP ENNYKTTPPV LDSDGSFFLY SRLTVDKSRW   300
QQGNVFSCSV MHEALHNHYT QKSLSLSPG                                    329

SEQ ID NO: 53          moltype = AA  length = 107
FEATURE                Location/Qualifiers
REGION                 1..107
                       note = Light chain
source                 1..107
                       mol_type = protein
                       organism = synthetic construct
SEQUENCE: 53
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 54          moltype = AA  length = 106
```

```
FEATURE                 Location/Qualifiers
REGION                  1..106
                        note = Light chain
source                  1..106
                        mol_type = protein
                        organism = synthetic construct
SEQUENCE: 54
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 55           moltype = AA  length = 441
FEATURE                 Location/Qualifiers
REGION                  1..441
                        note = Heavy chain
source                  1..441
                        mol_type = protein
                        organism = synthetic construct
SEQUENCE: 55
QVQLQQWGAG LLKPSETLSL TCAVYGGSFS AYYWSWIRQP PGKGLEWIGD INHGGGTNYN    60
PSLKSRVTIS VDTSKNQFSL KLNSVTAADT AVYYCASLTA YWGQGSLVTV SSASTKGPSV    120
FPLAPSSKST SGGTAALGCL VKDYFPEPVT VSWNSGALTS GVHTFPAVLQ SSGLYSLSSV    180
VTVPSSSLGT QTYICNVNHK PSNTKVDKRV EPKSCDKTHT CPPCPAPEFE GGPSVFLFPP    240
KPKDTLMISR TPEVTCVVVA VSHEDPEVKF NWYVDGVEVH NAKTKPREEQ YNSTYRVVSV    300
LTVLHQDWLN GKEYKCKVSN KALPAPIEKT ISKAKGQPRE PQVYTLPPSR EEMTKNQVSL    360
TCLVKGFYPS DIAVEWESNG QPENNYKTTP PVLDSDGSFF LYSRLTVDKS RWQQGNVFSC    420
SVMHEALHNH YTQKSLSLSP G                                             441
```

ANTIBODIES BINDING TO CD30 AND CD3

CROSS-REFERENCE TO RELATED APPLICATIONS

This application claims priority to European Application No. EP 21201712.3, filed Oct. 8, 2021. The contents of the aforementioned application is hereby incorporated by reference.

SEQUENCE LISTING

The instant application contains a Sequence Listing which has been submitted electronically in XML format and is hereby incorporated by reference in its entirety. Said XML copy, created on Nov. 17, 2022, is named GMI-215_SequenceListing_2022-11-17.xml and is 77 kilobytes in size.

FIELD OF THE INVENTION

The present invention relates to multispecific antibodies binding to CD30 and CD3. The invention further provides pharmaceutical compositions comprising the antibodies, nucleic acids encoding the antibodies, host cells that produce the antibodies, methods of producing the antibodies and uses of the antibodies, in particular for cancer therapy.

BACKGROUND OF THE INVENTION

CD30, also known as Ki-1 or TNFRSF8, is a 120 kD transmembrane glycoprotein receptor and is a member of the tumor necrosis factor receptor (TNFR) superfamily (Smith et al. (1994) Cell 76: 959-962). CD30 is a single-pass type I membrane protein with six cysteine-rich repeats in its extracellular domain (Durkop et al. (1992) Cell 68: 421-427). In addition, a soluble form of CD30 (sCD30) has been detected in the serum of patients with inflammatory diseases, including ulcerative colitis (UC) (Giacomelli et al. Clin Exp Immunol. 1998; 111:532-5), and CD30-positive hematologic malignancies (Josimovic-Alasevic et al. (1989) Eur J Immunol). sCD30 represents the cleavage product of the extracellular portion of CD30 by cell membrane-anchored metalloproteinases such as TACE/ADAM17 and ADAM10 (Nagata et al., PNAS 2005; Hansen et al., FASEB, 2004).

In normal tissues CD30 expression is mainly restricted to subsets of activated T and B lymphocytes (Bowen et al. (1996) J Immunol. 156:442-9; Shanebeck et al. (1995) Eur J Immunol. 25:2147-53). CD30 expression has been detected in a variety of lymphoid neoplasms. Classical Hodgkin lymphoma (cHL) and anaplastic large cell lymphoma (ALCL) show high CD30 expression levels. In particular, the large majority of Reed-Sternberg (RS) cells, which are typically found in cHL, are positive for CD30 (Frizzera et al. (1992) Semin. Diagn. Pathol. 9: 291-296).

For example, the CD30-targeting antibody-drug conjugate brentuximab vedotin (BV; SGN-35) has been used for or suggested for use in treating cancers such as cHL, ALCL and CTCL (Younes et al. J Clin Oncol. 2012 Jun. 20; 30(18):2183-9; Pro et al. Blood. 2017 Dec. 21; 130(25): 2709-2717; Shea et al. Curr Hematol Malig Rep. 2020 February; 15(1):9-19). The tetravalent bispecific CD30× CD16A antibody AFM13 is being developed as NK cell-mediated immunotherapy for cHL and CD30-positive lymphoma (Rothe et al. Blood. 2015 Jun. 25; 125(26):4024-31).

Furthermore, CD30-targeting CAR-T cell therapies are being developed for cHL and CD30-positive lymphoma.

Other CD30 antibodies have been described in WO2003059282 (Medarex), U.S. Pat. No. 8,257,706 (Seattle genetics), US20100239571 (Seattle genetics) WO2007040653 (US government & Health), and WO20160177846 (Affimed).

Pohl et al. (1993 Int. J. Cancer, 54: 820-827) describe the CD3×CD30 bispecific antibody OKT-3/HRS-3 that was generated by fusion of the CD30 monoclonal antibody HRS-3-producing hybridoma cells with CD3 monoclonal antibody OKT-3-producing hybridoma cells (hybrid hybridoma technology).

WO2008119567 describes the generation and characterization of CD30 and CD3 cross-species specific bispecific single chain molecules.

US20200095330 describes CD3×CD30 bispecific antibodies resulting from the chemical heteroconjugation of two anti-CD30 clones (named 8D10 and 10C2) to anti-CD3 (Orthoclone OKT-3).

However, none of these CD3×CD30 bispecific antibodies have been tested in a clinical setting.

There is therefore a need for improved CD30-targeting cancer therapy. There is a need for CD30 targeting compounds that are efficacious, safe, have good manufacturability and/or have a long shelf-life.

SUMMARY OF THE INVENTION

The present invention relates to T-cell engaging antibodies that bind human and cynomolgus monkey CD30 and CD3. The inventors have found that some CD30 binding antibodies bind well to CD30-expressing cells in a bivalent (monoclonal) format but exhibit strongly reduced binding and cytotoxicity in a bispecific format with monovalent CD30 binding. Bispecific antibodies having strong monovalent CD30 binding as well as excellent tumor cell killing were identified.

Furthermore, a bispecific antibody with a functionally inactive Fc backbone was identified which is suitable for development into a pharmaceutical product, because of excellent stability and solubility.

(i) a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively, and (ii) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively.

In a further aspect, the invention relates to a nucleic acid construct, or a combination of nucleic acid constructs, encoding a multispecific antibody according to the invention.

In further aspects, the invention relates to an expression vector or a delivery vehicle comprising a nucleic acid construct(s) according to the invention.

In a further aspect, the invention relates to a recombinant host cell capable of producing the multispecific antibody according to the invention, wherein the host cell comprises one or more nucleic acid constructs encoding the multispecific antibody according to the invention.

In a further aspect, the invention relates to a pharmaceutical composition comprising a multispecific antibody according to the invention and a pharmaceutically-acceptable carrier.

In further aspects, the invention relates to multispecific antibody, the nucleic acid constructs, the delivery vehicle or the pharmaceutical composition according to the invention for use as a medicament, for example in the treatment of cancer.

In even further aspects, the invention relates to methods for producing multispecific antibodies according to the invention.

DESCRIPTION OF THE FIGURES

FIGS. 1A-1I: Binding of bispecific CD3×CD30 antibodies and their monospecific, bivalent CD3 and CD30 counterparts to SU-DHL-1 or HDML-2 cells. Dose-dependent binding of (FIG. 1A) bsG1-huCD3-FEAL×CD30-MDX060-FEAR, bsG1-huCD3-FEAL×b12-FEAR, bsG1-b12-FEAL×CD30-MDX060-FEAR, and IgG1-CD30-MDX060-FEAR, (FIG. 1B) bsG1-huCD3-FEAL×CD30-hAC10-FEAR, bsG1-huCD3-FEAL×b12-FEAR, and IgG1-CD30-hAC10-FEAR, (FIG. 1C) bsG1-huCD3-FEAL×CD30-HRS-3-FEAR, bsG1-huCD3-FEAL×b12-FEAR, and IgG1-CD30-HRS-3-FEAR, (FIG. 1D) BsIgG1-huCD3-FEAL×CD30-HeFi-I-FEAR, bsG1-huCD3-FEAL×b12-FEAR, and IgG1-CD30-HeFi-I-FEAR, (FIG. 1E) bsIgG1-huCD3-FEAL×CD30-T405-FEAR, bsG1-huCD3-FEAL×b12-FEAR, and IgG1-CD30-T405-FEAR, (FIG. 1F) bsIgG1-huCD3-FEAL×CD30-T105-FEAR, bsG1-huCD3-FEAL×b12-FEAR, and IgG1-CD30-T105-FEAR, (FIG. 1G) bsIgG1-huCD3-FEAL×CD30-T408-FEAR, bsG1-huCD3-FEAL×b12-FEAR, and IgG1-CD30-T408-FEAR, and (FIG. 1H) bsIgG1-huCD3-FEAL×CD30-T215-FEAR, bsG1-huCD3-FEAL×b12-FEAR, and IgG1-CD30-HRS-3-FEAR to SU-DHL-1 cells (left panels) or HDLM-2 cells (right panels). (FIG. 1I) Binding of CD3×CD30 bispecific antibodies and CD30 monospecific antibodies to SU-DHL-1 (left panels) or HDLM-2 cells (right panels) at a concentration of 1.11 μg/mL. The antibody clones used for the CD30 arm are indicated on the x-axis. Data shown are mean fluorescence intensity (MFI) values as determined by flow cytometry, for one representative experiment.

FIGS. 2A-2D: Binding of bsG1-huCD3×CD30-MDX060 to HL and ALCL cell lines. Binding of bsG1-huCD3×CD30-MDX060 to (FIG. 2A) HDLM-2 (HL), (FIG. 2B) L-428 (HL), (FIG. 2C) DEL (ALCL), or (FIG. 2D) KI-JK (ALCL) cells was evaluated by flow cytometry. Bispecific antibodies bsG1-huCD3×b12 and bsG1-b12×CD30-MDX060 and monospecific antibodies IgG1-CD30-MDX060, IgG1-huCD3 and IgG1-12 were included as controls. All antibodies contained the FEAL and/or FERR Fc silencing and DuoBody® technology mutations in their Fc domain as indicated. Data shown are mean fluorescence intensity (MFI) values as determined by flow cytometry, for one representative experiment.

FIGS. 3A-3H: Induction of cytotoxicity in vitro by CD3×CD30 bispecific antibodies in SU-DHL-1 or HDML-2 cells. CD3×CD30 bispecific antibodies were tested in an in vitro cytotoxicity assay using the CD30-positive tumor cell lines SU-DHL-1 cells (left panels) or HDLM-2 cells (right panels) as target cells and T cells (CD3-positive ADCC effector cells type IV cells; Clean Cells, Montaigu, France) as effector cells. The following antibodies were tested: (FIG. 3A) bsG1-huCD3-FEAL×CD30-MDX060-FEAR, bsG1-b12-FEAL×CD30-MDX060-FEAR, and IgG1-CD30-MDX060-FEAR, (FIG. 3B) bsG1-huCD3-FEAL×CD30-hAC10-FEAR and IgG1-CD30-hAC10-FEAR, (FIG. 3C) bsG1-huCD3-FEAL×CD30-HRS-3-FEAR and IgG1-CD30-HRS-3-FEAR, (FIG. 3D) BsIgG1-huCD3-FEAL×CD30-HeFi-I-FEAR and IgG1-CD30-HeFi-I-FEAR, (FIG. 3E) bsIgG1-huCD3-FEAL×CD30-T405-FEAR and IgG1-CD30-T405-FEAR, (FIG. 3F) bsIgG1-huCD3-FEAL×CD30-T105-FEAR and IgG1-CD30-T105-FEAR, (FIG. 3G) bsIgG1-huCD3-FEAL×CD30-T408-FEAR and IgG1-CD30-T408-FEAR, or (FIG. 3H) bsIgG1-huCD3-FEAL×CD30-T215-FEAR and IgG1-CD30-HRS-3-FEAR. The antibody bsG1-huCD3-FEAL×b12-FEAR was included as control in all experiments. Data shown are percentages viable cells; data for each graph were obtained from one representative experiment.

FIGS. 4A-4D: Induction of T-cell mediated cytotoxicity and T-cell proliferation in vitro by CD3×CD30 bispecific antibodies in several ALCL and HL cell lines. (FIGS. 4A-4C) CD3×CD30 bispecific antibodies were tested in an in vitro cytotoxicity assay using different ALCL and HL cell lines as target cells and purified T cells (FIG. 4A and FIG. 4B) or ADCC effector cells type IV cells (FIG. 4C) or as effector cells. CD3×CD30 bispecific antibodies contained the huCD3-FEAL Fab arm or the huCD3-H101G-FEAL variant, which has lower affinity for CD3, and the CD30-specific MDX060-FEAR Fab arm. IgG1-huCD3 and IgG1-b12 (FIG. 4A and FIG. 4B) or bsG1-b12-FEAL×CD30-MDX060-FEAR and IgG1-CD30-MDX060-FEAR (FIG. 4C) were included as controls. Data shown are percentages viable cells; data for each graph were obtained from one representative experiment. (FIG. 4D) The number of CFSE-positive cells was evaluated as a measure of absolute T-cell counts in the cytotoxicity assays using HDLM-2 cells (left panel) or NCEB-1 cells (right panel) as target cells.

(FIGS. 5A-5C) Binding of monovalent and bivalent CD30 antibodies to wild-type Expi293F cells (FIG. 5A) or Expi293F cells transiently transfected with full length human CD30 (FIG. 5B) or cynomolgus monkey CD30 (FIG. 5C). Cells were incubated with increasing concentrations of the following antibodies: IgG1-CD30-MDX060-FEAR, bsG1-huCD3-FEAL×CD30-MDX060-FEAR, bsG1-huCD3-H101G-FEAL×CD30-MDX060-FEAR, bsG1-b12-FEAL×CD30-MDX060-FEAR, and bsG1-huCD3-FEAL×b12-FEAR. Data are presented as mean fluorescence intensity (MFI) values as determined by flow cytometry of two technical replicates. (FIG. 5D) Binding of antibodies IgG1-CD30-MDX060-FEAR, bsG1-huCD3-FEAL×CD30-MDX060-FEAR, and bsG1-huCD3-FEAL×b12-FEAR to human T cells or cynomolgus monkey T cells. Data are presented as mean fluorescence intensity (MFI) values as determined by flow cytometry of one representative experiment.

FIGS. 6A-6H: Binding of CD3×CD30 bispecific antibodies to full length human and rhesus monkey CD30 transfected into Expi293F cells. Binding of monovalent and bivalent CD30 antibodies to Expi293F cells transiently transfected with full length human CD30 (left panels) or rhesus monkey CD30 (right panels) was evaluated by flow cytometry. The following antibodies were evaluated: (FIG. 6A) bsG1-huCD3-FEAL×CD30-hAC10-FEAR and IgG1-CD30-hAC10-FEAR, (FIG. 6C) bsG1-huCD3-FEAL×CD30-HRS-3-FEAR and IgG1-CD30-HRS-3-FEAR, (FIG. 6D) bsIgG1-huCD3-FEAL×CD30-HeFi-I-FEAR and IgG1-CD30-HeFi-I-FEAR, (FIG. 6E) bsIgG1-huCD3-FEAL×CD30-T405-FEAR and IgG1-CD30-T405-FEAR, (FIG. 6F)

Figure 6C:
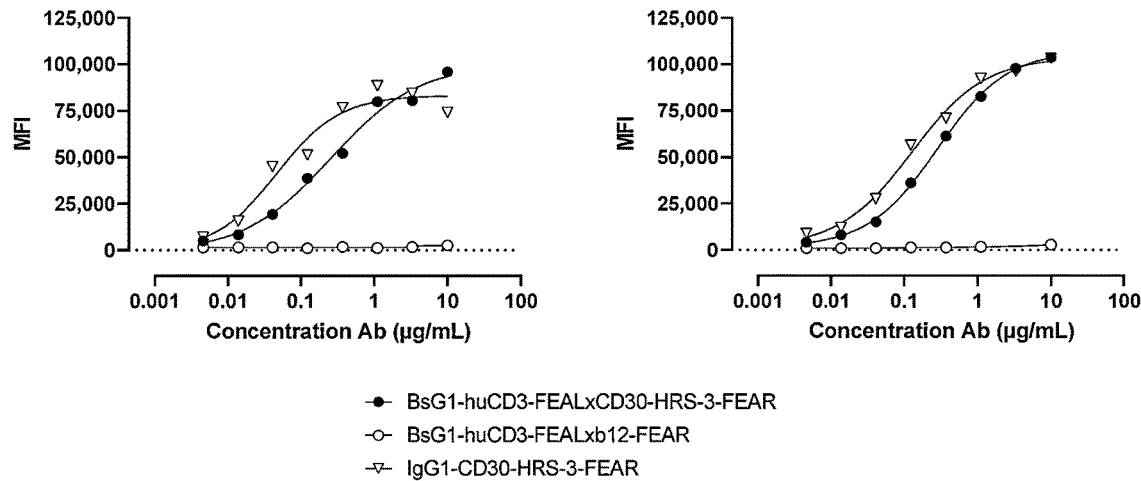

bsIgG1-huCD3-FEALxCD30-T105-FEAR and IgG1-CD30-T105-FEAR, (FIG. 6G) bsIgG1-huCD3-FEALx CD30-T408-FEAR and IgG1-CD30-T408-FEAR, or (FIG. 6H) bsIgG1-huCD3-FEALxCD30-T215-FEAR and IgG1-CD30-HRS-3-FEAR. The antibody bsG1-huCD3-FEALx b12-FEAR was included as a negative control in all experiments. Data shown are mean fluorescence intensity (MFI) values as determined by flow cytometry, for one representative experiment.

FIGS. 7A-7D: Thermostability of antibodies with different non-activating mutations as determined by differential scanning fluorimetry (DSF). Conformational protein stability at increasing temperatures was evaluated in duplicate by DSF. Melting curves of the following antibodies are shown: (FIG. 7A) IgG1-CD30-MDX060-FEAR at pH 7.4, (FIG. 7B) IgG1-CD30-MDX060-FERR at pH 7.4, (FIG. 7C) IgG1-huCD3-FEAL at pH 7.4, and (FIG. 7D) BsG1-huCD3-FEALxCD30-MDX060-FERR at pH 7.4.

Figure 8A:
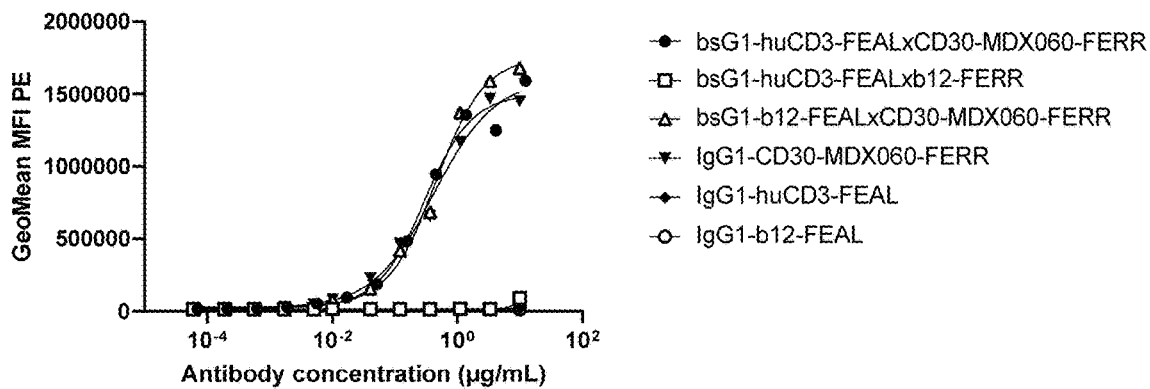
Figure 8B:
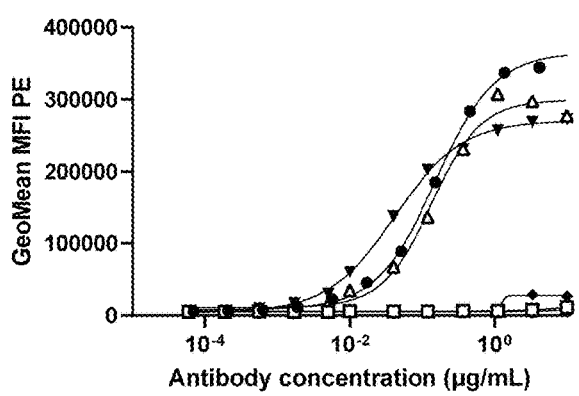
Figure 8C:
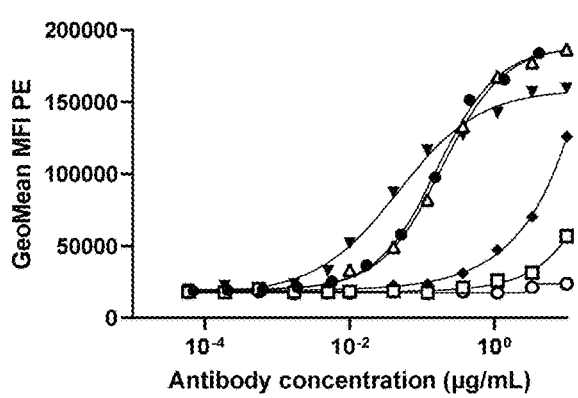

FIGS. 8A-8C: Binding of bsG1-huCD3-FEALxCD30-MDX060-FERR to HL cell lines. Binding of bsG1-huCD3-FEALxCD30-MDX060-FERR to HL cell lines L-540 (FIG. 8A), KM-H2 (FIG. 8B), and L-1236 (FIG. 8C) was evaluated by flow cytometry. Bispecific antibodies bsG1-huCD3-FEALxb12-FERR and bsG1-b12-FEALxCD30-MDX060-FERR and monospecific antibodies IgG1-CD30-MDX060-FERR, IgG1-huCD3-FEAL and IgG1-12-FEAL were included as controls. Data shown are mean fluorescence intensity (MFI) values as determined by flow cytometry, for one representative experiment.

FIGS. 9A-9E: Binding of bsG1-huCD3-FEALxCD30-MDX060-FERR to ALCL cell lines. Binding of bsG1-huCD3-FEALxCD30-MDX060-FERR to ALCL cell lines SUP-M2 (FIG. 9A), DL-40 (FIG. 9B), KARPAS-299 (FIG. 9C), L-82 (FIG. 9D), and SR-786 (FIG. 9E) was evaluated by flow cytometry. Bispecific antibodies bsG1-huCD3-FEALxb12-FERR and bsG1-b12-FEALxCD30-MDX060-FERR and monospecific antibodies IgG1-CD30-MDX060-FERR, IgG1-huCD3-FEAL and IgG1-12-FEAL were included as controls. Data shown are mean fluorescence intensity (MFI) values as determined by flow cytometry, for one representative experiment.

FIGS. 10A-10D: Binding of bsG1-huCD3-FEALxCD30-MDX060-FERR to NHL cell lines. Binding of bsG1-huCD3-FEALxCD30-MDX060-FERR to (FIG. 10A) SUP-T1 (TLL), (FIG. 10B) JVM-2 (MCL), (FIG. 10C) HH (CTCL), and (FIG. 10D) NCEB-1 (MCL) cell lines was evaluated by flow cytometry. Bispecific antibodies bsG1-huCD3-FEALxb12-FERR and bsG1-b12-FEALxCD30-MDX060-FERR and monospecific antibodies IgG1-CD30-MDX060-FERR, IgG1-huCD3-FEAL and IgG1-12-FEAL were included as controls. Data shown are mean fluorescence intensity (MFI) values as determined by flow cytometry, for one representative experiment.

Figure 11A:
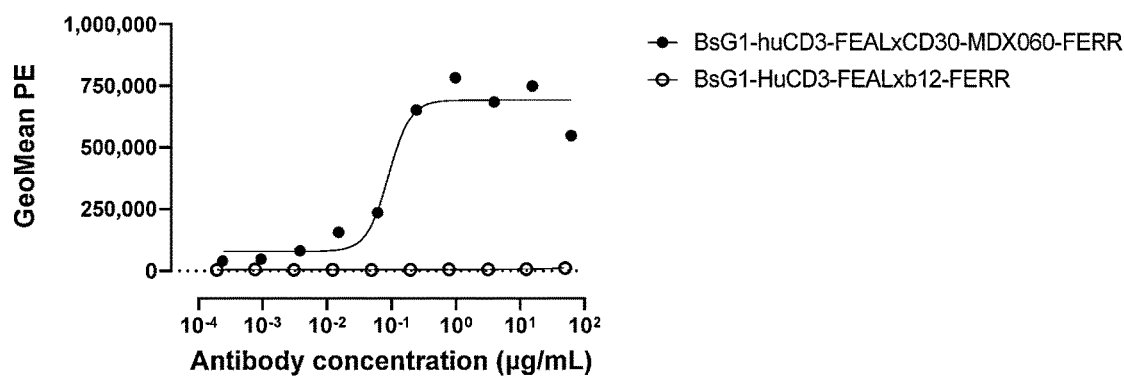
Figure 11B:
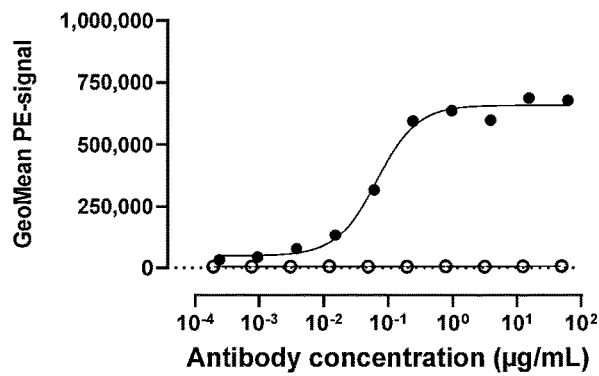

FIGS. 11A and 11B: Binding of bsG1-huCD3-FEALx CD30-MDX060-FERR to full length human and rhesus monkey CD30 transfected into HEK293 cells. Binding of bsG1-huCD3-FEALxCD30-MDX060-FERR to HEK293 cells transiently transfected with full length human CD30 (FIG. 11A) or rhesus monkey CD30 (FIG. 11B) was evaluated by flow cytometry. bsG1-huCD3-FEALxb12-FERR was included as a negative control. Data shown are mean fluorescence intensity (MFI) values as determined by flow cytometry, for one representative experiment.

Figure 12A:
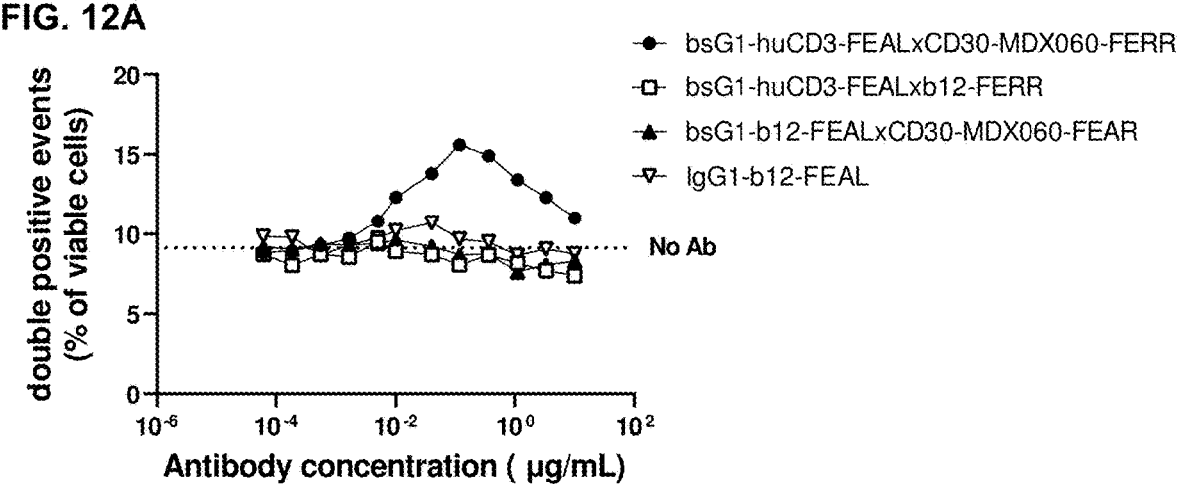
Figure 12B:
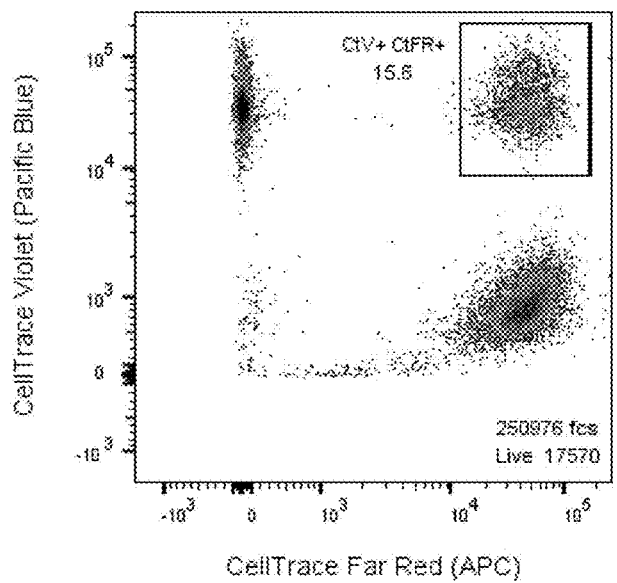

FIGS. 12A and 12B: Simultaneous binding of bsG1-huCD3-FEALxCD30-MDX060-FERR to T cells and tumor cells. Simultaneous binding of bsG1-huCD3-FEALxCD30-MDX060-FERR to fluorescently labelled tumor cells and naive T cells was studied by flow cytometry. (FIG. 12A) Double-positive events are shown as percentage of total viable cells in the presence of $6 \times 10^{-5}$ to 10 μg/mL bsG1huCD3FEALxCD30-MDX060-FERR or control antibodies bsG1-huCD3-FEALxb12-FEAR, bsG1b12FEALx CD30MDX060-FERR, or IgG1-b12-FEAL. The percentage of double-positive events in samples incubated without antibody are indicated with the dotted line. (FIG. 12B) Example of the gating strategy of double positive cells in samples incubated with 0.12 μg/mL bsG1huCD3FEALx CD30-MDX060-FERR.

FIGS. 13A-13F: Induction of T-cell mediated cytotoxicity and T-cell activation in vitro by CD3xCD30 bispecific antibodies.

A panel of CD3xCD30 bispecific antibodies were tested in an in vitro cytotoxicity assay using the CD30-positive tumor cell line Karpas-299 as target cells and T cells purified from healthy human donor buffy coats as effector cells. In these assay CD25 expression was evaluated in CD4+ and CD8+ cells as a measure for T-cell activation. The following antibodies were tested: bsG1-huCD3-FEALxCD30-MDX060-FERR, bsG1-huCD3-FEALxCD30-MDX060-FEAR, bsG1-huCD3-FEALxCD30-hAC10-FEAR, bsG1-huCD3-FEALxCD30-HRS-3-FEAR, BsG1-huCD3-FEALxCD30-HeFi-I-FEAR, bsIgG1-huCD3-FEALx CD30-T105-FEAR, bsIgG1-huCD3-FEALxCD30-T405-FEAR, bsIgG1-huCD3-FEALxCD30-T408-FEAR, and bsIgG1-huCD3-FEALxCD30-T215-FEAR. (FIG. 13A) $IC_{50}$ values for cytotoxicity of Karpas-299 cells by CD3x CD30 antibodies. (FIG. 13B) Percentage of maximum cytotoxicity of Karpas-299 cells by test antibodies. (FIGS. 13C-13F) $EC_{50}$ values for induction of CD25 (FIGS. 13C and 13D) or PD-1 (FIGS. 13E and 13F) expression in CD4+(FIGS. 13C and 13E) or CD8+(FIGS. 13D and 13F) T cells by CD3xCD30 antibodies. Data were obtained from two independent experiments that were performed with T cells obtained from 6 different donors. Statistical values represent the result of a Wilcoxon matched-pairs singed rank test between the indicated clone and bsG1-huCD3-FEALx CD30-MDX060-FERR. NS: Nonsignificant, *: p<0.05.

FIGS. 14A-14D: T-cell mediated cytotoxicity of cell lines in vitro by bsG1-huCD3-FEALxCD30-MDX060-FERR. Dose-dependent T-cell mediated cytotoxicity by bsG1-huCD3-FEALxCD30-MDX060-FERR was tested in vitro using L-428 (FIG. 14A), KM-H2 (FIG. 14B), SUP-M2 (FIG. 14C), or KI-JK (FIG. 14D) tumor cell lines as target cells and purified T cells as effector cells. IgG1-huCD3-FEAL, bsG1-huCD3-FEALxb12-FERR, IgG1-CD30-MDX060-FERR, bsG1-b12-FEALxCD30-MDX060-FERR, and IgG1-b12-FEAL were included as controls. Data shown are percentages viable cells, data for each graph were obtained for one representative experiment.

FIGS. 15A-15D: T-cell proliferation in vitro by bsG1-huCD3-FEALxCD30-MDX060-FERR in L-428 and KI-JK cell lines. T-cell proliferation was evaluated in T-cell mediated cytotoxicity assays using L-428 (FIGS. 15A and 15B) or KI-JK (FIGS. 15C and 15D) as target cells. CD4$^+$ (FIGS. 15A and 15C) or CD8$^+$ (FIGS. 15B and 15D) T cells with diluted Celltrace Violet staining were gated and the expansion index, as a measure for T-cell proliferation, was calculated using the proliferation modeling tool from FlowJo.

FIGS. 16A-16D: Expression of T-cell activation marker CD69 in vitro by bsG1-huCD3-FEALxCD30-MDX060-FERR in L-428 and KI-JK cell lines. T-cell activation was evaluated in T-cell mediated cytotoxicity assays using L-428 (FIGS. 16A and 16B) or KI-JK (FIGS. 16C and 16D) as target cells. The expression of the T-cell activation marker CD69 was evaluated in CD4$^+$ (FIGS. 16A and 16C) or CD8$^+$ (FIGS. 16B and 16D) T cells.

FIGS. 17A-17D: Expression of T-cell activation marker CD25 in vitro by bsG1-huCD3-FEALxCD30-MDX060-FERR in L-428 and KI-JK cell lines. T-cell activation was evaluated in T-cell mediated cytotoxicity assays using L-428 (FIGS. 17A and 17B) or KI-JK (FIGS. 17C and 17D) as target cells. The expression of the T-cell activation marker CD25 was evaluated in CD4$^+$ (FIGS. 17A and 17C) or CD8$^+$ (FIGS. 17B and 17D) T cells.

FIGS. 18A-18D: Expression of T-cell activation marker PD-1 in vitro by bsG1-huCD3-FEALxCD30-MDX060-FERR in L-428 and KI-JK cell lines. T-cell activation was evaluated in T-cell mediated cytotoxicity assays using L-428 (FIGS. 18A and 18B) or KI-JK (FIGS. 18C and 18D) as target cells. The expression of the T-cell activation marker PD-1 was evaluated in CD4$^+$ (FIGS. 18A and 18C) or CD8$^+$ (FIGS. 18B and 18D) T cells.

Figure 19:
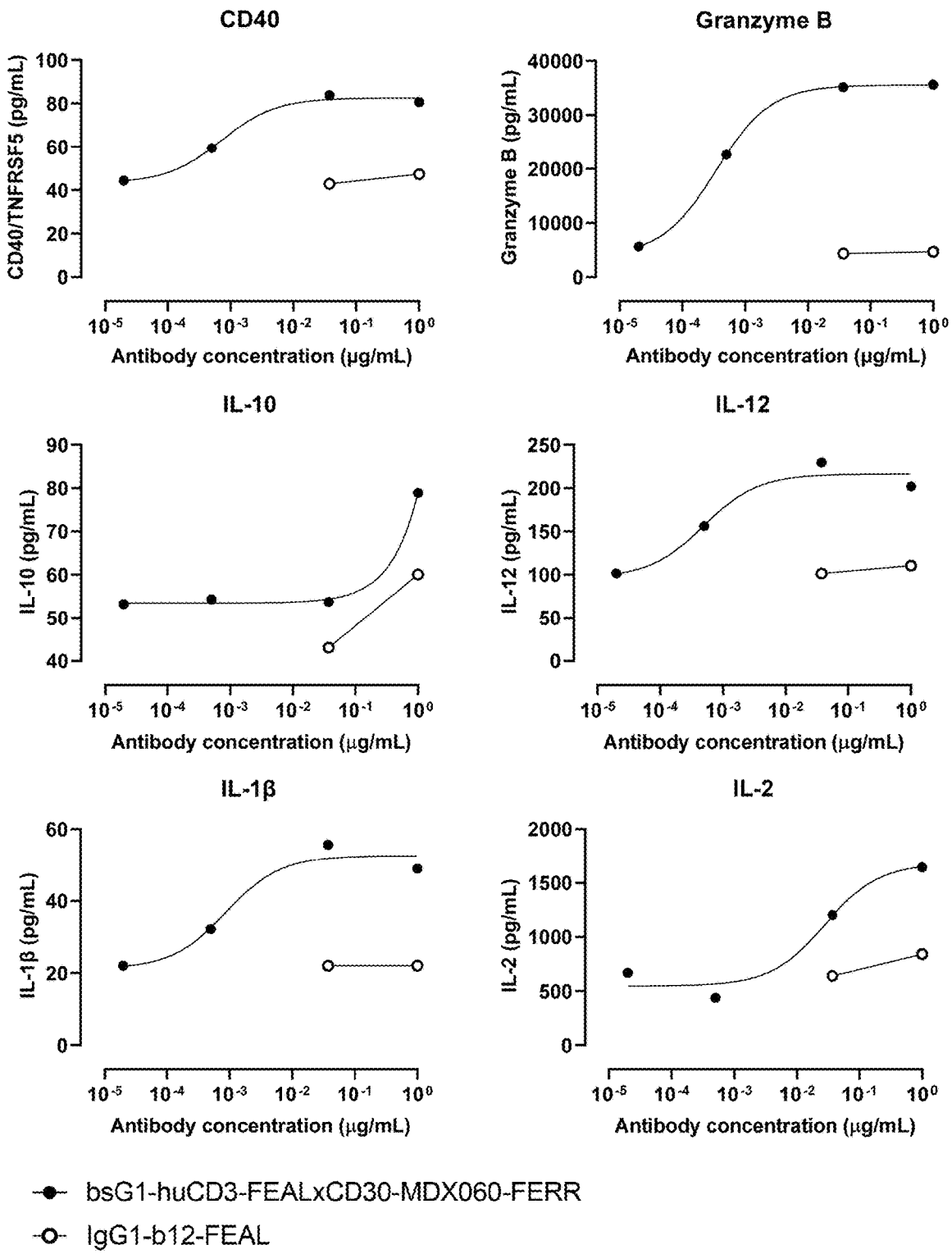
Figure 19:
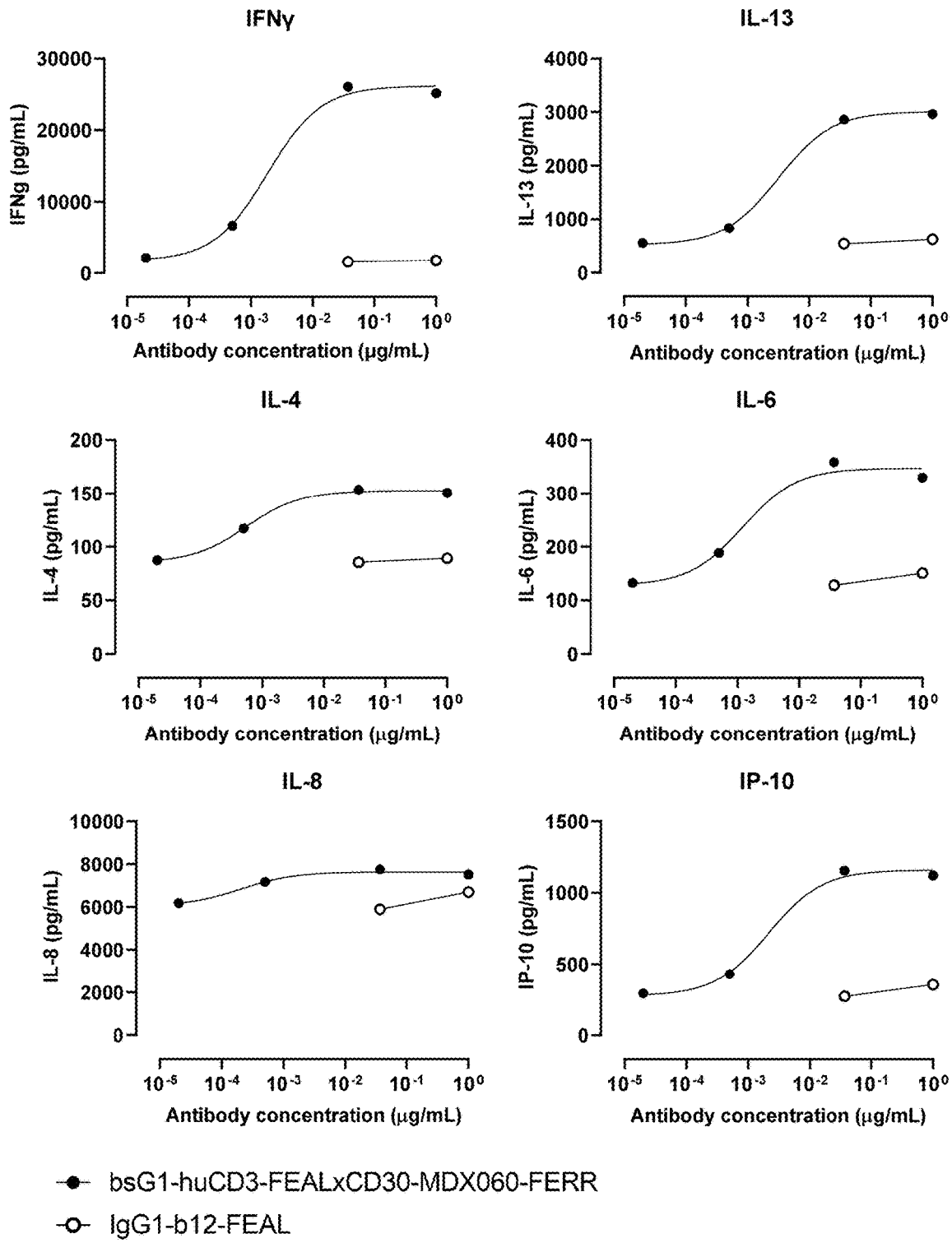
Figure 19:
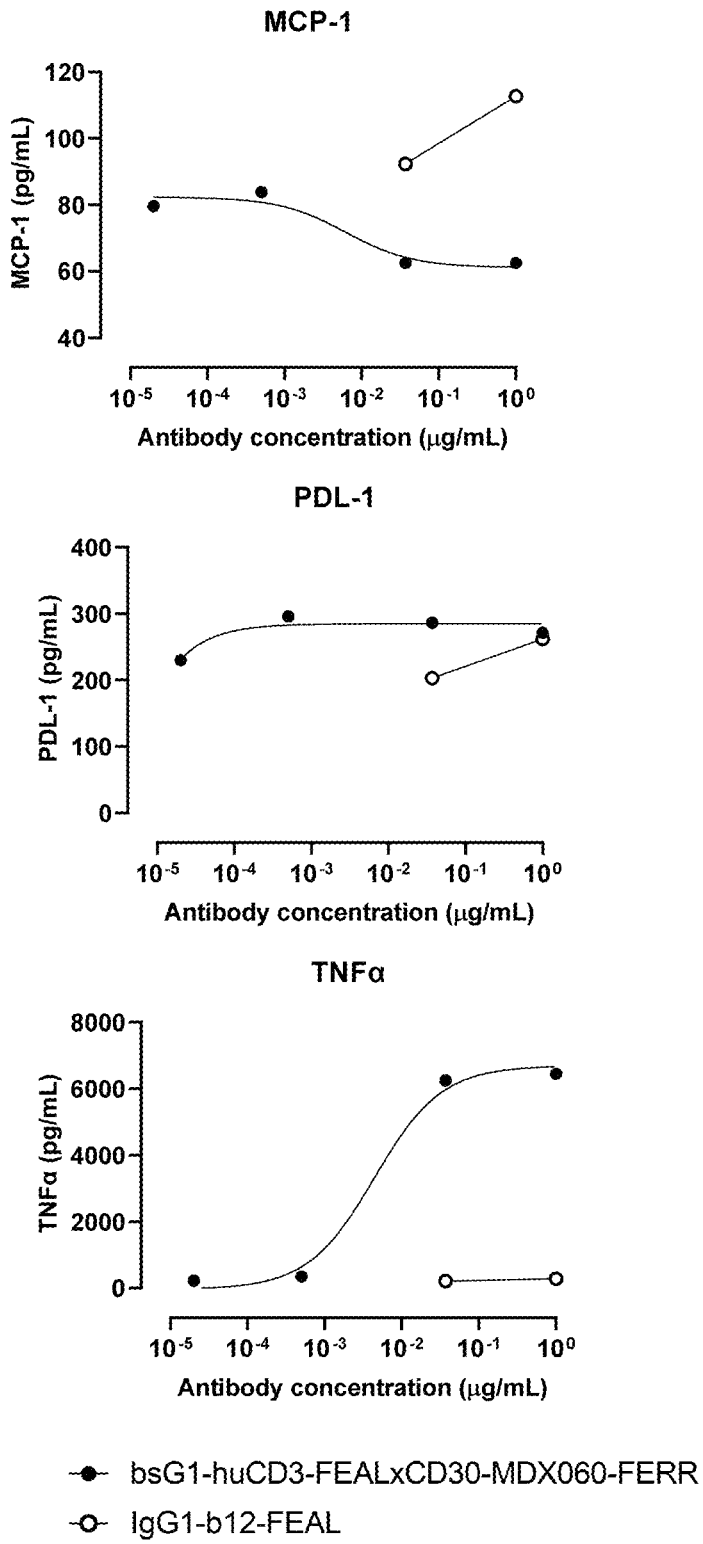

FIG. 19: Cytokine and Granzyme B production in vitro by bsG1-huCD3-FEALxCD30-MDX060-FERR. The concentration of 14 different cytokines (CD40, IFNγ, IL-10, IL-12, IL-13, IL-1b, IL-2, IL-4, IL-6, IL-8, IP-10, MCP-1, PDL-1, TNFα) and Granzyme B was evaluated in supernatants that were collected during in vitro T cell-mediated cytotoxicity experiments using L-428 as target cells. Cytokine and Granzyme B concentrations are shown for samples treated with different concentrations of bsG1-huCD3-FEALxCD30-MDX060-FERR or control antibody IgG1-b12-FEAL.

Figure 20A:
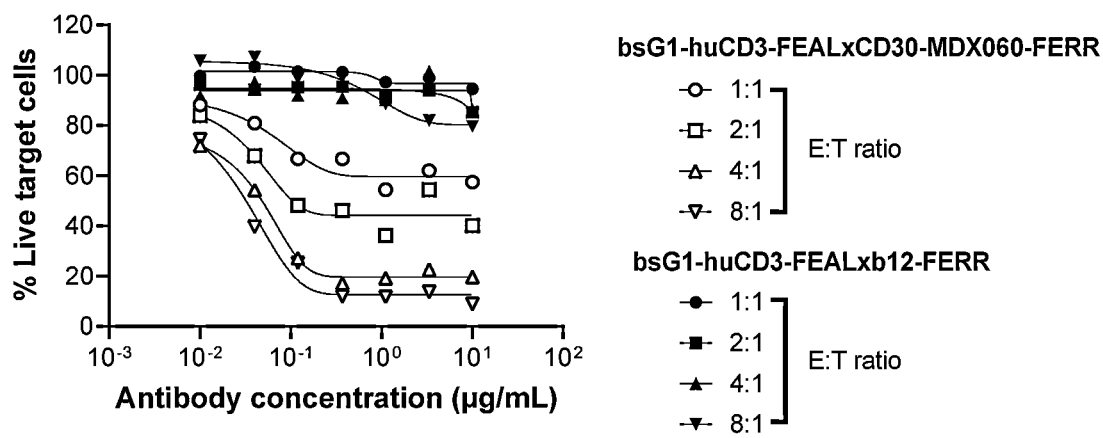
Figure 20B:
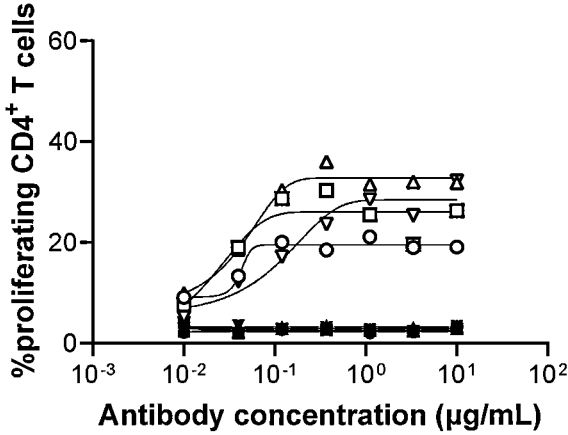
Figure 20C:
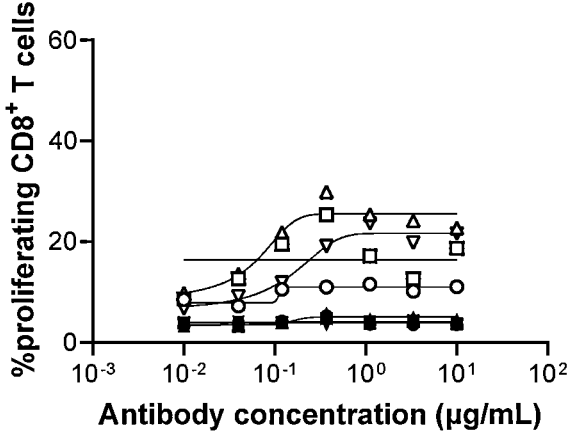

FIGS. 20A-20C: T-cell mediated cytotoxicity and T-cell proliferation in vitro by bsG1-huCD3-FEALxCD30-MDX060-FERR at varying effector to target ratios. (FIG. 20A) Dose-dependent T-cell mediated cytotoxicity by bsG1-huCD3-FEALxCD30-MDX060-FERR was tested in vitro using L-428 tumor cells as target cells and purified T cells as effector cells at E:T ratios of 1:1, 2:1, 4:1 or 8:1. bsG1-huCD3-FEALxb12-FERR was included as control antibody. Data shown are percentages viable cells, obtained from one representative experiment. (FIGS. 20B and 20C) The percentage of CD4$^+$ (FIG. 20B) or CD8$^+$ (FIG. 20C) T cells with diluted Celltrace Violet staining is shown as a measure of proliferating T cells.

Figure 21A:
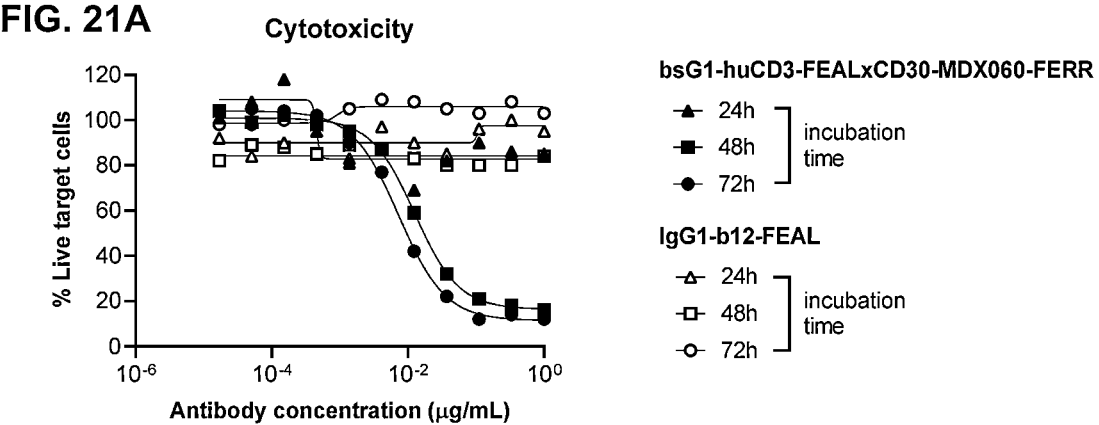
Figure 21B:
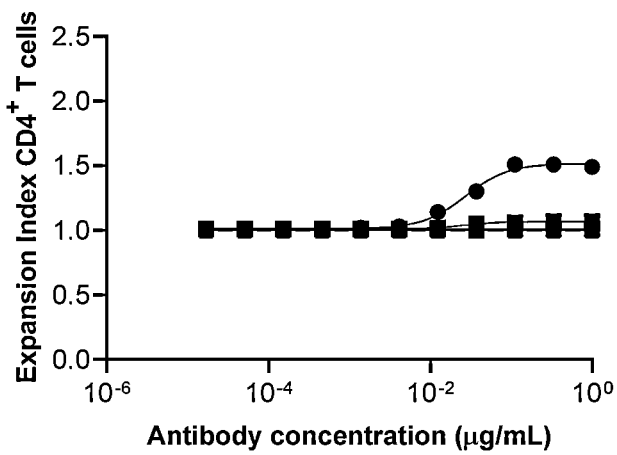
Figure 21C:
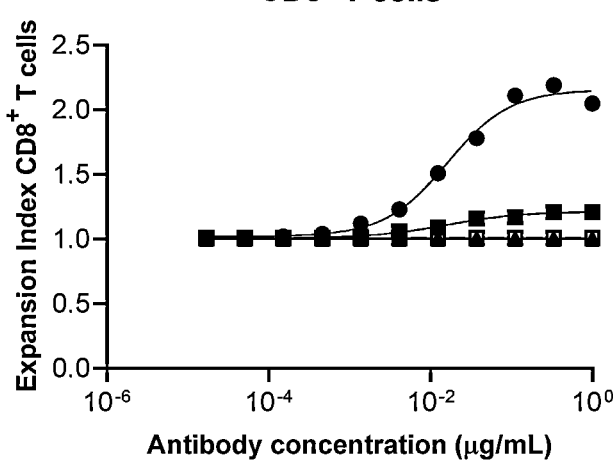

FIGS. 21A-21C: Kinetics of T-cell mediated cytotoxicity and T-cell proliferation in vitro by bsG1-huCD3-FEALxCD30-MDX060-FERR. (FIG. 21A) The kinetics of T-cell mediated cytotoxicity by bsG1-huCD3-FEALxCD30-MDX060-FERR was tested in vitro using L-428 tumor cells as target cells and purified T cells as effector cells at an E:T ratio of 4:1. Cytotoxicity was evaluated after 24 h, 48 h, and 72 h. bsG1-huCD3-FEALxb12-FERR was included as control antibody. Data shown are percentages viable cells, obtained from one representative experiment. (FIGS. 21B and 21C) CD4$^+$ (FIG. 21B) or CD8$^+$ (FIG. 21C) T cells with diluted Celltrace Violet staining were gated and the expansion index, as a measure for T-cell proliferation in the cytotoxicity assays, was calculated using the proliferation modeling tool from FlowJo.

Figure 22A:
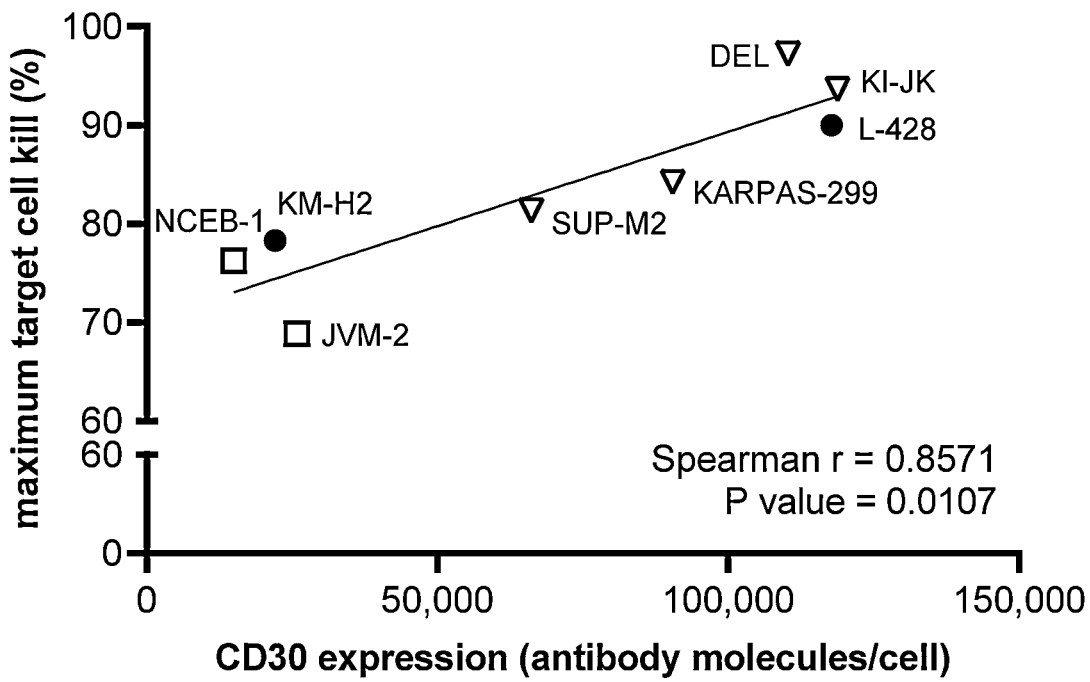
Figure 22B:
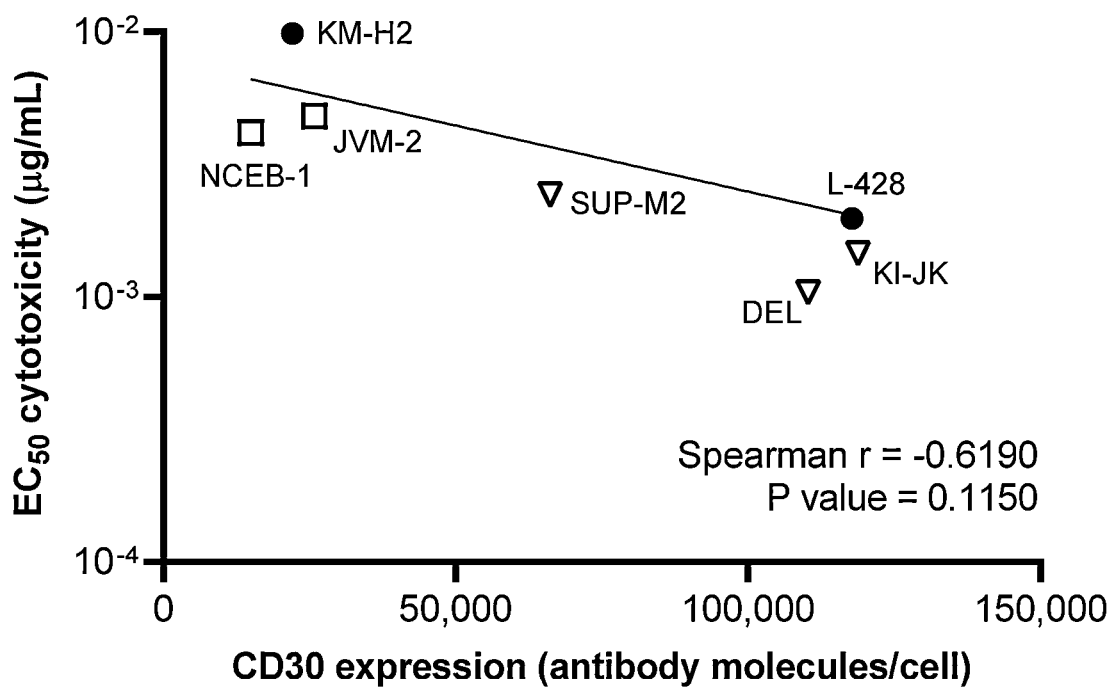

FIGS. 22A and 22B: T-cell mediated cytotoxicity in vitro by bsG1-huCD3-FEALxCD30-MDX060-FERR and correlation with CD30 expression level. The correlation between maximum T-cell mediated kill (FIG. 22A) or IC50 concentrations of T-cell mediated cytotoxicity (FIG. 22B) by bsG1-huCD3-FEALxCD30-MDX060-FERR versus CD30 expression levels was evaluated in eight tumor cell lines. A Spearman rank correlation test (GraphPad Prism software) was used to evaluate the statistical significance of the degree of correlation between T-cell mediated cytotoxicity (maximum kill or IC$_{50}$) and CD30 expression.

Figure 23A:
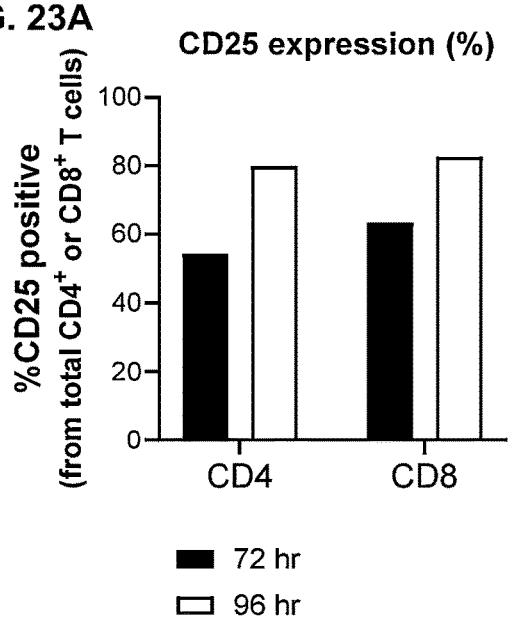
Figure 23B:
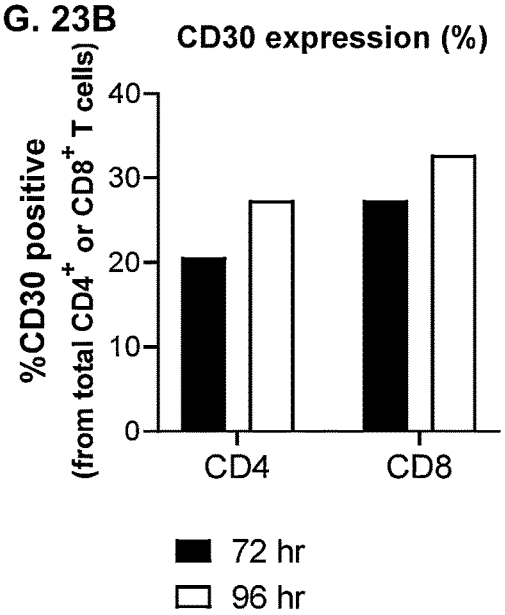
Figure 23C:
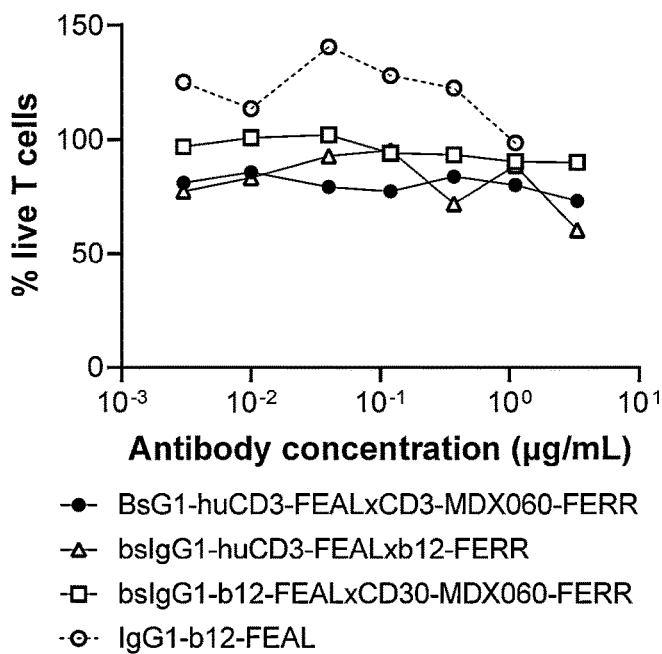

FIGS. 23A-23C: Fratricide of activated T cells by bsG1-huCD3-FEALxCD30-MDX060-FERR. Isolated healthy donor T cells were stimulated with 1 μg/mL anti-CD3 (OKT-3), 1 μg/mL anti-CD28 and 0.025 μg/mL IL-15 for 4 days. Upon confirmation of activation (CD25 upregulation), T cells were incubated with increasing concentrations of bsG1-huCD3-FEALxCD30-MDX060-FERR, bsIgG1-ctrlx CD30-MDX-060-FERR, bsIgG1-CD3xb12, or IgG1-b12-FEAL for 48 hours. BsG1-huCD3-FEALxCD30-MDX060-FERR-induced T-cell fratricide of activated-CD30$^+$ T-cells was measured as the percentage of viable T cells in each condition relative to the number of viable T cells in the condition without adding any antibodies. (FIGS. 23A and 23B) The percentage of CD25$^+$ (FIG. 23A) or CD30$^+$ (FIG. 23B) cells in CD4$^+$ or CD8$^+$ T-cells, 72- and 96 hours after stimulation with anti-CD3, anti-CD28 and IL-15, was determined by flow cytometry. (FIG. 23C) T-cell fratricide was shown as the percentage T-cell survival relative to the condition without adding any antibodies. Data are shown for one representative T-cell donor.

Figure 24A:
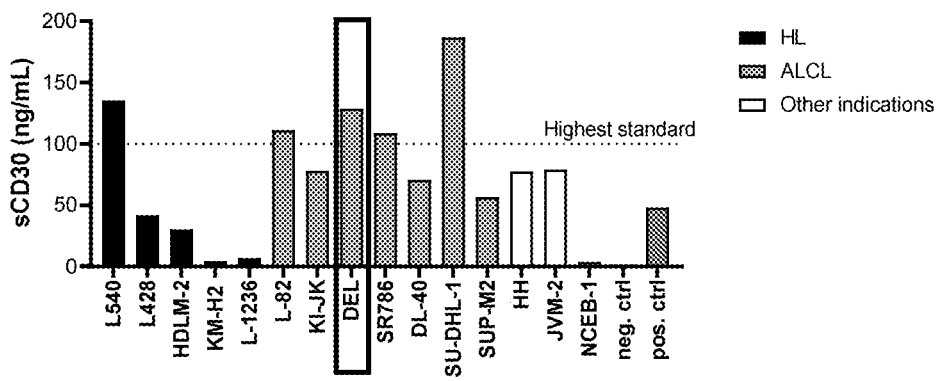
Figure 24B:
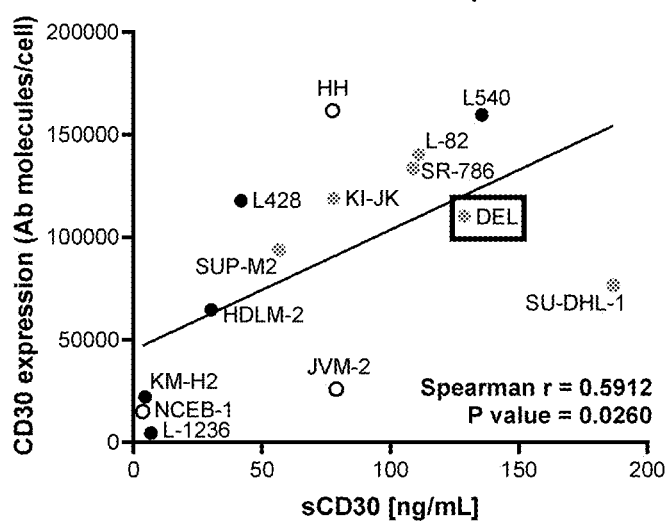
Figure 24C:
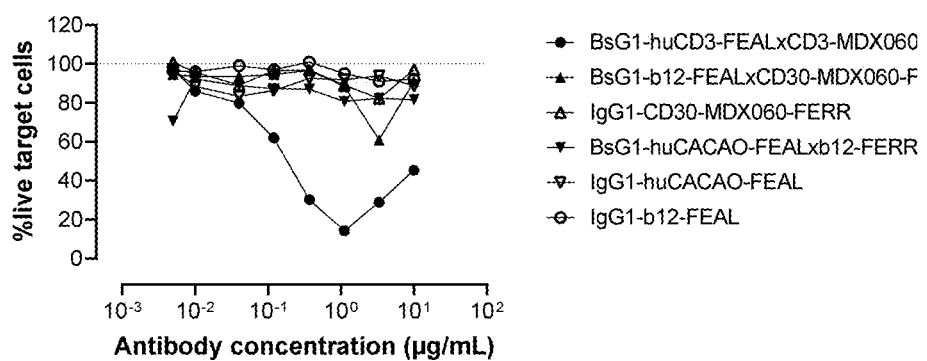

FIGS. 24A-24C: Soluble CD30 in the supernatant of CD30$^+$ cell cultures and its interference with the anti-tumor activity of BsG1-huCD3-FEALxCD30-MDX060-FERR. (FIG. 24A) The soluble CD30 (sCD30) concentration in the supernatant of different hematologic tumor cell lines, as measured by ELISA, is shown. (FIG. 24B) The correlation between sCD30 concentrations and the number of CD30 molecules on the cell surface, as determined using quantitative flow cytometry (human IgG calibrator kit-Biocytex), in different hematologic tumor cell lines, was evaluated by Spearman rank correlation test (GraphPad Prism software). (FIG. 24C) BsG1-huCD3-FEALxCD30-MDX060-FERR was tested in an in vitro cytotoxicity assay using the CD30-positive ALCL tumor cell line DEL as target cells and healthy donor isolated T cells as effector cells. The following control antibodies were included: BsG1-b12-FEALxCD30-MDX060-FERR, IgG1-CD30-MDX060-FERR, BsG1-huCD3-FEALxb12-FERR, IgG1-huCD30-FEAL and IgG1-b12-FEAL. Data shown are percentages viable cells, obtained from one representative experiment.

FIGS. 25A-25D. Induction of T-cell mediated cytotoxicity and T-cell proliferation ex vivo by bsG1-huCD3-FEALx CD30-MDX060-FERR in L-428 tumor cells. (FIG. 25A) bsG1-huCD3-FEALxCD30-MDX060-FERR was tested in an ex vivo cytotoxicity assay using L-428 tumor cells as target cells and primary patient-derived T cells as effector cells. Hodgkin lymphoma (HL), acute myeloid leukemia (AML) and peripheral T-cell lymphoma (PTCL) patient-derived peripheral blood mononuclear cells (PBMCs) were used as a source of T cells to evaluate CD3-dependent tumor cell kill. IgG1-b12-FEAL was included as control. Data shown are percentage viable target cells. (FIGS. 25B-25D) T-cell activation was evaluated by upregulation of CD69 (FIG. 25B), CD25 (FIG. 25C) and PD-1 (FIG. 25D) markers on CD4$^+$/CD8$^+$ T cells within the PBMC subset, indicated as percentage positive cells.

Figure 26A:
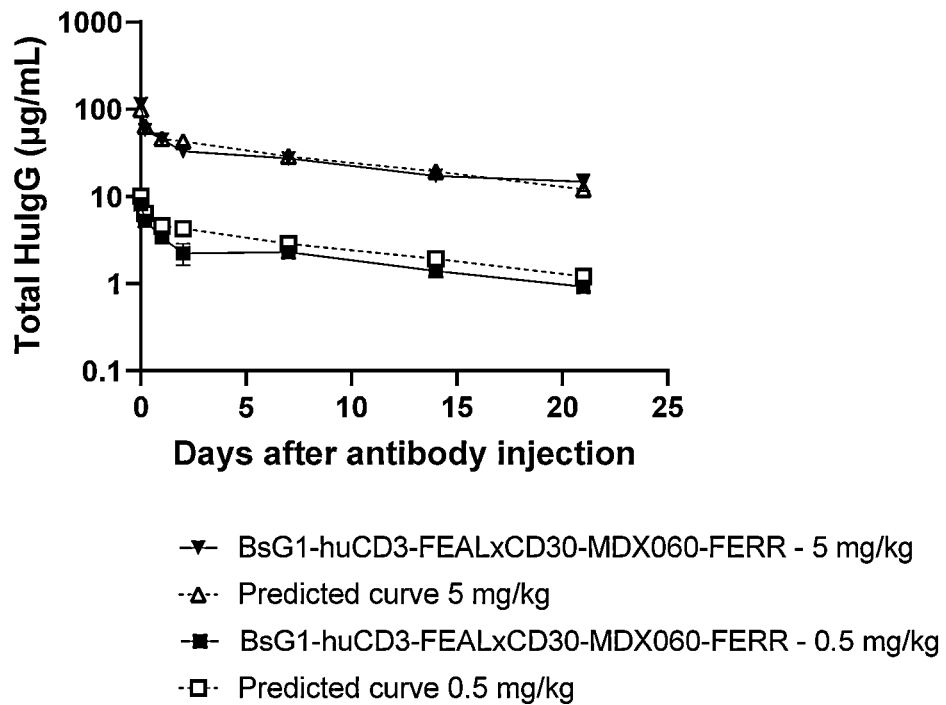
Figure 26B:
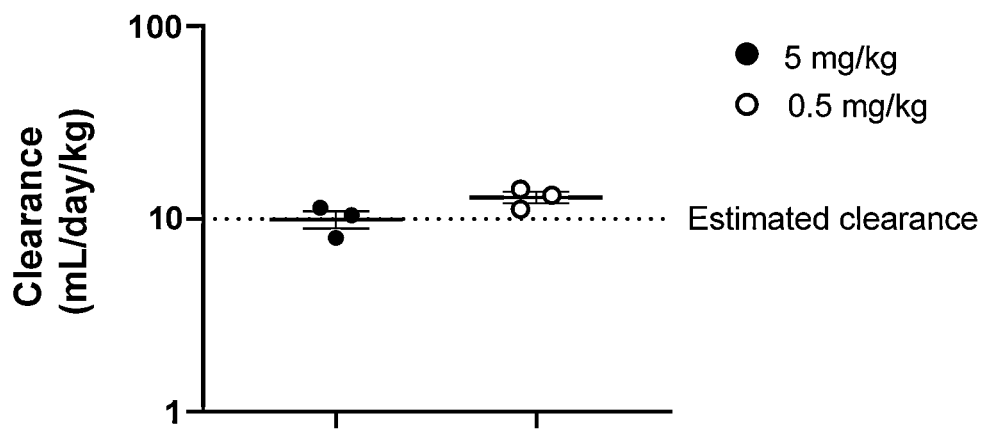

FIGS. 26A and 26B. Plasma concentrations of BsG1-huCD3-FEALxCD30-MDX060-FERR following intravenous injection in SCID mice. SCID mice were injected with a single IV dose of 10 μg (0.5 mg/kg) or 100 μg (5 mg/kg) of BsG1-huCD3-FEALxCD30-MDX060-FERR. (FIG. 26A) Total human IgG was determined by ELISA and average human IgG1 concentrations were plotted over time. (FIG. 26B) The mean clearance rate was plotted for 0.5 or 5 mg/kg dose levels. The dotted line indicates the estimated clearance rate based on standard distribution volume of a non-binding regular human IgG1 in mice.

Figure 27A:
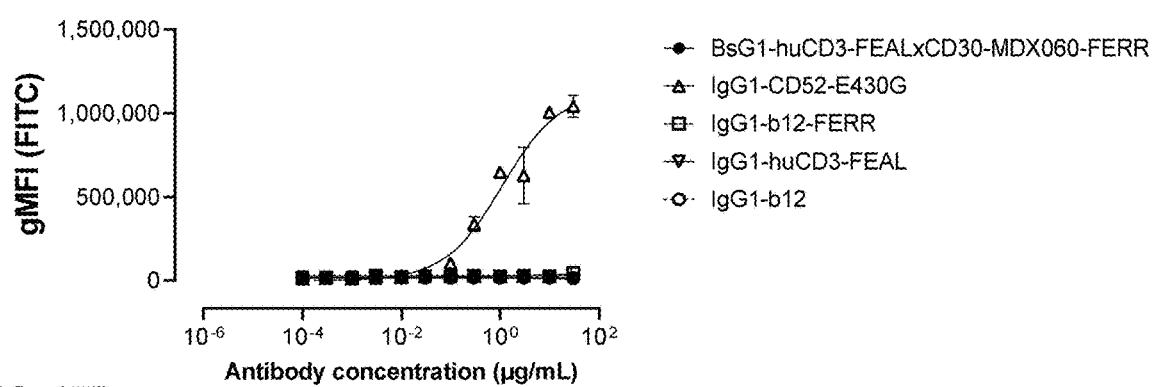
Figure 27B:
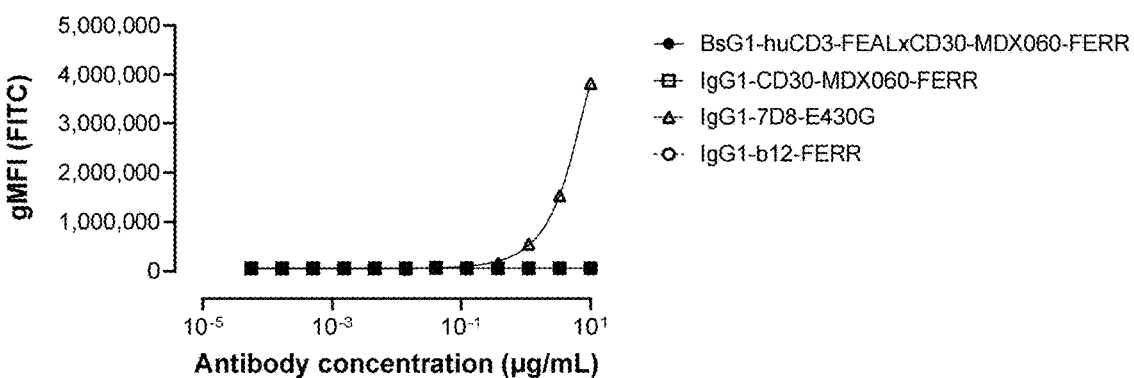

FIGS. 27A and 27B: C1q binding to membrane-bound bsG1-huCD3-FEAL×CD30-MDX060-FERR. Binding of C1q to bsG1-huCD3-FEAL×CD30-MDX060-FERR-opsonized, activated human CD8⁺ T cells, or CD30⁺ NCEB-1 cells was evaluated by flow cytometry using FITC labeled rabbit anti-C1q antibody. (FIG. 27A) Binding of bsG1-huCD3-FEAL×CD30-MDX060-FERR, IgG1-huCD3-FEAL or positive control antibody IgG1-CD52-E430G to human CD8⁺ T cells stimulated with anti-CD3/CD28 beads in the presence of normal human serum as a source of C1q. Data shown are geomean fluorescence intensities (gMFI) ±SD from replicate wells from one representative experiment. (FIG. 27B) Binding of bsG1-huCD3-FEAL×CD30-MDX060-FERR, IgG1-CD30-MDX060-FERR or positive control antibody IgG1-7D8-E430G to CD30⁺ NCEB-1 cells, in the presence of normal human serum as a source of C1q. Data shown are gMFI from one representative experiment.

DETAILED DESCRIPTION OF THE INVENTION

Definitions

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, at least about 24 hours or more, at least about 48 hours or more, at least about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to be internalized). An antibody comprises a binding region (or binding domain which may be used herein, both having the same meaning) which can interact with an antigen, a binding region comprising variable regions of both heavy and light chains of an immunoglobulin molecule, or the like. Antibodies may comprise constant regions of the antibodies (Abs) which may mediate the binding of the immunoglobulin to host tissues or factors, including various cells of the immune system (such as effector cells) and components of the complement system such as C1q, the first component in the classical pathway of complement activation.

In the context of the present invention, the term "antibody" includes a monoclonal antibody (mAb), an antibody-like polypeptide, a chimeric antibody, a human antibody, a humanized antibody, as well as an 'antibody fragment' or a 'fragment thereof' retaining the ability to specifically bind to the antigen (antigen-binding fragment) provided by any known technique, such as enzymatic cleavage, peptide synthesis, and recombinant DNA technology. The term "antibody" includes bi-, tri-, or multispecific antibodies and/or antibodies having further modifications, e.g., antibody-drug conjugates and/or antibodies with modifications in the IgG Fc domain. An antibody as defined according to the invention can possess any isotype or not have an isotype (e.g., an scFv antibody), unless the disclosure herein is otherwise limited.

It has been shown that the antigen-binding function of an antibody may be performed by fragments of a full-length antibody. Examples of binding fragments encompassed within the term "antibody" include (i) a Fab' or Fab fragment, a monovalent fragment consisting of the light chain variable domain (VL), heavy chain variable domain (VH), light chain constant region (CL) and heavy chain constant region domain 1 (CH1) domains, or a monovalent antibody as described in WO 2007/059782; (ii) F(ab')₂ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment Ward et al., Nature 341, 544546 (1989), which consists essentially of a VH domain and is also called domain antibody Holt et al; Trends Biotechnol-. 2003 November; 21(11):484-90; (vi) camelid or nanobodies Revets et al; Expert Opin Biol Ther. 2005 January; 5(1):111-24 and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Revets et al; Expert Opin Biol Ther. 2005 January; 5(1):111-24 and Bird et al., Science 242, 423426 (1988). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein.

An antibody, either as the final product or as an intermediate to generate e.g., a bispecific antibody through controlled Fab-arm exchange (cFEA), can be produced in and collected from different in vitro or ex vivo expression or production systems, for example from recombinantly modified host cells, from hybridomas or systems that use cellular extracts supporting in vitro transcription and/or translation of nucleic acid sequences encoding the antibody.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region of an IgG typically is comprised of three domains, CH1, CH2, and CH3. The term "immunoglobulin" as used herein is intended to refer to a class of structurally related glycoproteins typically consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4.

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein, including for example recombining by half-molecule exchange, as well as recombining at nucleic acid level and/or through co-expression of two half-molecules in the same cells.

The terms "first" and "second" when used herein in the context of an antibody or domain or region thereof are merely intended for ease of reference and are not intended to indicate a particular relative location or the like.

The term "antigen-binding region" or "binding region" as used herein, refers to a region of an antibody which is capable of binding to the antigen. The antigen can be any molecule, such as a polypeptide, protein, polysaccharide or combination thereof. Antigens may e.g., be presented on a cell, bacterium, or virion. The terms "antigen" and "target" may, unless contradicted by the context, be used interchangeably in the context of the present invention. The terms "antigen-binding region" and "antigen-binding site" may, unless contradicted by the context, be used interchangeably in the context of the present invention.

The term "$K_D$" (M), as used herein, refers to the equilibrium dissociation constant of a particular antibody-antigen interaction, and is obtained by dividing $k_d$ by $k_a$. $K_D$ can also be referred to as "binding affinity".

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "binding" as used herein refers to the binding of an antibody to a predetermined antigen or target, typically with a binding affinity corresponding to a $K_D$ of $1E^{-6}$ M or less, e.g. $5E^{-7}$ M or less, $1E^{-7}$ M or less, such as $5E^{-8}$ M or less, such as $1E^{-8}$ M or less, such as $5E^{-9}$ M or less, such as $1E^{-9}$ M or less, such as $1E^{-10}$ M or less or such as $1E^{-11}$ M or less when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "CD30" as used herein refers to the human Cluster of Differentiation 30 protein, also known as TNFRSF8 (Tumor Necrosis Factor Receptor Superfamily member 8). CD30 is found in various species, and thus, the term "CD30" may not be limited to human CD30, unless contradicted by context. The sequence of human CD30 is set forth in SEQ ID NO:39.

The term "CD3" as used herein refers to the human Cluster of Differentiation 3 protein which is part of the T-cell co-receptor protein complex and is composed of four distinct chains. CD3 is found in various species, and thus, the term "CD3" may not be limited to human CD3, unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε: UniProtKB/Swiss-Prot No P07766, of which a sequence herein is incorporated as SEQ ID NO:42; cynomolgus monkey CD3ε UniProtKB/Swiss-Prot No Q95LI5; or rhesus monkey CD3ε UniProtKB/Swiss-Prot No G7NCB9), and a CD3ζ-chain (zeta) chain (human CD3ζ UniProtKB/Swiss-Prot No P20963, cynomolgus monkey CD3 ζ UniProtKB/Swiss-Prot No Q09TK0). These chains associate with a molecule known as the T cell receptor (TCR) and generate an activation signal in T lymphocytes. The TCR and CD3 molecules together comprise the TCR complex.

The term "antibody binding region" refers to a region of the antigen, which comprises the epitope to which the antibody binds. An antibody binding region may be determined by epitope binning using biolayer interferometry, by alanine scan, or by domain shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and/or by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents or other agents that disrupt the three-dimensional structure of a protein or multimer thereof. The epitope may comprise amino acid residues which are directly involved in the binding, and other amino acid residues, which are not directly involved in the binding, such as amino acid residues which are effectively blocked or covered by the antibody when it is bound to the antigen.

The terms "monoclonal antibody", "monoclonal Ab", "monoclonal antibody composition", "mAb", or the like, as used herein refer to a preparation of antibody molecules of single molecular composition and typically displays a single binding specificity and affinity for a particular epitope. A monoclonal antibody can be typically made by identical cells that are all clones of a unique parent cell, such as for example hybridomas, stable cell lines or the like. Accordingly, the term "human monoclonal antibody" refers to antibodies displaying a single binding specificity which have variable and constant regions derived from human germline immunoglobulin sequences.

The human monoclonal antibodies may be produced by a hybridoma which includes a B cell obtained from a transgenic or trans-chromosomal nonhuman animal, such as a transgenic mouse, having a genome comprising a human heavy chain transgene and a light chain transgene, fused to an immortalized cell. Human monoclonal antibodies may be derived from human B cells or plasma cells. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f) that is encoded by heavy chain constant region genes. Further, each heavy chain isotype can be combined with either a kappa (κ) or lambda (λ) light chain.

The term "full-length antibody" when used herein, refers to an antibody (e.g., a parent or variant antibody) comprising one pair of a heavy and light chain or two pairs of heavy and light chains, each pair containing heavy and light chain constant and variable domains such as normally found in a heavy chain-light chain pair of a wild-type antibody of that isotype. Thus, for example, a full-length IgG1 antibody contains VH, CH1, CH2, CH3, hinge, VL and CL domains. In a full-length variant antibody, the heavy and light chain constant and variable domains may in particular contain amino acid substitutions that modify and/or improve functional properties of the antibody when compared to the full-length parent or wild-type antibody. A full-length antibody according to the present invention may be produced by a method comprising the steps of (i) cloning the CDR sequences into one or more suitable vectors comprising complete heavy and light chain sequences, and (ii) expressing the obtained suitable vectors with the heavy and light chain sequences in suitable expression systems. It is within the knowledge of the skilled person to produce a full-length antibody when starting out from either CDR sequences or full variable region sequences. Thus, the skilled person knows how to generate a full-length antibody in accordance with the present invention.

The term "humanized antibody" as used herein, refers to a genetically engineered non-human antibody, which contains human antibody constant domains and non-human variable domains modified to contain a high level of sequence homology to human variable domains. This can be achieved by grafting of non-human antibody complementarity-determining regions (CDRs), which together form the antigen binding site, onto a homologous human acceptor framework region (FR) (see i.a. WO92/22653 and EP0629240). In order to fully reconstitute the binding affinity and specificity of the parental antibody, substitution of some of the human framework residues with some of the framework residues from the parental antibody (i.e. the non-human antibody) (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as particular useful affinity and biochemical properties, e.g. to include modifications to avoid deamidation, and/or improve manufacturing. Furthermore, CDR and/or framework regions may be modified to improve affinity to the antigen, for example via affinity maturation procedures.

"The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes. Human monoclonal antibodies can be generated using transgenic or transchromosomal mice carrying parts of the human immune system rather than the mouse system, such as a HCo12 mouse (see e.g. WO 03/059282), or the like.

The term "Fc region" as used herein, refers to a region comprising, in the direction from the N- to C-terminal ends of the two heavy chain polypeptides of the antibody, at least a hinge region, a CH2 region and a CH3 region. The Fc polypeptides are typically glycosylated. An Fc region of the antibody may mediate the binding of the immunoglobulin to host tissues or factors, including various cells of the immune system (such as effector cells) and components of the complement system. Fc regions typically also bind FcRn and protein A.

The phrase "amino acid corresponding to the amino acid at position . . . ", or the like, as used herein refers to an amino acid position number in a human IgG1 heavy chain. Corresponding amino acid positions in other immunoglobulins may be found by alignment with human IgG1. Unless otherwise stated or contradicted by context, the amino acids of the constant region sequences are herein numbered according to the EU-index of numbering (described in Kabat, E. A. et al., 1991, Sequences of proteins of immunological interest. 5th Edition—US Department of Health and Human Services, NIH publication No. 91-3242, pp 662, 680, 689). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain.

It is considered well-known in the art how to align a sequence or segment in a sequence and thereby determine the corresponding position in a sequence to an amino acid position according to the present invention.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat, E. A. et al., Sequences of proteins of immunological interest. 5th Edition—US Department of Health and Human Services, NIH publication No. 91-3242, pp 662,680,689 (1991). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus, for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions," as used herein, is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxicity (ADCC), (v) Fc-gamma receptor (FcgR)-binding, (vi) antibody-dependent, FcγR-mediated antigen crosslinking, (vii) antibody-dependent cellular phagocytosis (ADCP), (viii) complement-dependent cellular cytotoxicity (CDCC), (ix) complement-enhanced cytotoxicity, (x) binding to complement receptor of an opsonized antibody mediated by the antibody, (xi) opsonisation, and (xii) a combination of any of (i) to (xi).

The term "inertness", "inert" or "non-activating" as used herein, refers to an Fc region which is not able or has minimal ability to bind any FcγR, induce Fc-mediated cross-linking of FcγRs, induce FcγR-mediated effector functions such as ADCC and ADCP, induce FcγR-mediated cross-linking of target antigens via two Fc regions of individual antibodies, and/or is not able to bind C1q and induce complement-mediated effector functions such as CDC and CDCC. The inertness of an Fc region of an antibody, may be tested using the antibody in a monospecific or bispecific format.

The term "monovalent antibody", in the context of the present invention, refers to an antibody molecule that can interact with an antigen, with only one antigen-binding domain (e.g. one Fab arm). In the context of a multispecific, such as a bispecific, antibody, "monovalent antibody binding" refers to the binding of the multispecific antibody to one antigen with only one antigen-binding domain (e.g. one Fab arm).

The term "monospecific antibody" in the context of the present invention, refers to an antibody that has binding specificity to one antigen, one epitope only. The antibody may be a monospecific, monovalent antibody (i.e. carrying only one antigen-binding region), a monospecific, bivalent antibody (e.g. an antibody with two identical antigen-binding regions) or a monospecific, multivalent antibody (e.g. an antibody with more than two identical antigen-binding regions).

The term "multispecific antibody" refers to an antibody having two or more antigen-binding domains that bind two or more different epitopes. The term "bispecific antibody" refers to an antibody having two antigen-binding domains that bind different epitopes, e.g. two non-identical pairs of VH and VL regions, two non-identical Fab-arms or two Fab-arms with non-identical CDR regions. In the context of this invention, bispecific and multispecific antibodies have specificity for two or more, respectively, different epitopes. Such epitopes may be on the same or different antigens or targets. If the epitopes are on different antigens, such antigens may be on the same cell or different cells, cell types or structures, such as extracellular matrix or vesicles and soluble protein. Multispecific and bispecific antibodies may thus be capable of crosslinking multiple antigens, e.g. two different cells.

The term "bivalent antibody" refers to an antibody that has two antigen-binding regions, where said antigen-binding regions may be identical and bind to the same epitopes or they may be non-identical and bind to different epitopes which may be on the same or on different antigen(s). Hence, a bivalent antibody may be a monospecific antibody or a bispecific antibody.

The term "amino acid" and "amino acid residue" may herein be used interchangeably, and are not to be understood limiting. Amino acids are organic compounds containing amine ($-NH_2$) and carboxyl ($-COOH$) functional groups, along with a side chain (R group) specific to each amino acid. In the context of the present invention, amino acids may be classified based on structure and chemical characteristics. Thus, classes of amino acids may be reflected in one or both of the following tables:

TABLE 1

Main classification based on structure and general chemical characterization of R group

| Class | Amino acid |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 2

Alternative Physical and Functional Classifications of Amino Acid Residues

| Class | Amino acid |
|---|---|
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |

TABLE 2-continued

Alternative Physical and Functional Classifications of Amino Acid Residues

| Class | Amino acid |
|---|---|
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, a conservative substitution may be substitution of leucine with isoleucine as they are both aliphatic, branched hydrophobes. Similarly, an example of a conservative substitution is substitution of aspartic acid with glutamic acid since they are both small, negatively charged residues.

In the context of the present invention, a substitution in an antibody is indicated as: Original amino acid—number of position—substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine.

Accordingly, the notation "K409R" or "Lys409Arg" means, that the antibody comprises a substitution of Lysine with Arginine in amino acid position 409. Substitution of an amino acid at a given position to any other amino acid is referred to as: Original amino acid-position; or e.g. "K409". For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is: "Lys409Arg,Ala,Phe" or "Lys409Arg/Ala/Phe" or "K409R, A,F" or "K409R/A/F" or "K409 to R, A, or F". Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. These substitutions may also be designated K409A, K409C, etc. or K409A,C, etc. or K409A/C/etc. The same applies by analogy to each and every position mentioned herein, to specifically include herein any one of such substitutions.

The term "host cell", as used herein, is intended to refer to a cell into which a nucleic acid such as an expression vector has been introduced. It should be understood that such terms are intended to refer not only to the particular subject cell, but may also include the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells (i.e. host cells used for the production of recombinant proteins) include, for example, transfectomas, such as CHO cells, HEK-293 cells, Expi293F cells, PER.C6 cells, NS0 cells, and lymphocytic cells, and prokaryotic cells such as E. coli and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK-293 cells, Expi293F cells, plant cells, or fungi, including yeast cells.

For purposes of the present invention, sequence identity between two amino acid sequences is determined over the length of the referenced sequence using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent or referenced sequence.

TABLE 3

Amino acid sequences

| SEQ ID NO: | Reference | Domain | Sequence |
|---|---|---|---|
| 1 | IgG1-CD30-MDX060-FERR | VH_CDR1 | GGSFSAYY |
| 2 | IgG1-CD30-MDX060-FERR | VH_CDR2 | INHGGGT |

TABLE 3-continued

Amino acid sequences

| SEQ ID NO: | Reference | Domain | Sequence |
|---|---|---|---|
| 3 | IgG1-CD30-MDX060-FERR | VH_CDR3 | ASLTAY |
| 4 | IgG1-CD30-MDX060-FERR | VL_CDR1 | QGISSW |
| 5 | IgG1-CD30-MDX060-FERR | VL_CDR2 | AAS |
| 6 | IgG1-CD30-MDX060-FERR | VL_CDR3 | QQYDSYPIT |
| 7 | IgG1-huCD3-FEAL | VH_CDR1 | GFTFNTYA |
| 8 | IgG1-huCD3-FEAL | VH_CDR2 | IRSKYNNYAT |
| 9 | IgG1-huCD3-FEAL | VH_CDR3 | VRXGNFGNSYVSWFAY, wherein X is H or G |
| 10 | IgG1-huCD3-FEAL | VL_CDR1 | TGAVTTSNY |
| 11 | IgG1-huCD3-FEAL | VL_CDR2 | GTN |
| 12 | IgG1-huCD3-FEAL | VL_CDR3 | ALWYSNLWV |
| 13 | IgG1-CD30-MDX060-FERR | VH | QVQLQQWGAGLLKPSETLSLTCAVYGGSFSAYYWSWIRQPPGKGLEWIGDINHGGGTNYNPSLKSRVTISVDTSKNQFSLKLNSVTAADTAVYYCASLTAYWGQGSLVTVSS |
| 14 | IgG1-CD30-MDX060-FERR | VL | DIQMTQSPTSLSASVGDRVTITCRASQGISSWLTWYQQKPEKAPKSLIYAASSLQSGVPSRFSGSGSGTDFTLTISSLQPEDFATYYCQQYDSYPITFGQGTRLEIK |
| 15 | IgG1-huCD3-FEAL | VH | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRXGNFGNSYVSWFAYWGQGTLVTVSS, wherein X is H or G |
| 16 | IgG1-huCD3-FEAL | VL | QAVVTQEPSFSVSPGGTVTLTCRSSTGAVTTSNYANWVQQTPGQAFRGLIGGTNKRAPGVPARFSGSLIGDKAALTITGAQADDESIYFCALWYSNLWVFGGGTKLTVL |
| 17 | IgG1-CD30-MDX060-FERR | Full heavy chain | QVQLQQWGAGLLKPSETLSLTCAVYGGSFSAYYWSWIRQPPGKGLEWIGDINHGGGTNYNPSLKSRVTISVDTSKNQFSLKLNSVTAADTAVYYCASLTAYWGQGSLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFERGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 18 | IgG1-CD30-MDX060-FERR | Full light chain | DIQMTQSPTSLSASVGDRVTITCRASQGISSWLTWYQQKPEKAPKSLIYAASSLQSGVPSRFSGSGSGTDFTLTISSLQPEDFATYYCQQYDSYPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 19 | IgG1-huCD3-FEAL | Full heavy chain | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVA |

TABLE 3-continued

Amino acid sequences

| SEQ ID NO: | Reference | Domain | Sequence |
|---|---|---|---|
| | | | VSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLTCLVKGFYPSDIAVEW ESNGQPENNYKTTPPVLDSDGSFLLYSKLTVDKSRWQQ GNVFSCSVMHEALHNHYTQKSLSLSPG |
| 20 | IgG1-huCD3-FEAL | Full light chain | QAVVTQEPSFSVSPGGTVTLTCRSSTGAVTTSNYANWV QQTPGQAFRGLIGGTNKRAPGVPARFSGSLIGDKAALTI TGAQADDESIYFCALWYSNLWVFGGGTKLTVLGQPKAA PSVTLFPPSSEELQANKATLVCLISDFYPGAVTVAWKADS SPVKAGVETTTPSKQSNNKYAASSYLSLTPEQWKSHRSY SCQVTHEGSTVEKTVAPTECS |
| 21 | IgG1-CD30-hAC10-FEAR | Full heavy chain | QVQLVQSGAEVKKPGASVKVSCKASGYTFTDYYITWVR QAPGQGLEWMGWIYPGSGNTKYNEKFKGRVTMTRDTSI STAYMELSRLRSDDTAVYYCANYGNYWFAYWGQGTLVT VSSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPAP EFEGGPSVFLFPPKPKDTLMISRTPEVTCVVVAVSHEDPE VKFNWYVDGVEVHNAKTKPREEQYNSTYRVVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSRLTVDKSRWQQGNVFSCS VMHEALHNHYTQKSLSLSPG |
| 22 | IgG1-CD30-hAC10-FEAR | Full light chain | DIVMTQSPDSLAVSLGERATINCKASQSVDFDGDSYMN WYQQKPGQPPKLLIYAASNLESGVPDRFSGSGSGTDFTL TISSLQAEDVAVYYCQQSNEDPWTFGQGTKVEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |
| 23 | IgG1-CD30-HRS-3-FEAR | Full heavy chain | QVQLQQSGAELARPGASVKMSCKASGYTFTTYTIHWVR QRPGHDLEWIGYINPSSGYSDYNQNFKGKTTLTADKSS NTAYMQLNSLTSEDSAVYYCARRADYGNYEYTWFAYWG QGTTVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSCDKTHT CPPCPAPEFEGGPSVFLFPPKPKDTLMISRTPEVTCVVVA VSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLTCLVKGFYPSDIAVEW ESNGQPENNYKTTPPVLDSDGSFFLYSRLTVDKSRWQQ GNVFSCSVMHEALHNHYTQKSLSLSPG |
| 24 | IgG1-CD30-HRS-3-FEAR | Full light chain | DIVMTQSPKFMSTSVGDRVTVTCKASQNVGTNVAWFQ QKPGQSPKVLIYSASYRYSGVPDRFTGSGSGTDFTLTIS NVQSEDLAEYFCQQYHTYPLTFGGGTKLEINRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC |
| 25 | IgG1-CD30-HeFi-I-FEAR | Full heavy chain | EVKLVESGGGLVQPGGSLRLSCATSGFTFSDYYMNWVR QPPGKALEWLGFIRNKANGYTTEFSASVMGRFTISRDDS QSILYLQMNTLRAEDSATYYCARDPPYGNPHYYAMDYW GQGTSVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKRVEPKSCDKTH TCPPCPAPEFEGGPSVFLFPPKPKDTLMISRTPEVTCVVVA VSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLTCLVKGFYPSDIAVEW ESNGQPENNYKTTPPVLDSDGSFFLYSRLTVDKSRWQQ GNVFSCSVMHEALHNHYTQKSLSLSPG |
| 26 | IgG1-CD30-HeFi-I-FEAR | Full light chain | DIVLTQSPASLAVSLGQRATISCRASKSVSASGYNYMHW YQQKAGQPPKLLIHLASNLESGVPARFSGSGSGTDFTLNI HPVEEEDASTYYCQHSGELPPTFGSGTKLEIKRTVAAPSV FIFPPSDEQLKSGTASVVCLLNNFYPREAKVQWKVDNAL QSGNSQESVTEQDSKDSTYSLSSTLTLSKADYEKHKVYA CEVTHQGLSSPVTKSFNRGEC |

TABLE 3-continued

Amino acid sequences

| SEQ ID NO: | Reference | Domain | Sequence |
|---|---|---|---|
| 27 | IgG1-CD30-T405-FEAR | Full heavy chain | QVQLQQIGAELVRPGASVKLSCKASGYTFNNYWINWVKQRPGQGLEWIGNIYPSDSRSNYNQKFKDKATLTVDKPSSTAYMQLSSPTSEDSAVYYCTLGSYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 28 | IgG1-CD30-T405-FEAR | Full light chain | DVVMTQTPLTLSVTIGQPASISCKSSQSLSDSDGKTYLNWLLQRPGQSPKRLIYLVSKLDSGVPDRFTGSGSGTDFTLKISRVEAEDLGVYYCWQGAHFPRTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 29 | IgG1-CD30-T105-FEAR | Full heavy chain | QVTLKESGPGILQPSQTLSLTCSFSGFSLSTSGMGVSWIRQPSGKDLEWLAHIYWDDDKRYNPSLKSRLTISKDTSSNQVFLKITSVDTADTATYYCARRADGLYFYLDVWGAGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 30 | IgG1-CD30-T105-FEAR | Full light chain | DIVMTQSQKFMSTSVGDRVSVTCKASQNVNTNVAWYQQKPGQSPEALIYSASYRYSGVPDRFTGSGSGTDFTLTISNVQSEDLAEYFCQQYNSYPLTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 31 | IgG1-CD30-T408-FEAR | Full heavy chain | QVQLQQPGAELVRPGASVKLSCKASGYTFTSYWINWVKQRPGQGLEWIGNIYPSDSYSNYNQKFKDKATLTVDKSSSTAYMQLSSPTSEDSAVYYCTLGSYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 32 | IgG1-CD30-T408-FEAR | Full light chain | DVVMTQTPLTLSVTIGQPASISCKSSQSLSDSDGKTYLNWLLQRPGQSPKRLIYLVSKLDSGVPDRFGGGTDFTLKISRVEAEDLGVYYCWQGAHFPRTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 33 | IgG1-CD30-T215-FEAR | Full heavy chain | QVTLKESGPGILQPSQTLSLTCSFSGFSLSVSGMGVSWIRQPSGKGLEWLAHIWDDDRRSNPSLRSRLTISKDTSNNQVFLKITSVDTADTATYYCARRPDLYGNYFFFDFWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |

TABLE 3-continued

Amino acid sequences

| SEQ ID NO: | Reference | Domain | Sequence |
|---|---|---|---|
| 34 | IgG1-CD30-T215-FEAR | Full light chain | DIVMTQSQKFMSTSVGDRVSVTCKASQNVFTNVAWYQ QKLGQSPKPLIYSASYRYSGVPDRFTGSGTDFTLTISD VQSEDLAEYFCQQYNSYPVTFGAGTKLELKRTVAAPSVFI FPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC |
| 35 | IgG1-huCD3H101G-FEAL | Full heavy chain | EVKLVESGGGLVQPGGSLRLSCAASGFTFNTYAMNWVR QAPGKGLEWVARIRSKYNNYATYYADSVKDRFTISRDDS KSSLYLQMNNLKTEDTAMYYCVRGGNFGNSYVSWFAYW GQGTLVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKRVEPKSCDKTH TCPPCPAPEFEGGPSVFLFPPKPKDTLMISRTPEVTCVVVA VSHEDPEVKFNWYVDGVEVHNAKTKPREEQYNSTYRVV SVLTVLHQDWLNGKEYKCKVSNKALPAPIEKTISKAKGQ PREPQVYTLPPSREEMTKNQVSLTCLVKGFYPSDIAVEW ESNGQPENNYKTTPPVLDSDGSFLLYSKLTVDKSRWQQ GNVFSCSVMHEALHNHYTQKSLSLSPG |
| 36 | IgG1-b12-FEAL | Full heavy chain | QVQLVQSGAEVKKPGASVKVSCQASGYRFSNFVIHWVR QAPGQRFEWMGWINPYNGNKEFSAKFQDRVTFTADTSA NTAYMELRSLRSADTAVYYCARVGPYSWDDSPQDNYYM DVWGKGTTVIVSSASTKGPSVFPLAPSSKSTSGGTAALG CLVKDYFPEPVTVSWNSGALTSGVHTFPAVLQSSGLYSL SSVVTVPSSSLGTQTYICNVNHKPSNTKVDKRVEPKSCD KTHTCPPCPAPEFEGGPSVFLFPPKPKDTLMISRTPEVTCV VVAVSHEDPEVKFNWYVDGVEVHNAKTKPREEQYNSTY RVVSVLTVLHQDWLNGKEYKCKVSNKALPAPIEKTISKA KGQPREPQVYTLPPSREEMTKNQVSLTCLVKGFYPSDIA VEWESNGQPENNYKTTPPVLDSDGSFLLYSKLTVDKSR WQQGNVFSCSVMHEALHNHYTQKSLSLSPG |
| 37 | IgG1-b12-FEAL | Full light chain | EIVLTQSPGTLSLSPGERATFSCRSSHSIRSRRVAWYQH KPGQAPRLVIHGVSNRASGISDRFSGSGSGTDFTLTITR VEPEDFALYYCQVYGASSYTFGQGTKLERKRTVAAPSVFI FPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC |
| 38 | IgG1-b12-FERR | Full heavy chain | QVQLVQSGAEVKKPGASVKVSCQASGYRFSNFVIHWVR QAPGQRFEWMGWINPYNGNKEFSAKFQDRVTFTADTSA NTAYMELRSLRSADTAVYYCARVGPYSWDDSPQDNYYM DVWGKGTTVIVSSASTKGPSVFPLAPSSKSTSGGTAALG CLVKDYFPEPVTVSWNSGALTSGVHTFPAVLQSSGLYSL SSVVTVPSSSLGTQTYICNVNHKPSNTKVDKRVEPKSCD KTHTCPPCPAPEFERGPSVFLFPPKPKDTLMISRTPEVTCV VVDVSHEDPEVKFNWYVDGVEVHNAKTKPREEQYNSTY RVVSVLTVLHQDWLNGKEYKCKVSNKALPAPIEKTISKA KGQPREPQVYTLPPSREEMTKNQVSLTCLVKGFYPSDIA VEWESNGQPENNYKTTPPVLDSDGSFFLYSRLTVDKSR WQQGNVFSCSVMHEALHNHYTQKSLSLSPG |
| 39 | human CD30 | | FPQDRPFEDTCHGNPSHYYDKAVRRCCYRCPMGLFPTQ QCPQRPTDCRKQCEPDYYLDEADRCTACVTCSRDDLVE KTPCAWNSSRVCECRPGMFCSTSAVNSCARCFFHSVCP AGMIVKFPGTAQKNTVCEPASPGVSPACASPENCKEPSS GTIPQAKPTPVSPATSSASTMPVRGGTRLAQEAASKLTR APDSPSSVGRPSSDPGLSPTQPCPEGSGDCRKQCEPDY YLDEAGRCTACVSCSRDDLVEKTPCAWNSSRTCECRPG MICATSATNSCARCVPYPICAAETVTKPQDMAEKDTTFE APPLGTQPDCNPTPENGEAPASTSPTQSLLVDSQASKTL PIPTSAPVALSSTGKPVLDAGPVLFWVILVLVVVVGSSAF LLCHRRACRKRIRQKLHLCYPVQTSQPKLELVDSRPRRS STQLRSGASVTEPVAEERGLMSQPLMETCHSVGAAYLES LPLQDASPAGGPSSPRDLPEPRVSTEHTNNKIEKIYIMKA DTVIVGTVKAELPEGRGLAGPAEPELEEELEADHTPHYPE QETEPPLGSCSDVMLSVEEEGKEDPLPTAASGK |
| 40 | Cynomolgous monkey CD30 | | FPQDRPFEDTCRGNPGHYYDKAVRRCCYRCPTGTAQKN TVCEPASPGVSPACASPENCKEPSSGTIPQAKPTPVSPAT SNASTMPLRGGTRLAQEAASKLTRAPGSPSSVGRPSSDP GLSPTQPCPQGSGDCRKQCEPDYYLDEAGRCTACVSCS RDDLVEKTPCAWNSSRICECRPGMICATSATNSCARCVP |

TABLE 3-continued

Amino acid sequences

| SEQ ID NO: | Reference | Domain | Sequence |
|---|---|---|---|
| | | | YPICAAETGTKPQDMAEKDTTFEAPPVGTQPDCSPTPEN GEAPASTSPTLSSLVDSQASKTLPIPTSAPIALSSTGKPVL DAGPVLFWVILVLAVVVGSSTFLLCHRRACRKRIRQKLHL CYPVQTSRPKLELVDSRPRRSSTQFESGTFVTKPSAEELG LMSLPPKETCRNVGAACPESLPLWDASPAGGPSSPRDLP EPRVSTEHTNNRIEKIYIMKADTVIVGTVKAELPEGQGLA GPAEPELEEELEADHAPHYPEQETEPPLGSCSDVMLSVEE EGKEDPLPTAASGK |
| 41 | Rhesus monkey CD30 | | FPQDRPFEDTCRGNPGHYYDKAVRRCCYRCPMGLFPTQ QCPQRPADCRKQCEPDYYLDEAGRCTACVSCSRDDLVE KMPCAWNSSRVCECQPGMFCAVSVVNSCARCFFHSVCP AGMIVKFPGTAQKNTVCEPASPGVSPACASPENCKEPSS GTIPQAKPTPVSPATSNASTMPLRGGTRLAQEAASKLTR APGSPSSVGRPSSDPGLSPTQPCPQGSGDCRKQCEPDY YLDEAGRCTACVSCSRDDLVEKTPCAWNSSRICECRPG MICATSATNSCARCVPYPICAAETGTKPQDMAEKDTTFE APPVGTQPDCSPTPENGEAPASTSPTLSSLVDSQASKTLP IPTSAPIALSSTGKPVLDAGPVLFWVILVLAVVVGSSTFLL CHRRACRKRIRQKLHLCYPVQTSRPKLELVDSRPRRSST QFESGTFVTKPSAEELGLMSLPPKETCRNVGAACPESLPL WDASPAGGPSSPRDLPEPRVSTEHTNNRIEKIYIMKADT VIVGTVKAELPEGQGLAGPAEPELEEELEADHAPHYPEQE TEPPLGSCSDVMLSVEEEGKEDPLPTAASGK |
| 42 | human CD3 (epsilon) | | QDGNEEMGGITQTPYKVSISGTTVILTCPQYPGSEILWQ HNDKNIGGDEDDKNIGSDEDHLSLKEFSELEQSGYYVCY PRGSKPEDANFYLYLRARVCENCMEMDVMSVATIVIVDI CITGGLLLLVYYWSKNRKAKAKPVTRGAGAGGRQRGQN KERPPPVPNPDYEPIRKGQRDLYSGLNQRRI |
| 43 | Cynomolgus monkey CD3 | | QDGNEEMGSITQTPYQVSISGTTVILTCSQHLGSEAQW QHNGKNKEDSGDRLFLPEFSEMEQSGYYVCYPRGSNPE DASHHLYLKARVCENCMEMDVMAVATIVIVDICITLGLLL LVYYWSKNRKAKAKPVTRGAGAGGRQRGQNKERPPPVP NPDYEPIRKGQQDLYSGLNQRRI |
| 44 | IgG1 constant region | | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPELL GGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSKLTVDKSRWQQGNVFSCSVMH EALHNHYTQKSLSLSPG |
| 45 | IgG1 constant region | with FER substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE RGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSKLTVDKSRWQQGNVFSCSVMH EALHNHYTQKSLSLSPG |
| 46 | IgG1 constant region | with FEA substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE GGPSVFLFPPKPKDTLMISRTPEVTCVVVAVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSKLTVDKSRWQQGNVFSCSVMH EALHNHYTQKSLSLSPG |
| 47 | IgG1 constant region | with F405L substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPELL GGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY |

TABLE 3-continued

Amino acid sequences

| SEQ ID NO: | Reference | Domain | Sequence |
|---|---|---|---|
| | | | KTTPPVLDSDGSFLLYSKLTVDKSRWQQGNVFSCSVMH EALHNHYTQKSLSLSPG |
| 48 | IgG1 constant region | with K409R substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPELL GGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSRLTVDKSRWQQGNVFSCSVMH EALHNHYTQKSLSLSPG |
| 49 | IgG1 constant region | with FER substitution and with F405L substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE RGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFLLYSKLTVDKSRWQQGNVFSCSVMH EALHNHYTQKSLSLSPG |
| 50 | IgG1 constant region | with FER substitution and with K409R substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE RGPSVFLFPPKPKDTLMISRTPEVTCVVVDVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSRLTVDKSRWQQGNVFSCSVMH EALHNHYTQKSLSLSPG |
| 51 | IgG1 constant region | with FEA substitution and with F405L substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE GGPSVFLFPPKPKDTLMISRTPEVTCVVVAVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFLLYSKLTVDKSRWQQGNVFSCSVMH EALHNHYTQKSLSLSPG |
| 52 | IgG1 constant region | with FEA substitution and with K409R substitution (bold) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKRVEPKSCDKTHTCPPCPAPEFE GGPSVFLFPPKPKDTLMISRTPEVTCVVVAVSHEDPEVKF NWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSRLTVDKSRWQQGNVFSCSVMH EALHNHYTQKSLSLSPG |
| 53 | constant region | constant region of human kappa light chain | RTVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| 54 | constant region | constant region of human lambda light chain | GQPKAAPSVTLFPPSSEELQANKATLVCLISDFYPGAVTV AWKADSSPVKAGVETTTPSKQSNNKYAASSYLSLTPEQ WKSHRSYSCQVTHEGSTVEKTVAPTECS |
| 55 | IgG1-CD30-MDX060-FEAR | Full heavy chain | QVQLQQWGAGLLKPSETLSLTCAVYGGSFSAYYWSWIR QPPGKGLEWIGDINHGGGTNYNPSLKSRVTISVDTSKN QFSLKLNSVTAADTAVYYCASLTAYWGQGSLVTVSSAST KGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKRVEPKSCDKTHTCPPCPAPEFEGGP SVFLFPPKPKDTLMISRTPEVTCVVVAVSHEDPEVKFNWY VDGVEVHNAKTKPREEQYNSTYRVVSVLTVLHQDWLNG KEYKCKVSNKALPAPIEKTISKAKGQPREPQVYTLPPSRE |

TABLE 3-continued

Amino acid sequences

| SEQ ID NO: | Reference | Domain | Sequence |
|---|---|---|---|
| | | | EMTKNQVSLTCLVKGFYPSDIAVEWESNGQPENNYKTTP PVLDSDGSFFLYSRLTVDKSRWQQGNVFSCSVMHEALH NHYTQKSLSLSPG |

Further Aspects and Embodiments of the Invention

As described above, in a first aspect, the invention relates to a multispecific antibody comprising:
(i) a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively, and
(ii) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively.

In one embodiment, the X in SEQ ID NO:9 is an H. In another embodiment, the X in SEQ ID NO:9 is a G.

In one embodiment, the first heavy chain variable region is human or humanized. In another embodiment, the first light chain variable region is human or humanized. In one embodiment, the second heavy chain variable region is human or humanized. In another embodiment, the second light chain variable region is human or humanized. In another embodiment, the first heavy chain variable region and the first light chain variable region are human. In another embodiment, the first heavy chain variable region and the first light chain variable region are humanized. In another embodiment, the second heavy chain variable region and the second light chain variable region are human. In another embodiment, the second heavy chain variable region and the second light chain variable region are humanized. In another embodiment, the first heavy chain variable region and the first light chain variable region are human and the second heavy chain variable region and the second light chain variable region are human. In another embodiment, the first heavy chain variable region and the first light chain variable region are human and the second heavy chain variable region and the second light chain variable region are humanized.

As will be well-known to the skilled person, each antigen-binding region of an antibody generally comprise a heavy chain variable region (VH) and a light chain variable region (VL), and each of the variable regions comprises three CDR sequences, CDR1, CDR2 and CDR3, respectively, and may comprise four framework sequences, FR1, FR2, FR3 and FR4, respectively. This structure is preferably also found in the antibodies according to the present invention. In one embodiment, one, two, three or all of said four framework sequences are human framework sequences.

As described above, the multispecific antibody according to the invention comprises an antigen-binding region capable of binding to human CD30, the sequence of which is set forth in SEQ ID NO:39. In particular, the antibody according to the invention is an antibody wherein said antigen-binding region capable of binding to human CD30 is capable of binding to the extracellular domain of human CD30, such as a CD30 molecule expressed on a cell, more preferably a tumor cell.

As described, the antibody comprises a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively.

CDR1, CDR2 and CDR3 regions can be identified from variable heavy and light chain regions using methods known in the art. The CDR regions from said variable heavy and light chain regions have been annotated according to IMGT (see Lefranc, M.-P., The Immunologist, 7, 132-136 (1999); Lefranc, Developmental and Comparative Immunology, 27(1), 55-77 (2003)).

In one embodiment, the antigen-binding region that binds to CD30 comprises:
a (first) heavy chain variable region (VH) comprising the sequence of SEQ ID NO:13, or a sequence having at least 90%, at least 95%, at least 97%, or at least 99% amino acid sequence identity to the sequence of SEQ ID NO: 13; and,
a (first) light chain variable region (VL) comprising the sequence of SEQ ID NO:14 or a sequence having at least 90%, at least 95%, at least 97%, or at least 99% amino acid sequence identity to the sequence of SEQ ID NO: 14.

In a further embodiment, the antibody according to the invention comprises a heavy chain variable (VH) region of the antigen-binding region that binds to CD30 as defined herein, wherein the sequences comprises, in total, at the most 1, 2, 3, 4 or 5 amino acid substitutions, when compared with SEQ ID NO:13.

In a further embodiment, the antibody according to the invention comprises a light chain variable (VL) region of the antigen-binding region that binds to CD30 as defined herein, wherein the sequences comprises, in total, at the most 1, 2, 3, 4 or 5 amino acid substitutions, when compared with SEQ ID NO:14.

In a further embodiment, the first heavy chain variable region comprises the sequence set forth in SEQ ID NO:13 and the first light chain variable region comprises the sequence set forth in SEQ ID NO:14.

Such antigen-binding regions that are capable of binding human CD30 have been described i.a. in WO03059282 (Medarex), which is incorporated by reference herein.

The said antibody in accordance with the invention, may bind with an equilibrium dissociation constant KD between the antigen-binding region that binds to human CD30, and human CD30 is within the range of 0.1 to 20 nM, for example within the range of 0.5-5 nM, such as within the range of 1.5-2 nM (monovalent binding). Said binding affinity can be determined by biolayer interferometry.

In one embodiment, the antibody of the invention can also bind cynomolgus CD30 (SEQ ID NO:40).

As described above, the multispecific antibody according to the invention comprises an antigen-binding region capable of binding to human CD3. Furthermore, the invention provides an antibody according to the invention capable of binding human CD3ε (epsilon), such as human CD3ε (epsilon) as specified in SEQ ID NO:22. Such antigen-binding region is capable of binding human CD3ε (epsilon), as presented on a T cell, such as a primary human T cell.

As described, the antibody comprises a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively.

In one embodiment, the antigen-binding region that binds to CD3 comprises:
 a (second) heavy chain variable region (VH) comprising the sequence of SEQ ID NO: 15, or a sequence having at least 90%, at least 95%, at least 97%, or at least 99% amino acid sequence identity to the sequence of SEQ ID NO: 15; and,
 a (second) light chain variable region (VL) comprising the sequence of SEQ ID NO:16 or a sequence having at least 90%, at least 95%, at least 97%, or at least 99% amino acid sequence identity to the sequence of SEQ ID NO: 16.

In a further embodiment, the antibody according to the invention comprises a heavy chain variable (VH) region of the antigen-binding region that binds to CD3 as defined herein, wherein the sequences comprises, in total, at the most 1, 2, 3, 4 or 5 amino acid substitutions, when compared with SEQ ID NO:15.

In a further embodiment, the antibody according to the invention comprises a light chain variable (VL) region of the antigen-binding region that binds to CD3 as defined herein, wherein the sequences comprises, in total, at the most 1, 2, 3, 4 or 5 amino acid substitutions, when compared with SEQ ID NO:16.

In a further embodiment, the second heavy chain variable region comprises the sequence set forth in SEQ ID NO: 15 and the second light chain variable region comprises the sequence set forth in SEQ ID NO:16. In one embodiment, the X in SEQ ID NO:15 is an H. In another embodiment, the X in SEQ ID NO:15 is a G.

Such antigen-binding regions that are capable of binding human CD3 have been described i.a. in WO2015/001085 (Genmab), which is incorporated by reference herein. Variants hereof, such as variants comprising a VH CDR3 region as set forth in SEQ ID NO:9 wherein X is G, which has a lower affinity for human CD3 binding than the parental antibody wherein X is H, have been described in Example 2 of WO2017/009442 (Genmab), which is herewith incorporated by reference.

The said antibody in accordance with the invention, may bind with an equilibrium dissociation constant KD between the antigen-binding region that binds to human CD3, and human CD3 is within the range of 5 to 30 nM, such as between 10 and 20 nM (for monovalent binding).

In one embodiment, the antibody of the invention can also bind cynomolgus monkey CD3 (SEQ ID NO:43).

In a further embodiment, the multispecific antibody comprises:
 (i) a CD30 binding region comprising a first heavy chain variable region comprising the sequence set forth in SEQ ID NO:13 and a first light chain variable region comprising the sequence set forth in SEQ ID NO:14, and
 (ii) a CD3 binding region comprising a second heavy chain variable region comprising the sequence set forth in SEQ ID NO:15 and a second light chain variable region comprising the sequence set forth in SEQ ID NO: 16.

Antibody Formats

The multispecific antibody of the invention, may have two or more specificities, such as two or three or more specificities. Furthermore, the multispecific antibody may have more than one copy of the antigen-binding region for CD3 and/or CD30. For example, in one embodiment, the antibody has two antigen-binding regions capable of binding CD3, such as two identical binding regions that bind CD3. For example, in another embodiment, the antibody has two antigen-binding regions that bind CD30, such as two identical binding regions that bind CD30. An additional antigen-binding region may e.g. be present in the form of a scFv covalently linked to the constant region.

In a preferred embodiment, the multispecific antibody of the invention is a bispecific antibody. Many different formats and uses of bispecific antibodies are known in the art, and were reviewed by Kontermann; Drug Discov Today, 2015 July; 20(7):838-47 and; MAbs, 2012 March-April; 4(2):182-97 and by Labrijn et al. 2019 Nat Rev Drug Discov 18(8) 585-608. A bispecific antibody according to the present invention may not be limited to any particular bispecific format or method of producing it.

Examples of bispecific antibody molecules which may be used in the present invention comprise (i) a single antibody that has two arms comprising different antigen-binding regions; (ii) a single chain antibody that has specificity to two different targets, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')2 fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

Further examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof;

(v) Fab fusion molecules, wherein different Fab-fragments are fused together, fused to heavy-chain constant-domains, Fc-regions or parts thereof; and (vi) scFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), kappa/lambda Body™ molecules (NovImmune, WO2012023053) and CovX-body (CovX/Pfizer; Doppalapudi, V. R., et al 2007. Bioorg. Med. Chem. Lett. 17, 501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, U.S. Ser. No. 00/795,1918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to scFv/Fc Fusions (Pearce et al., Biochem Mol Biol Int. 1997 September; 42(6):1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-based DART) molecules (MacroGenics, WO2008157379, WO2010080538) and Dual(scFv)2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of scFv-, diabody-based and domain antibodies include but are not limited to Bispecific T Cell Engager (BiTE) molecules (Micromet, WO2005061547), Tandem Diabody molecules (TandAb) (Affimed) Le Gall et al., Protein Eng Des Sel. 2004 April; 17(4):357-66.), DART molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin scFv Fusion (Merrimack, WO2010059315) and COM-BODY molecules (Epigen Biotech, Zhu et al. Immunol Cell Biol. 2010 August; 88(6):667-75.), dual targeting nanobodies (Ablynx, Hmila et al., FASEB J. 2010) and dual targeting heavy chain only domain antibodies.

In one embodiment, the bispecific antibody of the present invention is a diabody, a cross-body, or a bispecific antibody obtained via a controlled Fab-arm exchange (such as described in WO2011131746 (Genmab)).

In one embodiment, the antibody of the present invention is a bispecific DuoBody® molecule (Genmab A/S, WO2011131746).

The multispecific, such as bispecific, antibody of the invention can be of any isotype. Exemplary isotypes include but are not limited to either of the human IgG1, IgG2, IgG3, and IgG4 isotypes. Preferably, the antibodies may be selected to be of the human IgG1 isotype, as shown in the examples. Either of the human light chain constant regions, kappa or lambda, or both may be used, e.g. the sequences set forth in SEQ ID N:53 and 54. For example, in one embodiment, the light chain involved in CD30 binding comprises a kappa constant region and the light chain involved in CD3 binding comprises a lambda constant region. In one embodiment, both heavy chains of an antibody of the present invention are of the IgG1 isotype. In one embodiment, the two heavy chains of a bispecific antibody are of the IgG1 and IgG4 isotypes, respectively. Preferably, bispecific antibodies may be selected to be of the human IgG1 isotype, as shown in the examples. Optionally, and preferably, the heavy chain and Fc region sequences thereof of the selected isotype, may be modified, preferably in the hinge, CH2 and/or CH3 region, to enable the generation of bispecific antibodies and/or introduce inertness.

In one embodiment, the multispecific antibody of the invention comprises an Fc region consisting of a first and second Fc polypeptide.

In one embodiment, the first Fc polypeptide and the first heavy chain variable region are comprised within the same polypeptide chain and wherein the second Fc polypeptide and the second heavy chain variable region are comprised within the same polypeptide chain.

The first and second Fc polypeptide may each be of any isotype, including any human isotype, such as an IgG1, IgG2, IgG3, IgG4, IgE, IgD, IgM, or IgA isotype or a mixed isotype. Preferably, the Fc region is a human IgG1, IgG2, IgG3, IgG4 isotype or a mixed isotype. In one embodiment, said Fc region is a human IgG1 Fc region.

In a further embodiment, the multispecific antibody is a full-length antibody as defined herein.

Antibodies according to the present invention may comprise modifications in the Fc region to render the antibody an inert, or non-activating, antibody. Hence, in the antibodies disclosed herein, one or both heavy chains may be modified so that the antibody induces Fc-mediated effector function to a lesser extent relative to an antibody which is identical, except that it does not comprise said modifications. The Fc-mediated effector function may be measured by determining Fc-mediated CD69 expression on T cells (i.e. CD69 expression as a result of CD3 antibody-mediated, Fcγ receptor-dependent CD3 crosslinking e.g. as described in WO2015001085), by binding to Fcγ receptors, by binding to C1q, or by induction of Fc-mediated cross-linking of FcγRs. In particular, the heavy chain constant sequences may be modified so that the Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. by flow cytometry as described in Example 3 of WO2015001085. Modifications of the heavy and light chain constant sequences may also result in reduced binding of C1q to said antibody. As compared to an unmodified antibody the reduction may be by at least 70%, at least 80%, at least 90%, at least 95%, at least 97%, or 100% and the C1q binding may be determined by ELISA. Further, the Fc region which may be modified so that said antibody mediates reduced Fc-mediated T-cell proliferation compared to an unmodified antibody by at least 50%, at least 60%, at least 70%, at least 80%, at least 90%, at least 99% or 100%, for example in a linear part of the curve, wherein said T-cell proliferation is measured in a PBMC-based functional assay.

A wide range of different non-activating antibody formats have been developed in which amino acid substitutions, and combinations thereof, have been introduced in the constant heavy chain region of an IgG1 isotype antibody to eliminate Fc-mediated effector functions (e.g. Chiu et al., Antibodies 2019 December; 8(4): 55; Liu et al., Antibodies, 2020 Nov. 17; 9(4):64; 29(10):457-66; Shields et al., J Biol Chem. 2001 Mar. 2; 276(9):6591-604).

Examples of amino acid positions that may be modified, e.g. in an IgG1 isotype antibody, include positions L234 and L235. In one embodiment, the first and/or second Fc polypeptide comprise(s) a substitution of an amino acid corresponding to the amino acid at positions L234 and/or L235 in a human IgG1 heavy chain, wherein the substitutions preferably are to F and E, respectively, wherein the amino acid positions are as defined by Eu numbering.

It is understood that in addition to modifications of amino acid positions L234 and L235, further positions may be modified. Thus, in a further embodiment, the first and second Fc polypeptides comprise substitutions of the amino acids corresponding to the amino acids at positions L234 and L235 to F and E, respectively, and the first and/or second Fc polypeptide further comprises a substitution of an amino acid corresponding to the amino acid at position G236 in a human IgG1 heavy chain, wherein the substitution preferably is to R.

In another embodiment, the first and second Fc polypeptides comprise substitutions of the amino acids corresponding to the amino acids at positions L234 and L235 to F and E, respectively, and the first and/or second Fc polypeptide further comprises a substitution of an amino acid corresponding to the amino acid at position D265 in a human IgG1 heavy chain, wherein the substitution preferably is to A.

In another embodiment, the first and second Fc polypeptides comprise substitutions of the amino acids corresponding to the amino acids at positions L234 and L235 to F and E, respectively, and the first and second Fc polypeptide further comprises a substitution of an amino acid corresponding to the amino acid at position D265 in a human IgG1 heavy chain, wherein the substitution preferably is to A.

In another embodiment, one of the first and second Fc polypeptides comprises substitutions of the amino acids corresponding to the amino acids at positions L234, L235 and G236 to F, E and R, respectively, and the other Fc polypeptide comprises substitutions of the amino acids corresponding to the amino acids at positions L234, L235E and D265 to F, E and A, respectively.

In a further embodiment, the first Fc polypeptide comprises substitutions of the amino acids corresponding to the amino acids at positions L234, L235 and G236 to F, E and R, respectively, and the second Fc polypeptide comprises substitutions of the amino acids corresponding to the amino acids at positions L234, L235E and D265 to F, E and A, respectively, wherein the amino acid positions are as defined by Eu numbering.

For example, constant regions having such Fc region substitutions are provided i.a. in SEQ ID NO. 45, 46, 49, 50, 51 and 52, which can be compared with SEQ ID NO. 44, which does not have such substitution(s). In one embodiment, the antibody of the invention comprises a sequence selected from the group consisting of SEQ ID NO:45, 46, 49, 50, 51 and 52.

In one embodiment, the multispecific or bispecific antibody of the invention comprises an Fc region comprising first and second CH3 regions that are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference. Stable, heterodimeric antibodies can be obtained at high yield for instance by so-called Fab-arm exchange as provided in WO 2008/119353 and WO 2011/131746, on the basis of two homodimeric starting antibodies containing only a few, asymmetrical mutations in the CH3 regions.

In particular embodiments, the invention provides an antibody, wherein the amino acid in the position corresponding to K409 in a human IgG1 heavy chain is R in said first Fc polypeptide, and the amino acid in the position corresponding to F405 in a human IgG1 heavy chain is L in said second Fc polypeptide, or vice versa.

In a further embodiment, the amino acid in the position corresponding to K409 is R in the first Fc polypeptide and wherein the amino acid in the position corresponding to F405 is L in the second Fc polypeptide.

Hence, in one embodiment, in the first Fc polypeptide, at least one of the amino acids in the positions corresponding to a position selected from the group consisting of: T366, L368, K370, D399, F405, Y407 and K409 in a human IgG1 heavy chain has been substituted, and in the second Fc polypeptide at least one of the amino acids in the positions corresponding to a position selected from the group consisting of: T366, L368, K370, D399, F405, Y407 and K409 in a human IgG1 heavy chain has been substituted, and wherein said substitutions in the first and second Fc polypeptides are not in the same positions, wherein the amino acid positions are as defined by Eu numbering. For example, constant regions having such Fc region substitutions are provided i.a. in SEQ ID NO. 47, 48, 49, 50, 51 and 52, which can be compared with SEQ ID NO. 44, which does not have such a substitution. In one embodiment, the antibody of the invention comprises a sequence selected from the group consisting of SEQ ID NO: 47, 48, 49, 50, 51 and 52.

Preferably, the amino acid in the position corresponding to F405 is L in the first Fc polypeptide and the amino acid in the position corresponding to K409 is R in the second Fc polypeptide, or vice versa.

Thus, in one embodiment, one of the first and second Fc polypeptides comprises substitutions of the amino acids corresponding to the amino acids at positions L234, L235, G236 and F405 to F, E, R and L, respectively, and the other Fc polypeptide comprises substitutions of the amino acids corresponding to the amino acids at positions L234, L235E, D265 and K409 to F, E, A and R, respectively.

In another embodiment, one of the first and second Fc polypeptides comprises substitutions of the amino acids corresponding to the amino acids at positions L234, L235, G236 and K409 to F, E, R and R, respectively, and the other Fc polypeptide comprises substitutions of the amino acids corresponding to the amino acids at positions L234, L235E, D265 and F405 to F, E, A and L, respectively.

In a further embodiment, the invention relates to a multispecific antibody comprising:
  (i) a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively, and
  (ii) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively;
wherein the multispecific antibody is a bispecific antibody and comprises an Fc region consisting of a first and second Fc polypeptide;
wherein the first Fc polypeptide and the first heavy chain variable region are comprised within the same polypeptide chain and wherein the second Fc polypeptide and the second heavy chain variable region are comprised within the same polypeptide chain;
wherein the first Fc polypeptide comprises substitutions of the amino acids corresponding to the amino acids at positions L234, L235 and G236 to F, E and R, respectively, and the second Fc polypeptide comprises substitutions of the amino acids corresponding to the amino acids at positions L234, L235 and D265 to F, E and A, respectively, wherein the amino acid positions are as defined by Eu numbering; and
wherein the amino acid in the position corresponding to K409 is R in the first Fc polypeptide and wherein the amino acid in the position corresponding to F405 is L in the second Fc polypeptide.

In a further embodiment, the invention relates to a multispecific antibody comprising:
  (i) a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively, and
  (ii) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively;
wherein the multispecific antibody is a bispecific antibody and comprises an Fc region consisting of a first and second Fc polypeptide;
wherein the first Fc polypeptide and the first heavy chain variable region are comprised within the same polypeptide chain and wherein the second Fc polypeptide and the second heavy chain variable region are comprised within the same polypeptide chain;
wherein the first Fc polypeptide comprises substitutions of the amino acids corresponding to the amino acids at positions L234, L235 and D265 to F, E and A, respectively, and the second Fc polypeptide comprises substitutions of the amino acids corresponding to the amino acids at positions L234, L235 and D265 to F, E and A, respectively, wherein the amino acid positions are as defined by Eu numbering; and
wherein the amino acid in the position corresponding to K409 is R in the first Fc polypeptide and wherein the amino acid in the position corresponding to F405 is L in the second Fc polypeptide.

In one embodiment, the antibody of the invention comprises or consists of the heavy chain sequences set forth in SEQ ID NO:17 and 19 and the light chain sequences set forth in SEQ ID NO:18 and 20.

In a further embodiment, the antibody of the invention comprises or consists of the heavy chain sequences set forth in SEQ ID NO: 17 and 19 and the light chain sequences set forth in SEQ ID NO:18 and 20, and said antibody is a bispecific antibody.

In one embodiment, the antibody of the invention comprises or consists of the heavy chain sequences set forth in SEQ ID NO: 17 and 35 and the light chain sequences set forth in SEQ ID NO:18 and 20.

In one embodiment, the antibody of the invention comprises or consists of the heavy chain sequences set forth in SEQ ID NO:55 and 19 and the light chain sequences set forth in SEQ ID NO:18 and 20.

In one embodiment, the antibody of the invention comprises or consists of the heavy chain sequences set forth in SEQ ID NO:55 and 35 and the light chain sequences set forth in SEQ ID NO:18 and 20.

In a still further embodiment, the antibody of the invention is bsG1-huCD3-FEAL×CD30-MDX060-FEAR or bsG1-huCD3-FEAL×CD30-MDX060-FERR. In an even further embodiment, the antibody of the invention is bsG1-huCD3-FEAL×CD30-MDX060-FERR.

The constant region sequences listed in SEQ ID NOs: 44-52 and 55 do not include a C-terminal lysine (K). However, in naturally occurring sequences found in humans from which these Fc regions are derived, such a C-terminal lysine may be present as part of the open reading frame. During cell culture production of recombinant antibodies, this terminal lysine may be cleaved off by proteolysis by endogenous carboxypeptidase(s), resulting in a constant region having the same sequence but lacking the C-terminal lysine. For manufacturing purposes of antibodies, the DNA encoding this terminal lysine may be omitted from the sequence such that antibodies are produced without the lysine. Omission of the C-terminal lysine from the sequence encoding the antibody may increase the homogeneity of the antibody with respect to the presence of C-terminal lysine. Antibodies produced from nucleic acid sequences that either do, or do not encode a terminal lysine are substantially identical in sequence and in function since the degree of processing of the C-terminal lysine is typically high when e.g. using antibodies produced in CHO-based production systems (Dick, L. W. et al. Biotechnol. Bioeng. 2008; 100: 1132-1143). Hence, it is understood that antibodies in accordance with the invention can be generated without encoding or having a C-terminal lysine such as listed herein. For manufacturing purposes, antibodies can thus be generated without having a C-terminal lysine.

In alternative embodiments, the multispecific antibody according to the invention in not a classical full-length antibody comprising an Fc region. For example, in one embodiment, (i) the CD30 binding region and/or the CD3 binding region is a Fab,
(ii) the CD30 binding region and/or the CD3 binding region is an scFv,
(iii) the CD30 binding region is Fab and the CD3 binding region is an scFv, or
(iv) the CD30 binding region is an scFv and the CD3 binding region is a Fab.

Binding, Cytotoxicity and T-Cell Activation

Antibodies, such as bispecific antibodies, as described herein that can bind to human CD3 and human CD30 can advantageously target T cells to human CD30 expressing cancer cells, thereby inducing T-cell mediated killing of said cancer cells.

As said, preferably, the antibody in accordance with the invention is inert, and furthermore, the antibody comprises one or more of the following characteristics:

a) is capable of binding to CD30-expressing human tumor cells, such as SU-DHL-1 cells, SUP-M2 cells, DL-40 cells, KARPAS-299 cells, L-82 cells, SR-786 cells, L-540 cells, KM-H2 cells, L-1236 cells, JVM-2 cells, HH cells, NCEB-1 cells and/or HDLM-2 cells, when tested using flow cytometry, for example as described in the Examples herein,
b) is capable of mediating concentration-dependent cytotoxicity of CD30-expressing human tumor cells when using e.g., purified PBMCs, ADCC effector cells or T cells as effector cells when assayed as described in the Examples herein,
c) is capable of mediating concentration-dependent cytotoxicity of one or more human CD30-expressing tumor cell lines selected from the group consisting of: SU-DHL-1 cells, L-428 cells, KM-H2 cells, SUP-M2 cells, KI-JK cells and HDLM-2 cells, when using e.g., purified PBMCs or T cells as effector cells when assayed as described in the Examples herein,
d) is capable of inducing proliferation of T cells in vitro in the presence of CD30-expressing human tumor cells; e.g. when assayed as described in the Examples herein,
e) is capable of activating T cells in vitro in the presence of one or more CD30-expressing human tumor cell lines selected from the group consisting of: SU-DHL-1 cells, L-428 cells, KI-JK cells, and HDLM-2 cells, when assayed as described in the Examples herein,
f) is capable of inducing a dose-dependent production in vitro by T cells of cytokines and Granzyme B, when assayed as described in the examples herein,
g) is capable of not resulting in fratricide of T cells even though CD30 is expressed on a subpopulation of activated T cells, when assayed as described in the examples herein, and/or
h) is capable of inducing T cell mediated cytotoxicity even in the presence of sCD30, when assayed as described in the examples herein.

In one embodiment, the antibody as described herein induces T-cell mediated cytotoxicity with an $EC_{50}$ concentration below 0.050 µg/ml, such as below 0.045 µg/ml, like below 0.040 µg/ml, such as below 0.035 µg/ml, like below 0.030 µg/ml, such as below 0.025 µg/ml, like below 0.020 µg/ml, when assayed as described in the Examples herein, such as using L-428 tumor cells and measuring by flow cytometry.

In a further embodiment, the antibody as described herein has a maximum lysis when inducing T-cell mediated cytotoxicity above 80%, such as above 85%, like above 90%, when assayed as described in the Examples herein, such as using L-428 tumor cells and measuring by flow cytometry.

In one embodiment, the antibody as described herein induces $CD4^+$ T cell activation having an $EC_{50}$ concentration of CD25 expression below 0.05 µg/ml, such as below 0.045 µg/ml, like below 0.04 µg/ml, such as below 0.035 µg/ml, like below 0.03 µg/ml, when assayed as described in the Examples herein, such as using L-428 tumor cells and measuring by flow cytometry. In a further embodiment, the antibody as described herein induces $CD8^+$ T cell activation having an $EC_{50}$ concentration of CD25 expression below 0.005 µg/ml, such as below 0.001 µg/ml, like below 0.0009 µg/ml, such as below 0.0008 µg/ml, like below 0.0007 µg/ml, when assayed as described in the Examples herein, such as using L-428 tumor cells and measuring by flow cytometry.

In one embodiment, the antibody as described herein induces $CD4^+$ T cell activation having an $EC_{50}$ concentration of CD69 expression below 0.004 µg/ml, such as below 0.003 µg/ml, like below 0.002 µg/ml, such as below 0.001 µg/ml, like below 0.0009 µg/ml, when assayed as described in the Examples herein, such as using L-428 tumor cells and measuring by flow cytometry. In a further embodiment, the antibody as described herein induces $CD8^+$ T cell activation having an $EC_{50}$ concentration of CD69 expression below 0.0035 µg/ml, such as below 0.0030 µg/ml, like below 0.0025 µg/ml, such as below 0.0020 µg/ml, like below 0.0015 µg/ml, when assayed as described in the Examples herein, such as using L-428 tumor cells and measuring by flow cytometry.

In one embodiment, the antibody as described herein induces $CD4^+$ T cell activation having an $EC_{50}$ concentration of PD-1 expression below 0.01 µg/ml, such as below 0.008 µg/ml, like below 0.007 µg/ml, such as below 0.006 µg/ml, like below 0.005 µg/ml, when assayed as described in the Examples herein, such as using L-428 tumor cells and measuring by flow cytometry. In a further embodiment, the antibody as described herein induces $CD8^+$ T cell activation having an $EC_{50}$ concentration of PD-1 expression below 0.007 µg/ml, such as below 0.006 µg/ml, like below 0.005 µg/ml, such as below 0.004 µg/ml, like below 0.003 µg/ml, when assayed as described in the Examples herein, such as using L-428 tumor cells and measuring by flow cytometry.

The assays may be performed as commonly known to the skilled person and may optionally, comprise a ratio of effector cells to target cells (E:T) of 4:1 and/or optionally, an incubation period of 72 hrs. The assays could for example be performed by providing tumor cells, preferably labelled tumor cells, such as L-428 tumor cells; adding the antibody as described herein, preferably in a serial dilution; providing T cells, preferably labelled T cells, in a ratio of effector to target being E:T of 4:1 and incubating for 72 hrs; optionally, staining for relevant parameters such as CD4, CD8, CD25, CD69 and/or PD-1, and finally analysing the cells using flow cytometry like FACS. % live cells and/or T cell proliferation/activation may be calculated from the data obtained by the analysis as commonly known to the persons skilled in the art.

Production of Antibodies of the Invention

Traditional methods such as the hybrid hybridoma and chemical conjugation methods (Marvin and Zhu (2005) Acta Pharmacol Sin 26:649) can be used in the preparation of the multispecific, such as bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

As mentioned, strategies favoring the formation of a functional bispecific, product, upon co-expression of different antibody constructs can also be used, e.g., the method described by Lindhofer et al. (1995 J Immunol 155:219). Fusion of rat and mouse hydridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing the bispecific CD3× CD30 antibodies of the present invention includes methods described in WO2011131746 and WO13060867 (Genmab) comprising the following steps:

a) providing a first antibody comprising an Fc region, said Fc region comprising a first CH3 region;

b) providing a second antibody comprising a second Fc region, said Fc region comprising a second CH3 region, wherein the first antibody is a CD30 antibody and the second antibody is a CD3 antibody, or vice versa;

wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific CD3×CD30 antibody.

Similarly, the invention relates to a method for producing a multispecific, such as a bispecific, antibody according to the invention, comprising a) providing a first homodimeric antibody comprising the CD30 binding region as described herein, and a second homodimeric antibody comprising the CD3 binding region as described herein, wherein said antibodies comprise an Fc region and optionally contain further features described herein, wherein the sequences of the first and second CH3 regions of the first and second antibodies are different and are such that the heterodimeric interaction between the first and second CH3 regions is stronger than each of the homodimeric interactions of the first and second CH3 regions;

b) incubating the first antibody together with the second antibody under reducing conditions sufficient to allow the cysteines in the hinge regions to undergo disulfide-bond isomerization; and c) obtaining a heterodimeric multispecific antibody of the invention as described herein, comprising the first immunoglobulin heavy chain and the first immunoglobulin light chain of the first antibody and the second immunoglobulin heavy chain and the second immunoglobulin light chain of the second antibody.

In one embodiment, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a preferred embodiment, the reducing agent is 2-mercaptoethylamine. In a further embodiment, step c) comprises restoring the conditions to become non-reducing or less reducing, for example by removal of a reducing agent, e.g. by desalting.

In a further aspect, the invention relates to a monospecific antibody comprising
  (i) a CD30 binding region comprising a first heavy chain variable region comprising the CDR1, CDR2 and CDR3 sequences set forth in SEQ ID NO:1, 2 and 3, respectively, and a first light chain variable region comprising the CDR1, CDR2 and CDR3 sequences set forth in SEQ ID NO:4, the sequence AAS and SEQ ID NO:6, respectively, and
  (ii) an Fc region consisting of a first and second Fc polypeptide wherein the first and second Fc polypeptides comprise substitutions of the amino acids corresponding to the amino acids at positions L234 and L235 to F and E, respectively, and wherein the first and second Fc polypeptide further comprise a substitution of an amino acid corresponding to the amino acid at position G236 in a human IgG1 heavy chain, wherein the substitution preferably is to R, wherein the amino acid positions are as defined by Eu numbering.

In one embodiment, the first heavy chain variable region comprises the sequence set forth in SEQ ID NO: 13 and the first light chain variable region comprises the sequence set forth in SEQ ID NO:14.

In a further aspect, the invention relates to a monospecific antibody comprising
  (i) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively, and
  (ii) an Fc region consisting of a first and second Fc polypeptide wherein the first and second Fc polypeptides comprise substitutions of the amino acids corresponding to the amino acids at positions L234 and L235 to F and E, respectively, and wherein the first and second Fc polypeptide further comprise a substitution of an amino acid corresponding to the amino acid at position G236 in a human IgG1 heavy chain, wherein the substitution preferably is to R, wherein the amino acid positions are as defined by Eu numbering.

In one embodiment, X in SEQ ID NO:9 is an H. In another embodiment, X in SEQ ID NO:9 is a G. In one embodiment, the second heavy chain variable region comprises the sequence set forth in SEQ ID NO: 15 and the second light chain variable region comprises the sequence set forth in SEQ ID NO:16.

In one embodiment, the above-mentioned monospecific antibodies are full-length antibodies. Preferably, at least one of the amino acids in the positions corresponding to a position selected from the group consisting of: T366, L368, K370, D399, F405, Y407 and K409 in a human IgG1 heavy chain has been substituted, wherein preferably, the amino acid in the position corresponding to F405 is L or the amino acid in the position corresponding to K409 is R.

In a further aspect, the invention relates to a method for producing a multispecific antibody, comprising
  a) providing a first monospecific CD30 antibody as described herein above and a second antibody comprising
    (i) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively, and
    (ii) an Fc region consisting of a first and second Fc polypeptide wherein the first and second Fc polypeptides comprise substitutions of the amino acids corresponding to the amino acids at positions L234 and L235 to F and E, respectively, and a substitution of an amino acid corresponding to the amino acid at position D265 to A in a human IgG1 heavy chain
or
providing a second monospecific CD3 antibody as described herein above and a first antibody comprising
    (i) a CD30 binding region comprising a second heavy chain variable region comprising the CDR1, CDR2 and CDR3 sequences set forth in SEQ ID NO:1, 2 and 3, respectively, and a second light chain variable region comprising the CDR1, CDR2 and CDR3 sequences set forth in SEQ ID NO:4, the sequence AAS and SEQ ID NO:6, respectively, and
    (ii) an Fc region consisting of a first and second Fc polypeptide wherein the first and second Fc polypeptides comprise substitutions of the amino acids corresponding to the amino acids at positions L234 and L235 to F and E, respectively, and a substitution of an amino acid corresponding to the amino acid at position D265 to A in a human IgG1 heavy chain
wherein the sequences of the first and second CH3 regions of the first and second antibodies are different and are such that the heterodimeric interaction between the first and second CH3 regions is stronger than each of the homodimeric interactions of the first and second CH3 regions; wherein preferably the amino acid in the position corresponding to F405 is L in the first CH3 region and the amino acid in the position corresponding to K409 is R in the second CH3 region, or vice versa,
  b) incubating the first antibody together with the second antibody under reducing conditions sufficient to allow the cysteines in the hinge regions to undergo disulfide-bond isomerization; and
  c) obtaining the multispecific antibody comprising the first immunoglobulin heavy chain and the first immunoglobulin light chain of the first antibody and the second immunoglobulin heavy chain and the second immunoglobulin light chain of the second antibody.

In one embodiment, the present invention relates to a method for producing a multispecific antibody as described herein, comprising
  a) providing a first monospecific CD30 antibody as described herein and a second antibody comprising
    (i) a CD3 binding region comprising a second heavy chain variable region comprising the CDR1, CDR2 and CDR3 sequences set forth in SEQ ID NO:7, 8 and 9, respectively, and a second light chain variable region comprising the CDR1, CDR2 and CDR3 sequences set forth in SEQ ID NO:10, the sequence GTN and SEQ ID NO:12, respectively, and
    (ii) an Fc region consisting of a first and second Fc polypeptide wherein the first and second Fc polypeptides comprise substitutions of the amino acids corresponding to the amino acids at positions L234 and L235 to F and E, respectively, and a substitution of an amino acid corresponding to the amino acid at position D265 to A in a human IgG1 heavy chain, wherein the sequences of the first and second CH3 regions of the first and second antibodies are different and are such that the heterodimeric interaction between the first and second CH3 regions is stronger than each of the homodimeric interactions of the first and second CH3 regions; wherein preferably the amino acid in the position corresponding to K409 is R in the first CH3 region and the amino acid in the position corresponding to F405 is L in the second CH3 region, b) incubating the first antibody together with the second antibody under reducing conditions sufficient to allow the cysteines in the hinge regions to undergo disulfide-bond isomerization; and c) obtaining the multispecific antibody comprising the first immunoglobulin heavy chain and the first immunoglobulin light chain of the first antibody and the second immunoglobulin heavy chain and the second immunoglobulin light chain of the second antibody.

The present invention further relates to a multispecific antibody obtained by a method as described herein.

In the above methods, the steps of providing a first or second homodimeric antibody capable of binding to CD30 and/or CD3, may comprise the steps of providing cells containing expression vectors for producing said antibody or said antibodies; and allowing the cells to produce said antibody or said antibodies and subsequently, obtaining said antibody or said antibodies, thereby providing said antibody or said antibodies.

In one embodiment of this method, said first and/or second homodimeric antibodies are full-length antibodies.

The Fc regions of the first and second homodimeric antibodies may be of any isotype, including, but not limited to, IgG1, IgG2, IgG3 or IgG4. In one embodiment of this method, the Fc regions of both said first and said second homodimeric antibodies are of the IgG1 isotype. In another embodiment, one of the Fc regions of said homodimeric antibodies is of the IgG1 isotype and the other of the IgG4 isotype. In the latter embodiment, the resulting bispecific antibody comprises an Fc region of an IgG1 and an Fc region of IgG4 and may thus have interesting intermediate properties with respect to activation of effector functions.

In a further embodiment, one of the homodimeric starting antibodies has been engineered to not bind Protein A, thus allowing to separate the heterodimeric antibody from the homodimeric starting antibody by passing the product over a protein A column, removing the flow-through and eluting the heterodimeric antibody from the protein A column, to obtain a purified heterodimeric antibody composition.

As described above, the sequences of the first and second CH3 regions of the homodimeric starting antibodies may be different and such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific CD3×CD30 antibody can be obtained at high yield using the above method of the invention on the basis of two homodimeric starting antibodies which bind CD30 and CD3, respectively, and contain only a few, fairly conservative, asymmetrical mutations in the CH3 regions. Asymmetrical mutations mean that the sequences of said first and second CH3 regions contain amino acid substitutions at non-identical positions.

The multispecific, such as bispecific, antibodies of the invention may also be obtained by co-expression of constructs encoding the first and second polypeptides in a single cell.

Thus, in a further aspect, the invention relates to a nucleic acid construct, or a combination of nucleic acid constructs, encoding a multispecific antibody according to the invention and to an expression vector, or a combination of expression vectors, comprising such (a) nucleic acid construct(s).

Furthermore, the invention relates to a recombinant host cell capable of producing the multispecific antibody according to the invention, wherein the host cell comprises one or more nucleic acid constructs encoding the multispecific antibody according to the invention.

Accordingly, the invention also relates to a method for producing a multispecific antibody according to the invention, comprising (i) culturing a recombinant host cell of the invention under conditions wherein the antibody is produced, and (ii) isolating the produced multispecific antibody from the culture.

In one embodiment, said method comprises the following steps:

a) providing a first nucleic-acid construct encoding a first polypeptide comprising a first Fc region and a first antigen-binding region of a first antibody heavy chain, said first Fc region comprising a first CH3 region, b) providing a second nucleic-acid construct encoding a second polypeptide comprising a second Fc region and a second antigen-binding region of a second antibody heavy chain, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, optionally wherein said first and second nucleic acid constructs encode light chain sequences of said first and second antibodies c) co-expressing said first and second nucleic-acid constructs in a host cell, and d) obtaining said heterodimeric protein from the cell culture.

Preferably the encoded amino acid in the position corresponding to F405 is L in the first CH3 region and the encoded amino acid in the position corresponding to K409 is R in the second CH3 region, or vice versa.

Suitable expression vectors, including promoters, enhancers, etc., and suitable host cells for the production of antibodies are well-known in the art. Examples of host cells include yeast, bacterial and mammalian cells, such as Chinese hamster ovary cell (CHO) or human, such as human embryonic kidney (HEK), cells.

The nucleic acid, or one or more nucleic acids, as defined herein can be RNA or DNA. The nucleic acid, or one or more nucleic acids, as defined herein may be for use in expression in mammalian cells. Hence, furthermore the invention provides for a cell or cells, comprising a nucleic acid, or comprising one or more nucleic acids, as defined herein.

The nucleic acid in the context of the present invention may be an expression vector, which may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a CD30 or a CD3 antibody-encoding nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaP04-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the CD30 antibody and/or the CD3 antibody in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison WI) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

A nucleic acid and/or expression vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides. The nucleic acid and/or expression vector may comprise any suitable elements facilitating expression, i.e. transcription and/or translation of the nucleic acid such that the components of the (bispecific) antibodies are expressed. The nucleic acid and/or vector be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

Compositions and (Medical) Uses

Furthermore, the invention provides for a composition comprising an antibody as defined herein. Preferably, such a composition is a pharmaceutical composition, i.e. the antibody is comprised in a pharmaceutically-acceptable carrier.

A pharmaceutical composition may be formulated in accordance with conventional techniques such as those disclosed in Remington: The Science and Practice of Pharmacy, 19th Edition, Gennaro, Ed., Mack Publishing Co., Easton, PA, 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

The pharmaceutical composition may be administered by any suitable route and mode. In one embodiment that pharmaceutical composition is administered by intravenous or subcutaneous injection or infusion.

The antibody, composition, or pharmaceutical composition in accordance with the invention is preferably for use as a medicament.

The antibody, composition, or pharmaceutical composition in accordance with the invention is preferably for use in the treatment of disease.

In particular, the bispecific antibodies of the invention may be used for the treatment of various forms of cancer.

In one aspect, the present invention provides a method for treating a cancer in a subject, which method comprises administration of a therapeutically effective amount of a multispecific antibody of the present invention. In a further embodiment, the present invention provides a method for treating a disorder involving cells expressing CD30, in a subject, which method comprises administration of a therapeutically effective amount of a multispecific antibody of the present invention.

As said, suitable diseases that can be contemplated in methods and uses in accordance with the invention are cancer. Said cancer most preferably is characterized by expression of CD30. Expression of CD30 in a cancer can easily be determined using methods known in the art, such as PCR, immunostaining, or FACS analysis, i.e. detecting expression of CD30 transcript and/or protein. The antibodies as described herein that are capable of binding to human CD30 may be used e.g. in immunostaining and/or FACS analysis or the like.

In one aspect, the invention relates to the multispecific antibody, composition or pharmaceutical composition according to the invention for use in the treatment of Hodgkin's lymphoma or anaplastic large cell lymphoma.

In a further aspect, the invention relates to the multispecific antibody, composition or pharmaceutical composition according to the invention for use in the treatment of Hodgkin's lymphoma (HL) or Non-Hodgkin's lymphoma (NHL).

In one embodiment, the Hodgkin's lymphoma is a classical Hodgkin's lymphoma (cHL), In one embodiment, the Non-Hodgkin's lymphoma is a T cell Non-Hodgkin's lymphoma (T-NHL) or a B cell Non-Hodgkin's lymphoma (B-NHL). In a further embodiment, the Non-Hodgkin's lymphomas is a T cell Non-Hodgkin's lymphoma (T-NHL).

In a further embodiment, the T cell Non-Hodgkin's lymphoma is a peripheral T-cell lymphoma (PTCL) or a cutaneous T-cell lymphoma (CTCL). In a still further embodiment, the T cell Non-Hodgkin's lymphoma (T-NHL) is anaplastic large cell lymphoma (ALCL). In a still further embodiment, the peripheral T-cell lymphoma (PTCL) is anaplastic large cell lymphoma (ALCL).

In one embodiment, the B cell Non-Hodgkin's lymphoma (B-NHL) is mantle cell lymphoma (MCL).

In an even further embodiment, the Hodgkin's lymphoma (HL) is relapsed and refractory Hodgkin's lymphoma. In a further embodiment, the Hodgkin's lymphoma (HL) is a CD30+ Hodgkin's lymphoma. In a still further embodiment, the Hodgkin's lymphoma (HL) is a relapsed and refractory CD30+ Hodgkin's lymphoma. In an even further embodiment, the Hodgkin's lymphoma (HL) is a relapsed and refractory CD30+ classical Hodgkin's lymphoma.

In an even further embodiment, the Non-Hodgkin's lymphoma (NHL) is relapsed and refractory Non-Hodgkin's lymphoma. In a further embodiment, the Non-Hodgkin's lymphoma (NHL) is a CD30+ Non-Hodgkin's lymphoma. In a still further embodiment, the Non-Hodgkin's lymphoma (NHL) is a relapsed and refractory CD30+ Non-Hodgkin's lymphoma.

In a further embodiment, the multispecific antibody, composition or pharmaceutical composition according to the invention for use in the treatment of Hodgkin's lymphoma (HL) or Non-Hodgkin's lymphoma (NHL) is or has been administered intravenously and/or subcutaneously, preferably subcutaneously.

In a further embodiment, a patient being diagnosed with cancer may be subjected to an assessment of CD30 expression in the cancer cells, and when CD30 is detected, which may be in the range from low to high, such a patient may be selected for treatment with an antibody in accordance with the invention. However, it may not necessarily be a requirement to include such an assessment in selecting a patient for treatment.

The multispecific antibodies of the present invention have numerous in vitro and in vivo diagnostic and therapeutic utilities involving the diagnosis and treatment of disorders involving cells expressing CD30. For example, the antibodies can be administered to cells in culture, e.g., in vitro or ex vivo, or to subjects, e.g., in vivo, to treat, prevent and/or to diagnose a variety of disorders. As used herein, the term "subject" is intended to include human and non-human individuals.

In one aspect, the invention relates to a diagnostic composition comprising a multispecific antibody according to any one of the embodiments as disclosed herein.

In one embodiment, the diagnostic composition is a companion diagnostic which is used to screen and select those patients who will benefit from treatment with the multispecific antibody.

Kits

The invention further provides a kit-of-parts comprising an antibody as disclosed above, such as a kit for use as a companion diagnostic/for identifying within a population of patients, those patients which have a propensity to respond to treatment with an antibody as defined herein above, or for predicting efficacy or anti-tumor activity of said antibody when used in treatment of a patient, the kit comprising an antibody as defined above; and instructions for use of said kit.

In one embodiment, the present invention provides a kit for diagnosis of cancer comprising a container comprising a multispecific CD3×CD30 antibody, and one or more reagents for detecting cross-linking of CD30 expressing cells and CD3 expressing cells. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

In a further aspect, the invention relates to a method for detecting whether cross-linking between CD30- and CD3-expressing cells occurs in a sample derived from a patient, upon administration of a multispecific antibody according to any one of the embodiments as disclosed herein, comprising the steps of:
 (i) contacting the sample with a multispecific antibody according to any one of the embodiments as disclosed herein under conditions that allow for formation of a complex between said bispecific antibody and the CD30-expressing cells and the CD3-expressing cells; and
 (ii) analyzing whether a complex has been formed.

Delivery of Nucleic Acid Constructs and Delivery Vehicles

In a further aspect, the invention relates to the administration of nucleic acid constructs encoding an antibody of the invention for in vivo expression. For in vivo expression of the nucleic acid encoding the antibody, said nucleic acid typically is administered in a form suitable for the nucleic acid to enter the cells of the subject. Different methods for delivering a nucleic acid for in vivo expression exist and include both methods involving mechanical and chemical means. For example, such methods may involve electroporation or tattooing the nucleic acid onto the skin (Patel et al., 2018, Cell Reports 25, 1982-1993). Other methods suitable for administration of the nucleic acid to a subject involve administration of the nucleic acid in a suitable formulation.

Thus, the present invention also relates to a delivery vehicle comprising a nucleic acid or combination of nucleic acids according to the present invention. In some embodiments said delivery vehicle may be a lipid formulation. The lipids of the formulation may be particle(s), such as a lipid nanoparticle(s) (LNPs). The nucleic acid or combination of nucleic acids of the present may be encapsulated within said particle, e.g. within said LNP. Different lipid formulations suitable for administration of a nucleic acid to a subject for in vivo expression are well known to a person skilled in the art. For example, said lipid formulation may typically comprise lipids, ionizable aminolipids, PEG-lipids, cholesterol or any combination thereof.

Various forms and methods for preparation of lipid formulations suitable for administration of a nucleic acid to a subject for expression of a therapeutic antibody are well known in the art. Examples of such lipid formulations include but are not limited to those described in US20180170866 (Arcturus), EP 2391343 (Arbutus), WO 2018/006052 (Protiva), WO2014152774 (Shire Human Genetics), EP 2 972 360 (Translate Bio), U.S. Ser. No. 10/195,156 (Moderna) and US20190022247 (Acuitas).

Accordingly, in a further aspect, the invention relates to (a) nucleic acid construct(s) according to the invention or a delivery vehicle according to the invention for use as a medicament, preferably for use in the treatment of cancer, such as in the treatment of Hodgkin's lymphoma or anaplastic large cell lymphoma.

The present invention is further illustrated by the following examples, which should not be construed as limiting the scope of the invention.

EXAMPLES

Example 1—Generation of CD3×CD30 Bispecific Antibodies by 2-MEA-Induced Fab-Arm Exchange The following antibodies were used in the examples:
Humanized CD3 Antibodies IgG1-huCD3-H1L1 as described in Example 1 of WO2015/001085 (Genmab). IgG1-huCD3-H1L1 is referred to herein as 'IgG1-huCD3'.

IgG1-huCD3-H1L1-H101G as described in Example 2 of WO2017/009442 (Genmab). IgG1-huCD3-H1L1-H101G is referred to herein as 'IgG1-huCD3-H101G'.

CD30 Antibodies

MDX-060, which is also referred to as HuMab 5F11, has been disclosed in WO2003/059282 (Medarex). hAC10 (or SGN-30) has been disclosed in U.S. Pat. No. 8,257,706 and US20100239571 (Seattle genetics). HRS-3 has been disclosed in WO2016/0177846 (Affimed). HeFi-I, T405, T105, T408, and T215 have been disclosed in WO 2007/040653 (US government & Health).

Antibody Expression

Antibody sequences were cloned into pcDNA3.3 expression vectors (Invitrogen, US) and expressed as IgG1, κ or IgG1, λ, with or without Fc-silencing and/or DuoBody® technology amino acid substitutions in the Fc domain (see below). All antibodies were produced under serum-free conditions by co-transfecting relevant heavy and light chain expression vectors in Expi293F™ cells (Thermo Fisher Scientific, US; cat. no. A14527) using ExpiFectamine™ 293 (Thermo Fisher Scientific; cat. no. A14525), essentially as described by the manufacturer.

Generation of Bispecific Antibodies

Bispecific antibodies were generated in vitro using the DuoBody® platform technology, i.e. 2-MEA-induced controlled Fab-arm exchange (cFAE) as described in WO2011147986, WO2011131746 and WO2013060867 (Genmab) and Labrijn et al. (Labrijn et al., PNAS 2013, 110: 5145-50; Gramer et al., MAbs 2013, 5: 962-973). To enable the generation of bispecific antibodies by this method, IgG1 molecules carrying a single mutation in the CH3 domain were generated: in one parental IgG1 antibody the F405L mutation (i.e. the CD3 antibodies or control, HIV-1 gp120-specific, antibodies), in the other parental IgG1 antibody the K409R mutation (i.e. the CD30 or control antibodies). In addition to these mutations, the parental IgG1 antibodies included substitutions that result in an Fc domain that is unable to interact with IgG Fc receptors (Fc gamma receptors) and/or complement factors such as C1q: L234F, L235E, D265A (FEA; US 2015/0337049) or L234F, L235E, G236R (FER).

The combination of Fc silencing and DuoBody® technology mutations were designated as follows:
L234F, L235E, D265A, and F405L: FEAL
L234F, L235E, D265A, and K409R: FEAR
L234F, L235E, G236R, and K409R: FERR The heavy chain (HC) and light chain (LC) sequences of the parental antibodies are set forth in the following SEQ ID NOs:

IgG1-huCD3-FEAL: SEQ ID NO:19 (HC) and SEQ ID NO:20 (LC).

IgG1-huCD3-H101G-FEAL: SEQ ID NO:35 (HC) and SEQ ID NO:20 (LC).

IgG1-CD30-MDX060-FERR: SEQ ID NO:17 (HC) and SEQ ID NO:18 (LC).

IgG1-CD30-MDX060-FEAR: SEQ ID NO:55 (HC) and SEQ ID NO:18 (LC).

IgG1-CD30-hAC10-FEAR: SEQ ID NO:21 (HC) and SEQ ID NO:22 (LC).

IgG1-CD30-HRS-3-FEAR: SEQ ID NO:23 (HC) and SEQ ID NO:24 (LC).

IgG1-CD30-HeFi-I-FEAR: SEQ ID NO:25 (HC) and SEQ ID NO:26 (LC).

IgG1-CD30-T405-FEAR: SEQ ID NO:27 (HC) and SEQ ID NO:28 (LC).

IgG1-CD30-T105-FEAR: SEQ ID NO:29 (HC) and SEQ ID NO:30 (LC).

IgG1-CD30-T408-FEAR: SEQ ID NO:31 (HC) and SEQ ID NO:32 (LC).

IgG1-CD30-T215-FEAR: SEQ ID NO:33 (HC) and SEQ ID NO:34 (LC).

To generate bispecific antibodies, the two parental antibodies were mixed in equal molar ratios in PBS buffer (Phosphate Buffered Saline; 8.7 mM $HPO_4^{2-}$, 1.8 mM $H_2PO_4^-$, 163.9 mM $Na^+$, 140.3 mM $Cl^-$, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer carriages (Thermo Fisher Scientific) according to the manufacturer's protocol. Samples were stored overnight at 4° C. to allow for the re-oxidation of the disulfide bonds and formation of intact bispecific antibodies. The efficacy of cFAE was >95% as assessed by electrospray ionization mass spectrometry mass spectrometry (ESI-MS) as described by Gramer et al. (MAbs. 2013 Nov. 1; 5(6): 962-973.).

Non-Binding Control Antibody b12

IgG1-b12 is a HIV-1 gp120 specific antibody (Barbas, CF. J Mol Biol. 1993 Apr. 5; 230(3):812-23) that is used in some of the examples as negative, non-binding control antibody. The sequence of the heavy chain and the sequence of the light chain are included herein as SEQ ID NOs: 36 and 37, respectively (FEAL) or SEQ ID NOs: 38 and 37, respectively (FERR).

Example 2—CD30 Expression in Human Hodgkin Lymphoma (HL), Anaplastic Large Cell Lymphoma (ALCL) and TLL Cell Lines CD30 surface expression levels were evaluated in a panel of HL, ALCL and TLL cell lines (Table 4) using quantitative flow cytometry (Human IgG Calibrator kit, Biocytex, cat no. CP010). Cells ($5 \times 10^4$ cells/well) were incubated in polystyrene 96-well round-bottom plates (Greiner bio-one, cat. no. 650180) with 10 μg/mL IgG1-CD30-MDX060-FERR in 50 μL staining buffer (PBS [Lonza, cat. no. BE17-517Q] supplemented with 0.1% bovine serum albumin [BSA, fraction V, Roche, cat, no. 10735086001] and 0.02% NaN3 [Sigma Aldrich, cat no. 13412]) at 4° C. for 30 min. In parallel, a standard curve was generated using a Human IgG Calibrator Kit (Biocytex, cat. no. CP010), essentially according to the manufacturer's instructions. Calibration beads, containing a well-defined number of human IgG monoclonal antibodies per bead, were incubated with the same R-PE-conjugated secondary antibody (Jackson ImmunoResearch, UK; cat. no. 109-116-098; 1:500 dilution) at 4° C. protected from light for 30 min. Cells and beads were washed in FACS buffer and analyzed by flow cytometry on a FACSCelesta flow cytometer (BD Biosciences, USA). The standard curve obtained using the Human IgG Calibrator Kit was used to interpolate the number of IgG1-CD30-MDX060-FERR antibodies bound per cell (ABC) using GraphPad Prism Software, representing an estimate of the number of CD30 molecules expressed on the cell surface.

Table 4 and 5 show that CD30 expression above the lower limit of quantification (LLOQ) was observed in all cell lines except for SUP-T1.

TABLE 4

Overview of cell lines and expression of CD30

| cell line | tumor type | Catalog | supplier | CD30 expression (ABCs) Median | Range | n |
|---|---|---|---|---|---|---|
| L-540 | HL | ACC 72 | DSMZ | 145,723 | 61,779-271,304 | 3 |
| L-428 | HL | ACC 197 | DSMZ | 120,725 | 102,787-133,437 | 3 |
| HDLM-2 | HL | CRL-2965 | ATCC | 56,578 | 51,737-87,841 | 3 |
| KM-H2 | HL | ACC 8 | DSMZ | 19,720 | 17,283-29,129 | 3 |
| NCEB-1 | MCL | CRL-3005 | ATCC | 15,406 | 11,102-18,333 | 3 |
| L-1236 | HL | ACC 530 | DSMZ | 4,548 | 4,054-4,838 | 3 |
| L-82 | ALCL | ACC 597 | DSMZ | 127,616 | 70,495-172,019 | 3 |
| SR-786 | ALCL | ACC 369 | DSMZ | 104,947 | 69,630-133,464 | 3 |
| KI-JK | ALCL | ACC 695 | DSMZ | 124,669 | 77,610-139,598 | 3 |
| DEL | ALCL | ACC 338 | DSMZ | 122,003 | 55,416-153,484 | 3 |
| SUP-M2 | ALCL | ACC 509 | DSMZ | 6,129 | 37,047-93,777 | 3 |
| SU-DHL-1 | ALCL | ACC 356 | DSMZ | 75,238 | 72,529-80,697 | 2 |
| HuT 78 | ALCL | TIB-161 | ATCC | 19,399 | 20,608-18,189 | 2 |
| SUP-T1 | TLL | CRL-1942 | ATCC | <LLOQ[a] | — | 3 |

TABLE 5

Overview of cell lines and average expression of CD30

| cell line | tumor type | Catalog | supplier | CD30 expression (ABCs) Average | Range | n |
|---|---|---|---|---|---|---|
| DEL | ALCL | ACC 338 | DSMZ | 110,301 | 55,416-153,484 | 3 |
| DL-40 | ALCL | JCRB1337 | JCRB | 98,174 | 60,392-156,229 | 3 |
| HDLM-2 | HL | CRL-2965 | ATCC | 64,510 | 51,737-87,841 | 3 |
| HH | CTCL | ACC 707 | DSMZ | 161,740 | 122,598-206,774 | 3 |
| HuT 78 | ALCL | TIB-161 | ATCC | 19,399 | 20,608-18,189 | 2 |
| JVM-2 | MCL | ACC 12 | DSMZ | 25,842 | 12,644-43,081 | 3 |
| KARPAS-299 | ALCL | 06072604 | PHE | 91,426 | 77,730-106,058 | 3 |
| KI-JK | ALCL | ACC 695 | DSMZ | 118,794 | 77,610-139,598 | 3 |
| KM-H2 | HL | ACC 8 | DSMZ | 22,044 | 17,283-29,129 | 3 |
| L-1236 | HL | ACC 530 | DSMZ | 4,480 | 4,054-4,838 | 3 |
| L-428 | HL | ACC 197 | DSMZ | 117,743 | 102,787-133,437 | 3 |
| L-540 | HL | ACC 72 | DSMZ | 159,602 | 61,779-271,304 | 3 |
| L-82 | ALCL | ACC 597 | DSMZ | 127,616 | 70,495-172,019 | 3 |
| NCEB-1 | MCL | CRL-3005 | ATCC | 14,947 | 11,102-18,333 | 3 |
| SR-786 | ALCL | ACC 369 | DSMZ | 104,497 | 69,630-133,464 | 3 |
| SU-DHL-1 | ALCL | ACC 356 | DSMZ | 76,613 | 72,529-80,697 | 2 |
| SUP-M2 | ALCL | ACC 509 | DSMZ | 66,129 | 37,047-93,777 | 3 |
| SUP-T1 | TLL | CRL-1942 | ATCC | <LLOQ[a] | — | 3 |

[a]<LLOQ, below lower limit of quantification (3300 ABCs)

Example 3—Binding of CD3×CD30 Bispecific Antibodies to Human Hodgkin Lymphoma (Hl) and Non-Hodgkin's Lymphoma (NHL) Such as Anaplastic Large Cell Lymphoma (ALCL) Cells Binding of CD3×CD30 bispecific antibodies to two CD30-expressing human tumor cell lines SU-DHL-1 (ALCL; ATCC, cat. no. ACC 356) and HDLM-2 (HL; ATCC, cat. no. CRL-2965) was analyzed by flow cytometry.

Cells ($3\times10^4$ cells/well) were incubated in polystyrene 96-well round-bottom plates (Greiner bio-one, cat. no. 650180) with serial dilutions of antibodies (range 0.0046 to 10 μg/mL in 3-fold dilution steps) in 50 μL staining buffer at 4° C. for 30 min. After washing twice in staining buffer, cells were incubated with 50 μL secondary antibody at 4° C. for 30 min. As a secondary antibody, R-PE-conjugated goat-anti-human IgG (Jackson ImmunoResearch, UK; cat. no. 109-116-098) diluted 1:400 in staining buffer was used. Next, cells were washed twice in staining buffer, resuspended in 100 μL staining buffer supplemented with TO-PRO-3 iodide (Thermo Fisher Scientific; cat. no. T3605; 1:8000 dilution) and analyzed on a FACSCelesta flow cytometer (BD Biosciences, USA). Live cells were gated based on FSC/SSC and absence of TOPRO-3 staining. Binding curves were analyzed by non-linear regression of log-transformed data (sigmoidal dose-response with variable slope, four parameters) using GraphPad Prism V7.02 software (GraphPad Software, San Diego, CA, USA).

Results

Figure 1D:
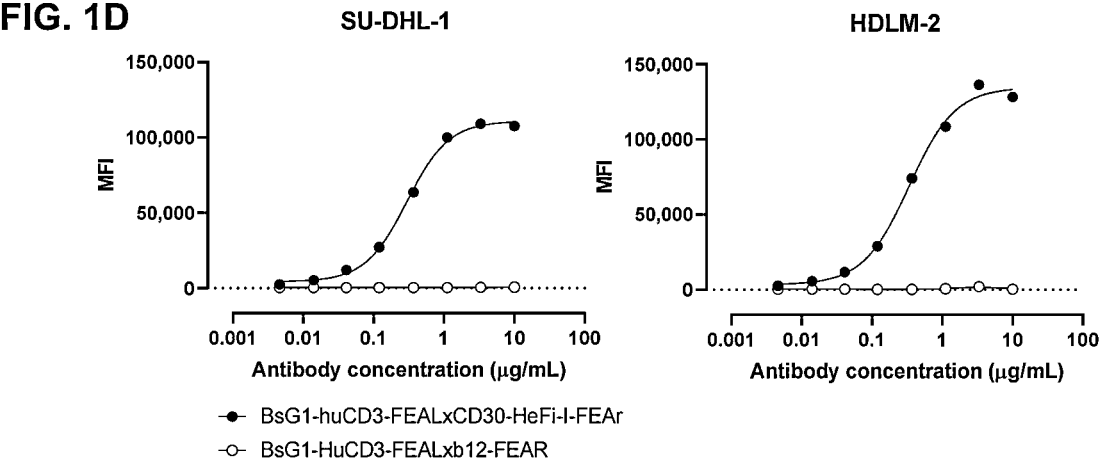
Figure 1E:
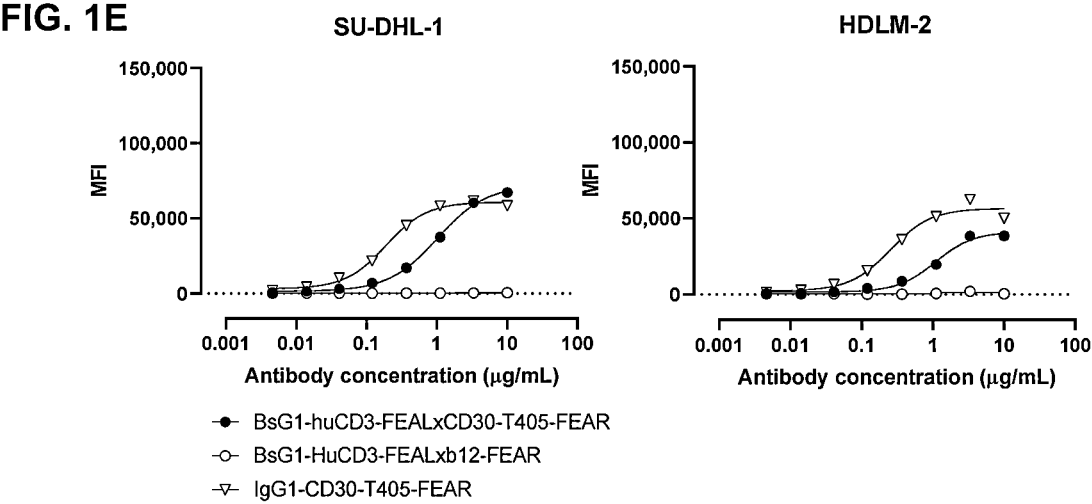
Figure 1F:
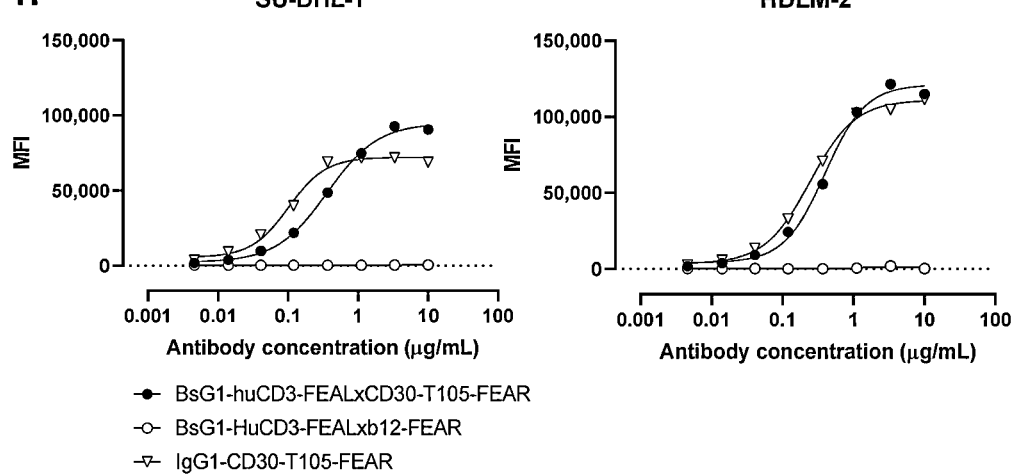

FIG. 1 shows dose-response binding curves of the CD3× CD30 bispecific antibodies bsG1-huCD3-FEAL×CD30-MDX060-FEAR (A), bsG1-huCD3-FEAL×CD30-hAC10-FEAR (B), bsG1-huCD3-FEAL×CD30-HRS-3-FEAR (C), BsG1-huCD3-FEAL×CD30-HeFi-I-FEAR (D), bsG1-huCD3-FEAL×CD30-T405-FEAR (E), bsG1-huCD3-FEAL×CD30-T105-FEAR (F), BisIgG1-huCD3-FEAL× CD30-T408-FEAR (G) and bsG1-huCD3-FEAL×CD30-T215-FEAR (H) to SU-DHL-1 (left panels) and HDLM-2 (right panels) tumor cells.

At a concentration of 1.11 μg/mL, bsG1-huCD3-FEAL× CD30-MDX060-FEAR, bsG1-huCD3-FEAL×CD30-hAC10-FEAR, bsG1-huCD3-FEAL×CD30-HRS-3-FEAR, and bsG1-huCD3-FEAL×CD30-T105-FEAR displayed similar binding when compared the binding of the monospecific, bivalent CD30 parental antibodies IgG1-CD30-MDX060-FEAR, IgG1-CD30-hAC10-FEAR, IgG1-CD30-HRS-3-FEAR and IgG1-CD30-T105-FEAR (FIG. 1I).

In contrast, at a concentration of 1.11 µg/mL, the binding of bsG1-huCD3-FEAL×CD30-T405-FEAR, bsG1-huCD3-FEAL×CD30-T408-FEAR and bsG1-huCD3-FEAL×CD30-T215-FEAR was lower than binding of the monospecific, bivalent CD30 parental antibodies IgG1-CD30-T405-FEAR, IgG1-CD30-T408-FEAR and IgG1-CD30-T215-FEAR to SU-DHL-1 and HDLM-2 cells (FIG. 1I).

Overall, binding of bsG1-huCD3-FEAL×CD30-MDX060-FEAR, bsG1-huCD3-FEAL×CD30-hAC10-FEAR, bsG1-huCD3-FEAL×CD30-HRS-3-FEAR, BsG1-huCD3-FEAL×CD30-HeFi-I-FEAR and bsG1-huCD3-FEAL×CD30-T105-FEAR at a concentration of 1.11 µg/mL was higher than binding of bsG1-huCD3-FEAL×CD30-T405-FEAR, bsG1-huCD3-FEAL×CD30-T408-FEAR and bsG1-huCD3-FEAL×CD30-T215-FEAR at the same concentration (FIG. 1I).

The negative control antibody BsG1-huCD3-FEAL×b12-FEAR that was included in these experiments did not show binding to SU-DHL-1 and HDLM-2 cells, indicating that neither SU-DHL-1 nor HDLM-2 cells express CD3.

In conclusion, CD30 antibody clones T405, T408 and T215 showed reduced binding in monovalent compared to bivalent format, while clones MDX060, hAC10, HRS-3 and T105 showed efficient binding to CD30-expressing tumor cells in both monovalent and bivalent format. FIG. 2 shows dose-response binding curves of bsG1-huCD3-FEAL×CD30-MDX060-FERR to (A) HDLM-2 (HL), (B) L-428 (HL), (C) DEL (ALCL), and (D) KI-JK (ALCL) cells. BsG1-huCD3-FEAL×CD30-MDX060-FERR displayed similar maximum binding when compared to the monospecific, bivalent CD30 parental antibody IgG1-CD30-MDX060-FERR. Negative control antibodies bsG1-huCD3-FEAL×b12-FEAR, IgG1-huCD3-FEAL, and IgG1-b12-FEAL did not show binding to any of these cell lines, indicating that these cells do not express CD3 on the cell surface. These data confirmed efficient binding of bsG1-huCD3-FEAL×CD30-MDX060-FEER to HL and ALCL cell lines.

Table 6 shows $EC_{50}$ values for binding of bsG1-huCD3-FEAL×CD30-MDX060-FEAR to HDLM-2, L-428, DEL, and KI-JK cells as evaluated in two independent experiments. $EC_{50}$ values ranged between 0.05 and 0.30 µg/mL.

TABLE 6

$EC_{50}$ values for binding of bsG1-huCD3×CD30-MDX060

| | $EC_{50}$ (µg/mL) | |
|---|---|---|
| Cell line | N = 1 | N = 2 |
| HDLM-2 | 0.1450 | 0.1197 |
| L-428 | 0.1539 | 0.0705 |
| DEL | 0.3018 | 0.0568 |
| KI-JK | 0.1602 | 0.0735 |

FIGS. 8, 9, and 10 show dose-response binding curves of bsG1-huCD3-FEAL×CD30-MDX060-FERR to CD30-expressing HL cell lines (FIG. 8), ALCL cell lines (FIG. 9), and NHL cell lines (FIG. 10). In all cell lines, BsG1-huCD3-FEAL×CD30-MDX060-FERR displayed similar maximum binding compared with the monovalent control antibody BsG1-b12-FEAL×CD30-MDX060-FERR. The monospecific, bivalent CD30 parental antibody IgG1-CD30-MDX060-FERR showed dose-dependent binding to all cell lines, but showed lower maximum binding compared with BsG1-huCD3-FEAL×CD30-MDX060-FERR. Negative control antibodies bsG1-huCD3-FEAL×b12-FEAR, IgG1-huCD3-FEAL, and IgG1-b12-FEAL did not show binding to any of these cell lines, indicating that these cells do not express CD3 on the cell surface. These data confirmed efficient binding of bsG1-huCD3-FEAL×CD30-MDX060-FERR to HL cell lines, T-NHL such as ALCL and CTCL cell lines; and B-NHL such as MCL cell line.

Table 7 shows $EC_{50}$ values for binding of bsG1-huCD3-FEAL×CD30-MDX060-FERR to HL, T-NHL, and B-NHL cell lines as evaluated in 2 or 3 independent experiments. $EC_{50}$ values ranged between 0.12 and 0.35 µg/mL.

TABLE 7

$EC_{50}$ values for binding of bsG1-huCD3-FEAL×CD30-MDX060-FERR

| Cell line | | CD30 Binding | | |
|---|---|---|---|---|
| Name | Cancer type | Average Binding EC50 | Range Binding $EC_{50}$ (µg/mL) | n tests |
| L-540 | HL | 0.3229 | 0.2020-0.4694 | 3 |
| L-428 | HL | 0.1743 | 0.1742-0.1744 | 2 |
| KM-H2 | HL | 0.1587 | 0.1405-0.1824 | 3 |
| L-1236 | HL | 0.2019 | 0.1628-0.2247 | 3 |
| HDLM-2 | HL | 0.1674 | 0.1253-0.2206 | 3 |
| L-82 | ALCL | 0.1999 | 0.1845-0.2153 | 2 |
| SR-786 | ALCL | 0.3279 | 0.1735-0.5499 | 3 |
| KI-JK | ALCL | 0.1914 | 0.1431-0.2582 | 3 |
| SUP-M2 | ALCL | 0.1667 | 0.1336-0.2225 | 3 |
| DL-40 | ALCL | 0.2364 | 0.1698-0.3472 | 3 |
| DEL | ALCL | 0.2011 | 0.1430-0.2674 | 3 |
| KARPAS-299 | ALCL | 0.2015 | 0.1343-0.2686 | 2 |
| SUP-T1 | TLL | 0.3458 | 0.2572-0.4344 | 2 |
| JVM-2 | MCL | 0.1257 | 0.1068-0.1411 | 3 |
| NCEB-1 | MCL | 0.1564 | 0.1180-0.2000 | 3 |
| HH | CTCL | 0.1951 | 0.1559-0.2425 | 3 |

Example 4—Induction of T-Cell Mediated Cytotoxicity and T-Cell Proliferation In Vitro by CD3×CD30 Bispecific Antibodies CD3×CD30 bispecific antibodies were tested in an in vitro cytotoxicity assay using CD30-positive tumor cell lines as target cells and T cells as effector cells. As a source of T cells, CD3-positive ADCC effector cells type IV (Clean Cells, Montaigu, France) or purified T cells (as described in Example 5) were used to evaluate CD3-dependent tumor cell kill.

SU-DHL-1 (ALCL), HuT78 (ALCL), HDLM-2 (HL), NCEB-1 (MCL), or L540 (HL) cells were seeded at a density of 10,000 cells/well into polystyrene 96-well round-bottom plates (Greiner bio-one, cat. no. 650180). Effector cells were labelled with 0.5 µM CFSE (carboxyfluorescein succinimidyl ester; Cell Signalling Technology, Danvers, MA; cat. no. C34554) at 37° C. for 20 min and added to tumor cells at an E:T ratio=10:1 (ADCC effector cells) or 7:1 (purified T cells). Serial dilutions of bispecific CD3×CD30, b12×CD30 or CD3×b12 antibodies, or monospecific, bivalent CD30 antibodies were added (final concentration ranging from 10 to 0.041 µg/mL; 3-fold dilutions) and cells were incubated for 72 hours at 37° C. In some experiments, a variant of bsG1-huCD3-FEAL×CD30-MDX060-FEAR was used with a CD3 binding arm containing the H101G mutation, which has with reduced affinity for CD3 (WO2017/009442, Genmab). After washing twice in 100 µL staining buffer, cells were resuspended in staining buffer containing TO-PRO-3 iodide (Thermo Fisher Scientific; cat. no. T3605; 1:4000 dilution) and analyzed on a FACSCelesta flow cytometer (BD Biosciences, USA).

The viability of tumor cell samples treated with 5 µM staurosporine (Sigma-Aldrich, US, cat. no. S6942) was set at 0% and the viability of untreated tumor cell samples was set at 100%.

The 'percentage viable cells' was calculated as follows: % viable cells=([cell number sample–cell number staurosporine treated target cells]/[cell number untreated target cells–cell number staurosporine treated target cells])×100. CFSE-positive cells were counted as a measure of absolute numbers of T cells to assess T-cell proliferation.

Dose-response curves were analyzed by non-linear regression (sigmoidal dose-response with variable slope) using GraphPad Prism V8 software (GraphPad Software, San Diego, CA, USA).

Results

CD3×CD30 bispecific antibodies were tested in an in vitro cytotoxicity assay using the CD30-positive tumor cell lines SU-DHL-1 cells or HDLM-2 cells as target cells and ADCC effector cells type IV cells (Clean Cells, Montaigu, France) as effector cells.

FIG. 3 shows that bsG1-huCD3-FEAL×CD30-MDX060-FEAR (A), bsG1-huCD3-FEAL×CD30-hAC10-FEAR (B), bsG1-huCD3-FEAL×CD30-HRS-3-FEAR (C), BsG1-huCD3-FEAL×CD30-HeFi-I-FEAR (D), bsG1-huCD3-FEAL×CD30-T405-FEAR (E), bsG1-huCD3-FEAL×CD30-T105-FEAR (F), bsG1-huCD3-FEAL×CD30-T408-FEAR (G), and bsG1-huCD3-FEAL×CD30-T215-FEAR (H) induced dose-dependent T-cell mediated cytotoxicity (shown as decrease in % viable cells) of SU-DHL-1 (left panels) or HDLM-2 (right panels) cells.

The monospecific, bivalent CD30 antibodies IgG1-MDX060-FEAR (A), IgG1-CD30-hAC10-FEAR (B), IgG1-CD30-HRS-3-FEAR (C), IgG1-CD30-HeFi-I-FEAR (D), IgG1-CD30-T405-FEAR (E), IgG1-CD30-T105-FEAR (F), IgG1-CD30-T408-FEAR (G), and IgG1-CD30-T215-FEAR (H) did not induce T-cell mediated cytotoxicity. Control antibody bsG1-huCD3-FEAL×b12-FEAR also did not induce T-cell mediated cytotoxicity of SU-DHL-1 or HDLM-2 cells.

In addition, CD3×CD30 bispecific antibodies were tested in an in vitro cytotoxicity assay using different MCL, ALCL and HL cell lines as target cells and purified T cells or ADCC effector cells type IV cells as effector cells. FIG. 4A-B show that T-cell mediated cytotoxicity of SU-DHL-1, HuT78, or NCEB-1 cells induced by bsG1-huCD3-FEAL×CD30-MDX060-FEAR is more potent compared to a variant of this antibody with a CD3 binding arm with reduced affinity (bsG1-huCD3-H101G-FEAL×CD30-MDX060-FEAR). Similar maximum T-cell mediated cytotoxicity of HDLM-2 cells was induced by bsG1-huCD3-FEAL×CD30-MDX060-FEAR and bsG1-huCD3-H101G-FEAL×CD30-MDX060-FEAR (FIG. 4B). Incubation with bivalent, monospecific antibodies IgG1-huCD3-FEAL or IgG1-b12-FEAR, which were included as controls, did not induce cytotoxicity in these cell lines. Potent and similar T-cell mediated cytotoxicity of L540 cells was induced by bsG1-huCD3-FEAL×CD30-MDX060-FEAR and bsG1-huCD3-H101G-FEAL×CD30-MDX060-FEAR at the lowest concentration tested (0.014 µg/mL; FIG. 4C). Control antibodies bsG1-b12-FEAL×CD30-MDX060-FEAR or IgG1-MDX060-FEAR did not induce T-cell mediated cytotoxicity of L540 cells.

In conclusion, bsG1-huCD3-FEAL×CD30-MDX060-FEAR induced potent killing of various CD30-expressing MCL, ALCL and HL tumor cell lines. BsG1-huCD3-FEAL×CD30-MDX060-FEAR that contains an H at position 101 of the VH CDR3 of the CD3 arm is more potent in killing CD30-expressing MCL and ALCL tumor cells compared to the variant with the lower-affinity CD3 arm that contains G at position 101.

In the cytotoxicity assays using HDLM-2 cells (left panel) or NCEB-1 cells (right panel) as target cells, the number of CFSE-positive cells were evaluated as a measure of absolute T-cell counts. FIG. 4D shows that T-cell mediated cytotoxicity of HDLM-2 and NCEB-1 cells induced by bsG1-huCD3-FEAL×CD30-MDX060-FEAR or bsG1-huCD3-H101G-FEAL×CD30-MDX060-FEAR (see FIG. 4B) was associated with a dose-dependent increase in T-cell count. Generally, similar T-cell numbers were counted after incubation with bsG1-huCD3-FEAL×CD30-MDX060-FEAR or bsG1-huCD3-H101G-FEAL×CD30-MDX060-FEAR in this assay. Reduced T-cell numbers were noted in co-cultures with NCEB-1 cells incubated with bsG1-huCD3-FEAL×CD30-MDX060-FEAR at concentrations higher than 1 µg/mL. Control antibody IgG1-b12-FEAL did not affect T-cell counts in these experiments.

In conclusion, BsG1-huCD3-FEAL×CD30-MDX060-FEAR induced T-cell proliferation in the presence of various CD30-expressing ALCL, HL and MCL tumor cell lines.

Example 5—Binding of CD3×CD30 Bispecific Antibodies to Human, Cynomolgus, or Rhesus Monkey CD30 Expressed in Expi293F Cells Binding of bispecific CD3×CD30 antibodies and monospecific, bivalent CD30 antibodies to the plasma membrane of Expi293 cells transiently transfected with human CD30 or cynomolgus monkey CD30 was analyzed by flow cytometry.

Transient Expression of Human, Cynomolgus or Rhesus Monkey CD30 in HEK-293F or HEK-293 Cells The following codon-optimized constructs for expression of various full-length CD30 variants were generated: human (*Homo sapiens*) CD30 (huCD30; Uniprot accession no. P28908), cynomolgus monkey (*Macaca fascicularis*) CD30 (mfCD30; Uniprot accession no. AOA2K5VW07) (SEQ ID NO:40) and rhesus monkey (*Macaca mulatta*) CD30 (mmCD30; Uniprot accession no. A0A1D5RK03) (SEQ ID NO:41). The constructs contained suitable restriction sites for cloning and an optimal Kozak (GCCGCCACC) sequence (Kozak, M., Gene 1999; 234(2):187-208). The full-length human CD30, cynomolgus and rhesus monkey CD30 codon-optimized constructs were cloned in the mammalian expression vector pcDNA3.3 (Invitrogen) and expressed using the Expi293F expression platform (Thermo Fisher Scientific, Waltham, MA, USA, cat. no. A14527) essentially as described by the manufacturer. In another set of experiments, the full-length human CD30 or cynomolgus monkey CD30 constructs were expressed in HEK-293 cells.

Binding of CD3×CD30 Bispecific Antibodies to Human, Cynomolgus Monkey or Rhesus Monkey CD30 Expressed in Expi293 Cells Cells ($3\times10^4$ cells/well) were incubated in polystyrene 96-well round-bottom plates (Greiner bio-one, cat. no. 650180) with serial dilutions of antibodies (ranging from 0.005 to 10 µg/mL in 3-fold dilution steps) in 100 µL staining buffer at 4° C. for 30 min. Experiments were performed in technical duplicate. After washing twice in staining buffer, cells were incubated in 50 µL secondary antibody at 4° C. for 30 min. As a secondary antibody, R-PE-conjugated goat-anti-human IgG (Jackson ImmunoResearch, UK; cat. no. 109-116-098) diluted 1:400 in staining buffer was used. Cells were washed twice in staining buffer, resuspended in 30 µL staining buffer containing 0.4% EDTA and analyzed on an iQue Screener (Intellicyt Corporation, USA). Binding curves were analyzed using non-linear regression (sigmoidal dose-response with variable slope) using GraphPad Prism V9.0.0 software (GraphPad Software, San Diego, CA, USA).

Binding of CD3×CD30 Bispecific Antibodies to Human, Cynomolgus Monkey or Rhesus Monkey CD30 Expressed in HEK293 Cells Cells ($3 \times 10^4$ cells/well) were incubated in polystyrene 96-well round-bottom plates (Thermo Scientific, cat. no. 163320) with serial dilutions of antibodies (ranging from 0.0002 to 50 µg/mL in 4-fold dilution steps) in 50 µL staining buffer at 4° C. for 30 min. Experiments were performed in technical duplicate. After washing twice in staining buffer, cells were incubated in 50 µL secondary antibody at 4° C. for 30 min. As a secondary antibody, R-PE-conjugated goat-anti-human IgG (Jackson ImmunoResearch, UK; cat. no. 109-116-098) diluted 1:200 in staining buffer was used. Cells were washed twice in staining buffer, resuspended in 30 µL staining buffer containing 0.4% EDTA and the ToPro-3 viability marker (Invitrogen, cat. no. T3605) diluted 1:10,000. Cells were analyzed on an iQue Screener (Intellicyt Corporation, USA). Binding curves were analyzed using non-linear regression (sigmoidal dose-response with variable slope) using GraphPad Prism V9.0.0 software (GraphPad Software, San Diego, CA, USA).

Binding of CD3×CD30 Bispecific Antibodies to Human T Cells or Cynomolgus Monkey PBMCs Cynomolgus monkey PBMCs (Tebu-Bio, The Netherlands; cat. no. PBMCMFA-10) or purified human T cells were plated in polystyrene 96-well round-bottom plates. T cells were derived from human donor buffy coats (Sanquin, Amsterdam, The Netherlands) and isolated using the RosetteSep human T cell enrichment cocktail (Stemcell Technologies, France, cat. no. 15061) according to manufacturer's instructions. Cells ($3 \times 10^4$ cells/well) were incubated with serial dilutions (ranging from 0.0001 to 10 µg/mL in 3-fold dilution steps) of antibodies IgG1-CD30-MDX060-FEAR, bsG1-huCD3-FEAL×CD30-MDX060-FEAR, and bsG1-huCD3-FEAL×b12-FEAR in 50 µL staining buffer at 4° C. for 30 min. After washing twice in staining buffer, cells were incubated in 50 µL secondary R-PE-conjugated goat-anti-human IgG antibody at 4° C. for 30 min (1:400 dilution). After washing twice in staining buffer, T cells were stained for T-cell markers CD3 (1:100; Miltenyi biotec, clone 10D12, conjugated to APC), CD4 (1:50; eBioscience, clone OKT4, conjugated to APC-Cy7), CD8 (1:100; Biolegend, clone RPA-T8, conjugated to AF700) and T-cell activation markers CD69 (1:50; BD Biosciences, clone AB2439, conjugated to FITC), CD25 (1:50; eBioscience, clone BC96, conjugated to PE-Cy7) and CD279/PD1 (1:50; BD Biosciences, clone AEH12.2H7, conjugated to BV605). Single stained samples with Ultracomp beads (5 µL; Invitrogen, cat. no. 01-2222-42) were used for compensation adjustments of the flow cytometer. After 30 min of incubation at 4° C., cells were washed twice with staining buffer, resuspended in 100 µL staining buffer and analyzed using a FACS Fortessa (BD Biosciences). Data were processed using FlowJo (BD Biosciences).

Results

Figure 5A:
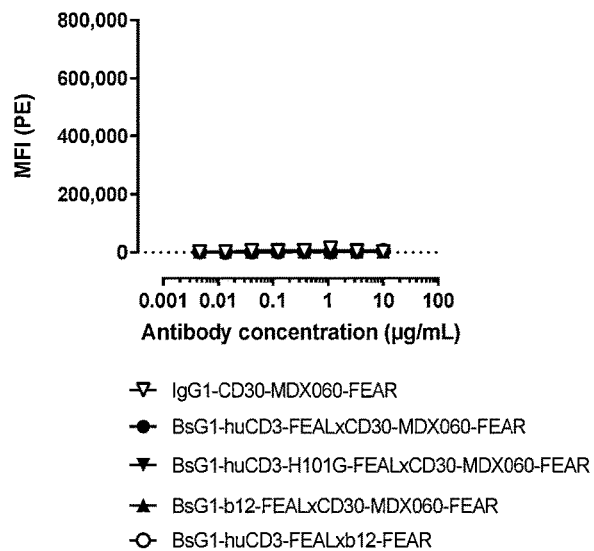
FIGS. 5A-5D: Binding of CD3×CD30 bispecific antibodies to full length human and cynomolgus monkey CD30 transfected into Expi293F cells.
Figure 5B:
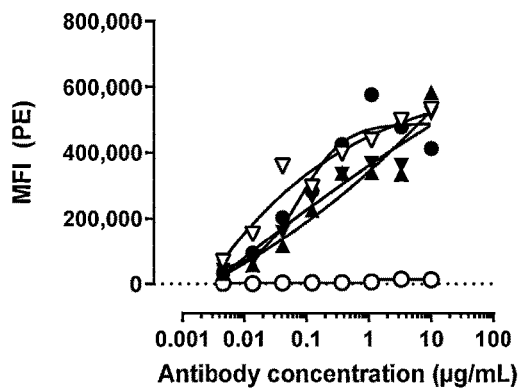
Figure 5C:
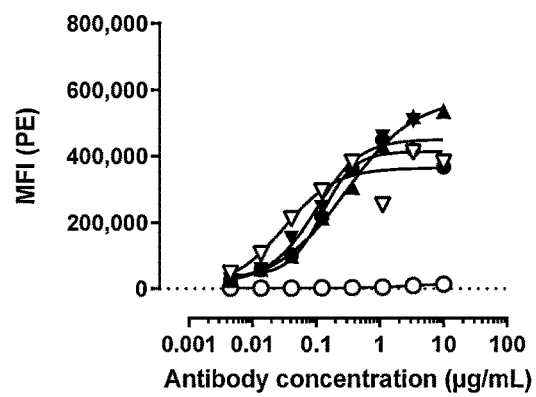

CD30-targeting bispecific antibodies bsG1-huCD3-FEAL×CD30-MDX060-FEAR, bsG1-huCD3-H101G-FEAL×CD30-MDX060-FEAR and bsG1-b12-FEAL×CD30-MDX060-FEAR showed no binding to wild-type Expi293F cells (FIG. 5A) but displayed dose-dependent binding to Expi293F cells transfected with huCD30 (FIG. 5B) or mfCD30 (FIG. 5C). Binding of these bispecific antibodies was comparable to binding of the monospecific, bivalent CD30 antibody IgG1-CD30-MDX060-FEAR. As expected, the negative control antibody bsG1-huCD3-FEAL×b12-FEAR showed no binding to wild type or huCD30- or mfCD30-transfected Expi293F cells. Similarly, bsG1-huCD3-FEAL×CD30-MDX060-FERR showed dose-dependent binding to HEK293 cells transfected with huCD30 (FIG. 11A) or mfCD30 (FIG. 11B), the negative control antibody bsG1-huCD3-FEAL×b12-FERR showed no binding to huCD30- or mfCD30-transfected HEK293 cells. This indicates that the CD30-targeting antibody MDX060 efficiently binds to both human and cynomolgus monkey CD30 expressed in HEK cells in a bivalent as well as a monovalent format.

Figure 5D:
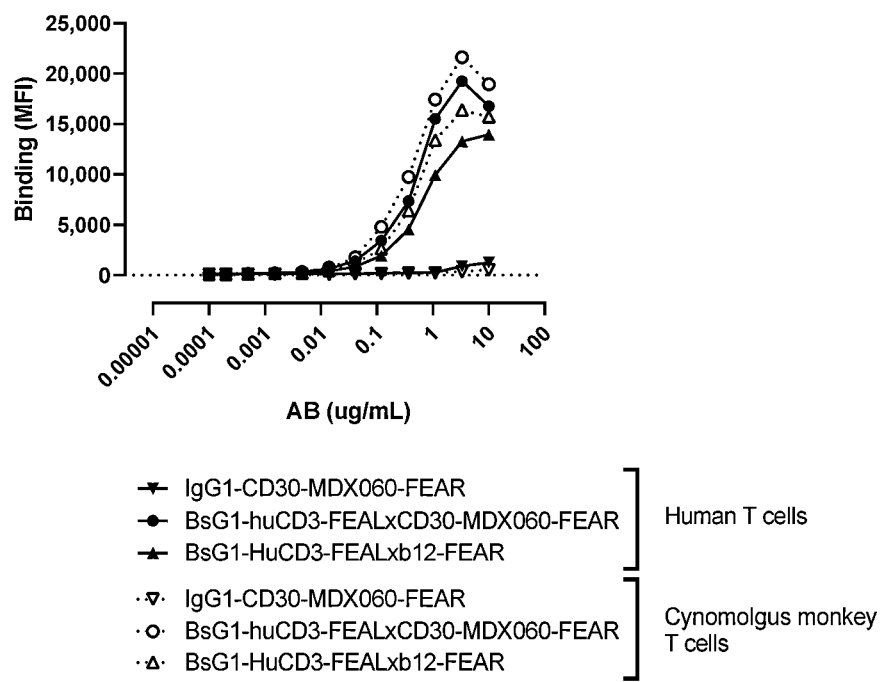

FIG. 5D shows that the CD3×CD30 bispecific antibody bsG1-huCD3-FEAL×CD30-MDX060-FEAR and control bispecific antibody bsG1-huCD3-FEAL×b12-FEAR efficiently bound to primary human and cynomolgus monkey T cells. This shows that these CD3-targeting bispecific antibodies efficiently bind to both human and cynomolgus monkey CD3 endogenously expressed on T cells. The IgG1-CD30-MDX060 bivalent, parental antibody did not bind to human or cynomolgus monkey T cells, indicating that CD30 was not expressed on these cells.

Figure 6D:
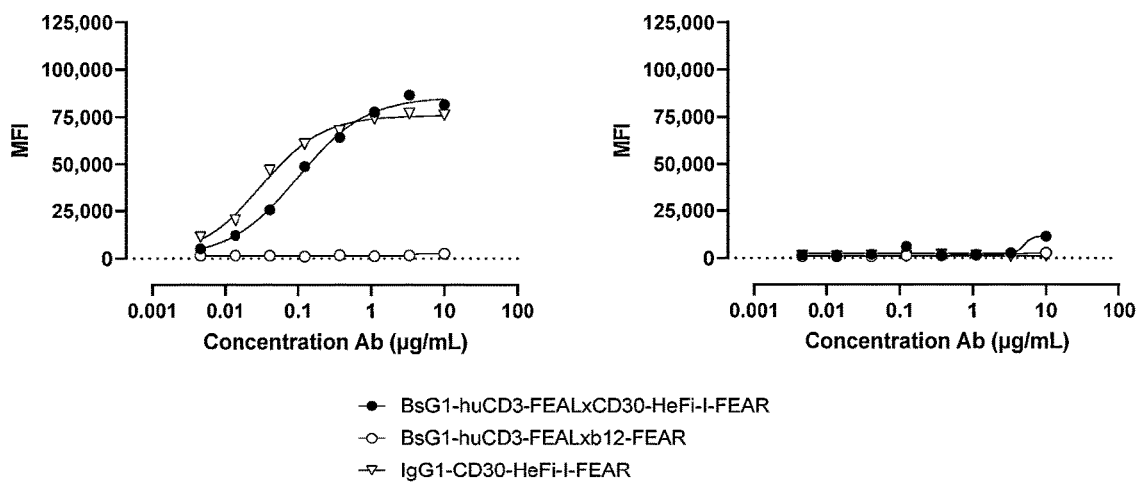

Binding of the panel of CD3×CD30 bispecific antibodies and the monospecific parental CD30 antibodies to Expi293F cells transfected with huCD30 or mmCD30 was evaluated by flow cytometry. The CD3×CD30 bispecific antibodies bsG1-huCD3-FEAL×CD30-MDX060-FEAR (FIG. 6A), bsG1-huCD3-FEAL×CD30-hAC10-FEAR (FIG. 6B), bsG1-huCD3-FEAL×CD30-HRS-3-FEAR (FIG. 6C), bsG1-huCD3-FEAL×CD30-T405-FEAR (FIG. 6E), bsG1-huCD3-FEAL×CD30-T105-FEAR (FIG. 6F), bsG1-huCD3-FEAL×CD30-T408-FEAR (FIG. 6G), and bsG1-huCD3-FEAL×CD30-T215-FEAR (FIG. 6H) showed equal binding to cells expressing huCD30 or mmCD30. Similarly, the parental, monospecific CD30 antibody clones showed equal binding to cells expressing huCD30 or mmCD30. In contrast, bsG1-huCD3-FEAL×CD30-HeFi-I-FEAR and the parental, monospecific CD30 antibody IgG1-CD30-HeFi-I_FEAR showed binding to huCD30, but not to mmCD30 (FIG. 6D).

Example 6—Assessment of Conformational Stability of Monospecific and Bispecific Non-Activating Antibody Variants by DSF Analysis Protein stability characteristics of bivalent monospecific CD30, CD3, and bispecific CD3×CD30 IgG1 antibody variants harboring non-activating mutations in the constant heavy chain region were assessed using differential scanning fluorimetry (DSF).

Samples of IgG1-CD30-MDX060-FEAR, IgG1-CD30-MDX060-FERR, IgG1-huCD3-FEAL and BsG1-huCD3-FEAL×CD30-MDX060-FERR were formulated in PBS pH 7.4 at a concentration of approximately 1 mg/mL.

To assess conformational stability, DSF was performed in an iQ5 Multicolor Real-Time PCR detection system (Bio-Rad) capable of detecting changes in fluorescence intensity caused by binding of the extrinsic dye Sypro-Orange (5000× concentrate in DMSO, Cat #S5692, Sigma-Aldrich) to hydrophobic regions exposed upon unfolding of IgG. Sypro-Orange was diluted 320-fold in PBS pH 7.4 (Hyclone GE Healthcare). A thermal melt curve can be derived from measuring the increasing fluorescence during controlled, stepwise thermal denaturation of the analyzed IgG. Therefore, duplicate samples of 5 μL of antibody solution (1 mg/mL in PBS;) were added to 20 μL of the diluted Sypro-Orange in PBS pH 7.4 in iQ 96-well PCR plates. Fluorescence was recorded at increasing temperatures ranging from 25° C. to 95° C., in stepwise increments of 0.5° C. per increment and 15 seconds duration plus the time required to record the fluorescence of all wells. The data was analyzed using Bio-Rad CFX Manager Software 3.0 and melting points were determined from the fluorescence versus temperature graphs by the software.

Results

FIG. 7 and Table 8 show that the melting temperature ($T_m$) of IgG1-CD30-MDX060-FERR is 69.0° C., which is higher than the $T_m$ of IgG1-CD30-MDX060-FEAR at pH 7.4 (64.5° C.). This indicates that IgG1-CD30-MDX060-FERR has higher conformational stability than IgG1-CD30-MDX060-FEAR suggesting that IgG1-CD30-MDX060 containing a FER backbone has a higher conformational stability than IgG1-CD30-MDX060 containing a FEA backbone. The melting temperature of BsG1-huCD3-FEALxCD30-MDX060-FERR was determined to be 64.5° C., which is between the $T_m$ determined for the two parental antibodies IgG1-huCD3-FEAL (62.5° C.) and IgG1-CD30-MDX060-FERR (69.0° C.).

TABLE 8

Melting temperatures ($T_m$) of indicated antibodies as determined by differential scanning fluorimetry (DSF)

| Antibody | $T_m$ (° C.) |
|---|---|
| IgG1-CD30-MDX060-FEAR | 64.5 |
| IgG1-CD30-MDX060-FERR | 69.0 |
| IgG1-huCD3-FEAL | 62.5 |
| BsG1-huCD3-FEALxCD30-MDX060-FERR | 64.5 |

Example 7—Simultaneous Binding of bsG1-huCD3-FEALxCD30-MDX060-FERR to T Cells and Tumor Cells Simultaneous binding of bsG1-huCD3-FEALxCD30-MDX060-FERR to tumor cells and naive T cells was studied.

Frozen T cells isolated from healthy donors were thawed and labelled with 0.25 mM Celltrace Violet (Pacific Blue; Invitrogen, cat no. C34557A) at 37° C. for 15 min. L-428 tumor cells were labelled with Celltrace FarRed (APC; Invitrogen cat no. C34564A) at 37° C. for 15 min and added to T cells at E:T ratio of 1:1. Serial dilutions of bsG1-huCD3-FEALxCD30-MDX060-FERR or control antibodies bsG1-huCD3-FEALxb12-FEAR, bsG1b12FEALxCD30MDX060-FERR, or IgG1-b12-FEAL were added (final concentration ranging from $6 \times 10^{-5}$ to 10 μg/mL; 3-fold dilutions) and cells were incubated for 2 hours at 4° C. After incubation, viability marker 7-AAD (BD Bioscience, cat. no 559925) was added (100×final dilution) and cells were analyzed on a FACS Celesta flow cytometer (BD Biosciences).

Results

FIG. 12 shows that bsG1-huCD3-FEALxCD30-MDX060-FERR induces the formation of $CD3^+CD30^+$ double-positive events (cells expressing both CellTrace Far Red and CellTrace Violet in flow cytometry staining) as a measure for bsG1-huCD3-FEALxCD30-MDX060-FERR-mediated crosslinking of tumor cells to T cells (simultaneous binding). The increase in double-positive events was antibody concentration-dependent and showed a bell-shaped curve. No increase in crosslinking of tumor cells and T cells was observed in samples incubated with control antibodies bsG1-huCD3-FEALxb12-FEAR, bsG1b12FEALxCD30MDX060-FERR, or IgG1-b12-FEAL or in samples incubated without antibody (A). FIG. 12 B shows simultaneous binding of bsG1-huCD3-FEALxCD30-MDX060-FERR to tumor cells and naive T cells, as detected by the percentage of cells expressing both CellTrace Far Red and CellTrace Violet (B).

These data indicate that bsG1huCD3FEALxCD30-MDX060-FERR can simultaneously bind and crosslink $CD30^+$ tumor cells and $CD3^+$ T cells.

Example 8—Induction of T-Cell Mediated Cytotoxicity and T-Cell Activation In Vitro by CD3×CD30 Bispecific Antibodies T-cell mediated cytotoxicity of Karpas-299 tumor cells and associated T-cell activation by a panel of CD3×CD30 bispecific antibodies was evaluated. The following antibodies were evaluated: bsG1-huCD3-FEALxCD30-MDX060-FERR, bsG1-huCD3-FEALxCD30-MDX060-FEAR, bsG1-huCD3-FEALxCD30-hAC10-FEAR, bsG1-huCD3-FEALxCD30-HRS-3-FEAR, bsG1-huCD3-FEALxCD30-HeFi-I-FEAR, bsG1-huCD3-FEALxCD30-T105-FEAR, bsG1-huCD3-FEALxCD30-T405-FEAR, bsG1-huCD3-FEALxCD30-T408-FEAR, and bsG1-huCD3-FEALxCD30-T215-FEAR.

T cells were obtained from healthy human donor buffy coats (Sanquin, Amsterdam, The Netherlands) and isolated using a RosetteSep™ human T-cell enrichment cocktail (Stemcell Technologies, France, cat. no. 15061) according to the manufacturer's instructions. T cells were labelled with Celltrace Violet (Invitrogen, cat. no. C34557A; final concentration 5 μM) for 15 min at 37° C. In parallel, Karpas-299 tumor cells were labeled with Celltrace FarRed (Invitrogen, cat. no. C34564A; final concentration 2 μM) for 15 min at 37° C. After labeling, 5×the volume of ice cold DBSI was added and incubated for 5 minutes at RT. Cells were pelleted, resuspended in medium, and tumor cells were seeded into 96-well plates (Greiner-bio-one, The Netherlands, cat. no. 655180) at a density of 50,000 cells/well. Serial dilutions of bispecific CD3×CD30 antibodies were added (final concentration ranging from 1,000 to 0.051 ng/mL; 3-fold dilutions) and plates were incubated for 15 min at RT. T cells were added to tumor cells at an effector to target (E:T) ratio of 4:1 and plates were incubated for 72 hours at 37° C. After washing 2 times with PBS/0.1% BSA/0.02% azide (staining buffer), cells were stained for T-cell markers CD4 (1:50; Biolegend, cat. no. 300521, conjugated to Pacific Blue), CD8 (1:100; BD Biosciences, conjugated to FITC) and T cell activation markers CD69 (1:50; Biolegend, cat. no. 310934, conjugated to BV650), CD25 (1:100; Invitrogen, cat. no. 25-0259-42, conjugated to PE-Cy7) and CD279/PD-1 (1:50; Biolegend, cat. no. 329930, conjugated to BV605). Single stained samples with Ultracomp beads (5 μL; Invitrogen, cat. no. 01-2222-42) were included and used for compensation adjustments of the flow cytometer. After 30 min of incubation at 4° C., plates were washed twice with staining buffer, and cells were stained with 7-AAD (diluted 1:100 in staining buffer) for 10 min at 4° C. Cells were analyzed using a FACS Celesta (BD Biosciences). Data were processed using FlowJo (BD Biosciences).

Dose-response curves were generated using non-linear regression analysis (sigmoidal dose-response with variable slope) using GraphPad Prism V7.02 software (GraphPad Software, San Diego, CA, USA).

Results

Figure 13A:
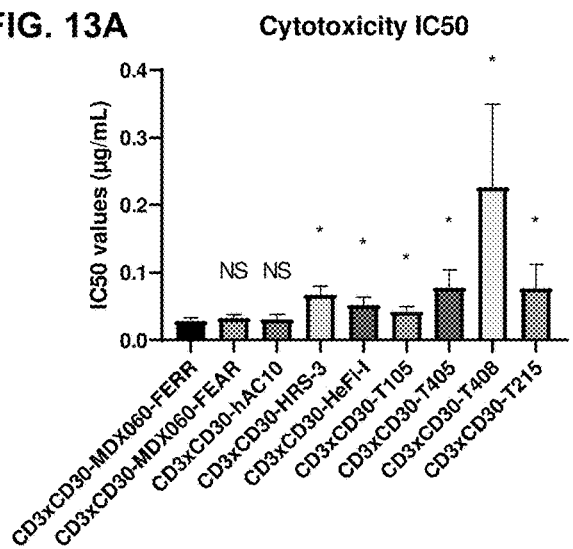
Figure 13B:
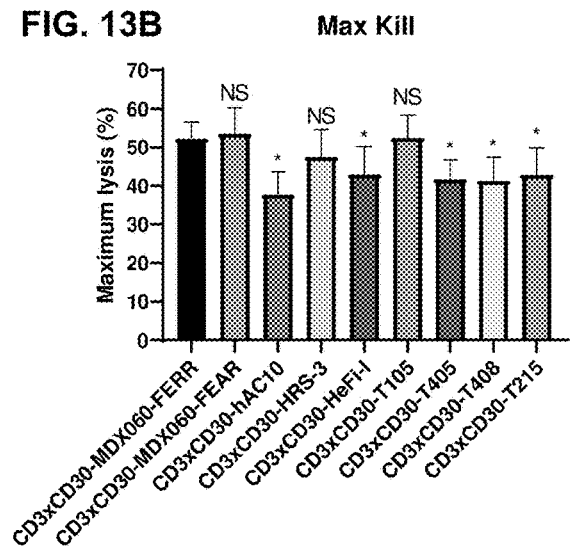
Figure 13C:
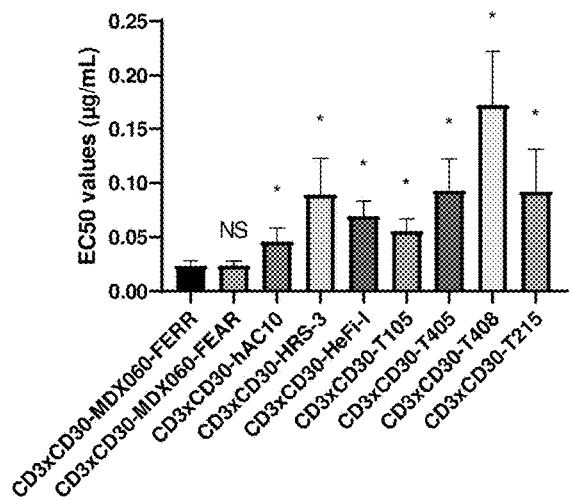
Figure 13D:
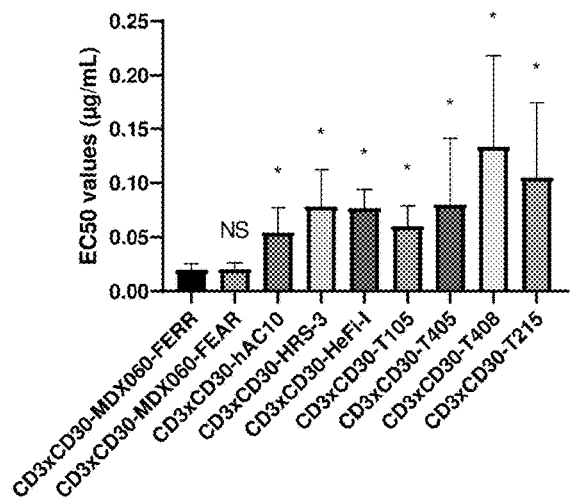
Figure 16A:
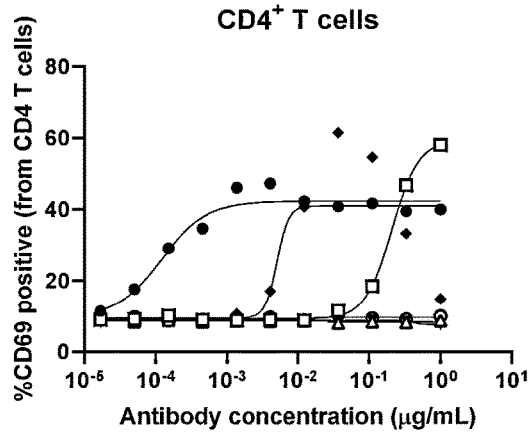
Figure 16B:
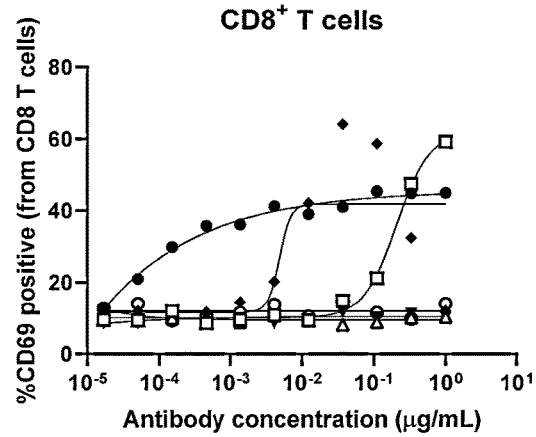
Figure 16C:
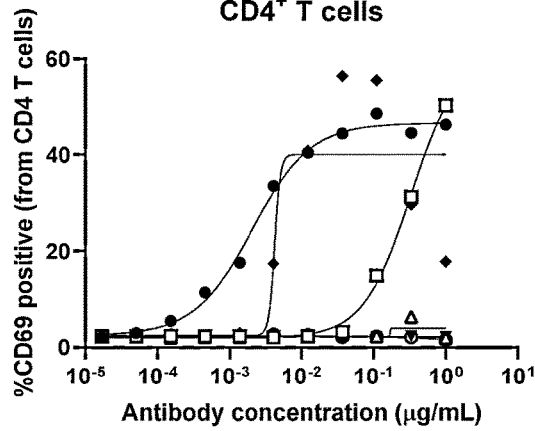
Figure 16D:
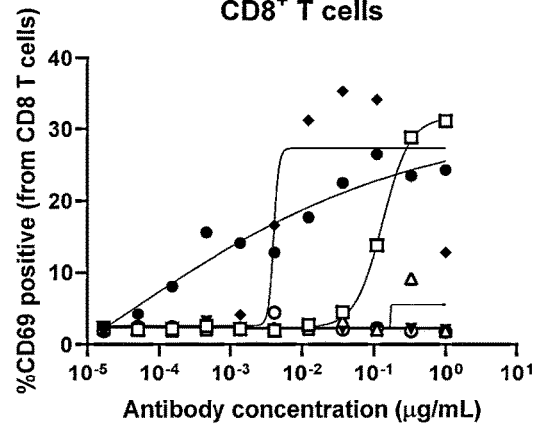
Figure 17A:
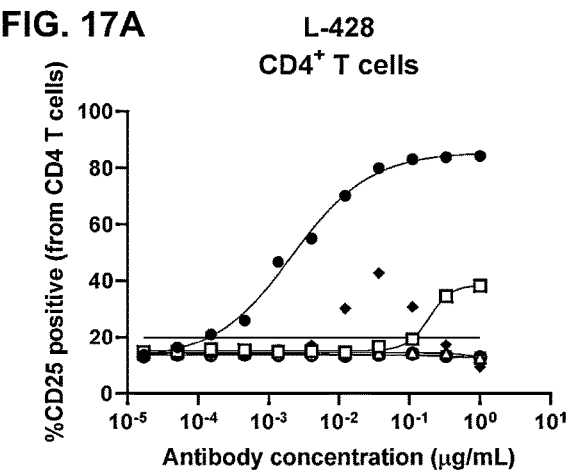
Figure 17B:
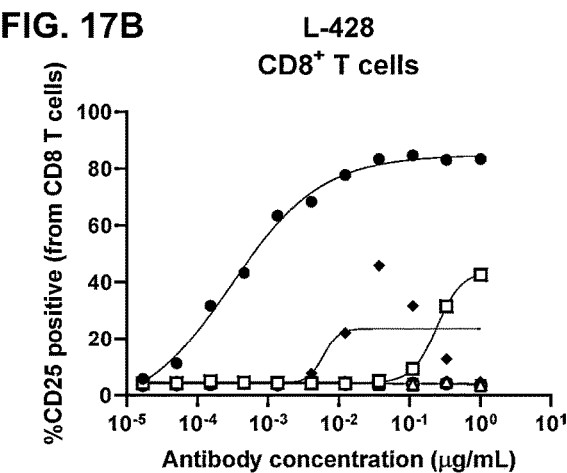
Figure 17C:
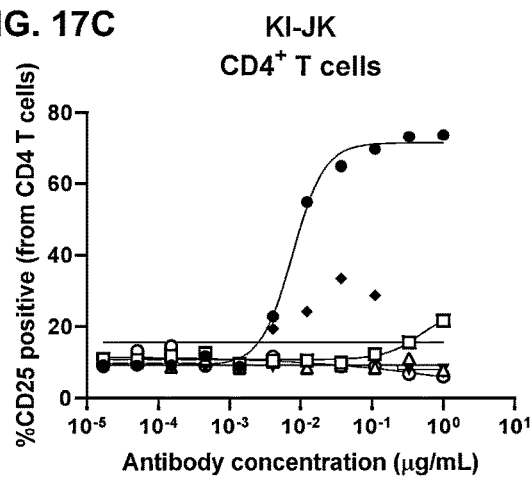
Figure 17D:
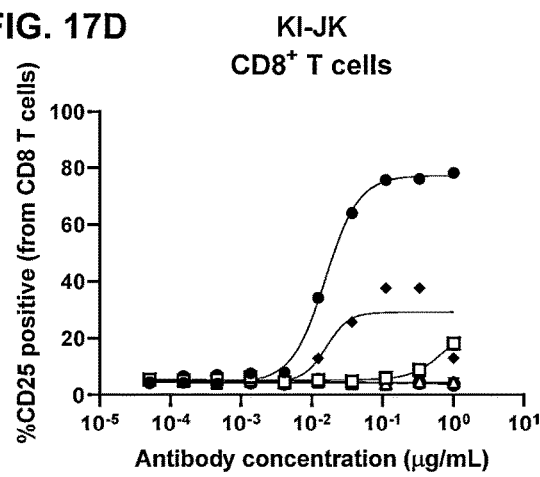
Figure 18A:
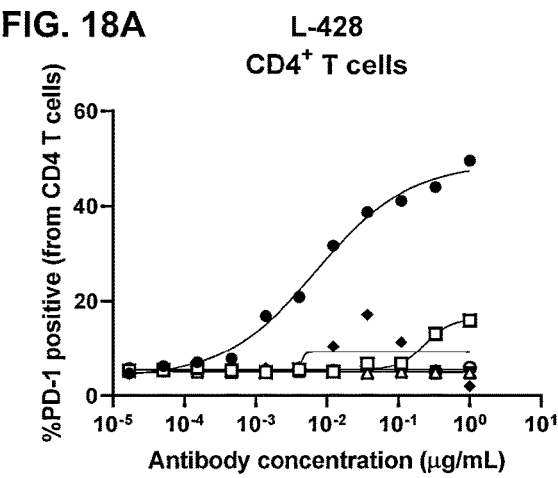
Figure 18B:
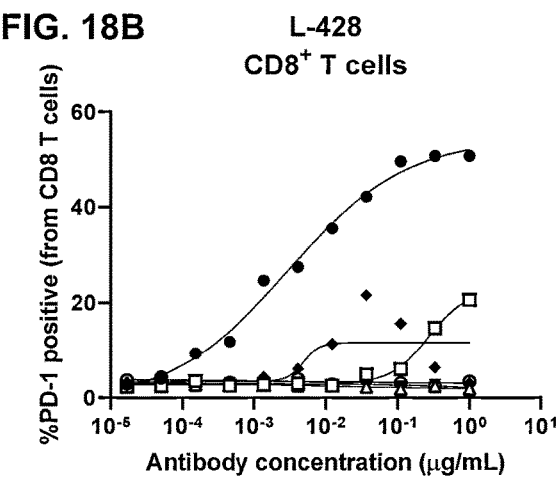
Figure 18C:
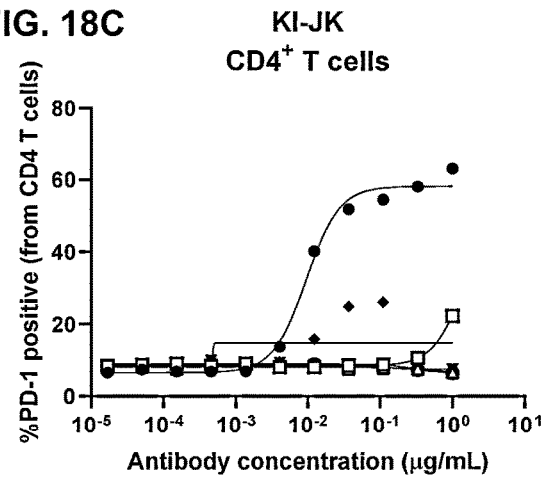
Figure 18D:
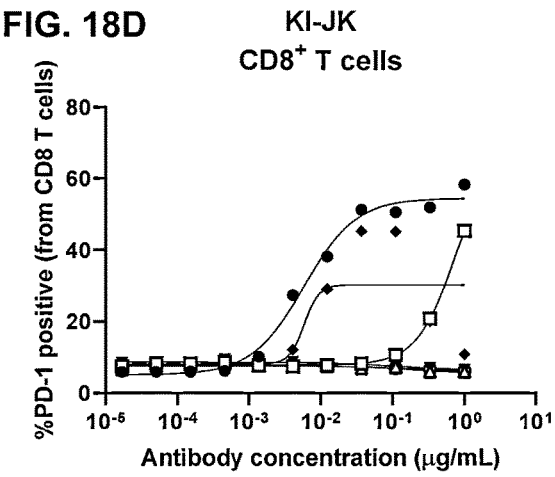

FIGS. 13A and B show that all CD3×CD30 antibodies induce T-cell mediated cytotoxicity of Karpas-299 cells. CD3×CD30 bispecific antibodies generated using CD30 clone MDX060 (bsG1-huCD3-FEAL×CD30-MDX060-FERR and bsG1-huCD3-FEAL×CD30-MDX060-FEAR) were more effective in killing Karpas-299 cells compared to all other clones tested. In fact, MDX060-based CD3×CD30 bispecific antibodies showed significantly lower $IC_{50}$ values compared to CD3×CD30 bispecific antibodies generated using CD30 clones HRS-3, HeFi-I, T105, T405, T408, or T215 (bsG1-huCD3-FEAL×CD30-HRS-3-FEAR, bsG1-huCD3-FEAL×CD30-HeFi-I-FEAR, bsG1-huCD3-FEAL×CD30-T105-FEAR, bsG1-huCD3-FEAL×CD30-T405-FEAR, bsG1-huCD3-FEAL×CD30-T408-FEAR, and bsG1-huCD3-FEAL×CD30-T215-FEAR; FIG. 13A). Furthermore, bsG1-huCD3-FEAL×CD30-MDX060-FERR and bsG1-huCD3-FEAL×CD30-MDX060-FEAR induced higher maximum killing compared to CD3×CD30 bispecific antibodies generated using CD30 clones hAC10, HeFi-I, T405, T408, or T215 (bsG1-huCD3-FEAL×CD30-hAC10-FEAR, bsG1-huCD3-FEAL×CD30-HeFi-I-FEAR, bsG1-huCD3-FEAL×CD30-T405-FEAR, bsG1-huCD3-FEAL×CD30-T408-FEAR, and bsG1-huCD3-FEAL×CD30-T215-FEAR; FIG. 13B). FIGS. 13C and D show that bsG1-huCD3-FEAL×CD30-MDX060-FERR and bsG1-huCD3-FEAL×CD30-MDX060-FEAR were more effective (lower $EC_{50}$ values) than any of the other CD3×CD30 bispecific antibodies at inducing expression of CD25, as a measure of T-cell activation in CD4$^+$ T cells (FIG. 13C) or CD8$^+$ T cells (FIG. 13D). Similar results were observed for expression of PD-1 (FIGS. 13E and F) and CD69 (data not shown). No difference in T-cell-mediated killing or T-cell activation was observed between the two MDX060-based CD3×CD30 bispecific antibodies that contain the FEAR or FERR mutations.

The bispecific antibody bsG1-huCD3×CD30-MX060 was also more effective at inducing T-cell mediated cytotoxicity of L-428 cells in comparison to other panel CD3×CD3 bispecific antibodies tested (data not shown).

The average $IC_{50}$ concentrations and maximum percentage lysis of T-cell mediated cytotoxicity and $EC_{50}$ concentrations of T-cell activation (CD25 expression) induced by the panel of CD3×CD30 bispecific antibodies used in these experiments are summarized in Table 9.

In conclusion, these data demonstrated that bsG1huCD3×CD30-MDX060 was more effective than any of the other CD3×CD30 bispecific antibodies evaluated at inducing T-cell mediated cytotoxicity.

TABLE 9

$IC_{50}$ concentrations and maximum percentage lysis of T-cell mediated cytotoxicity of Karpas-299 cells and $EC_{50}$ concentrations of T-cell activation (CD25 expression) induced by a panel of CD3×CD30 bispecific antibodies.

| Antibody | cytotoxicity | | T-cell activation (CD25 expression) | | T-cell activation (PD-1 expression) | |
|---|---|---|---|---|---|---|
| | $IC_{50}$ (μg/mL) average (SD) | maximum lysis (%) average (SD) | CD4+ T cells $EC_{50}$ (μg/mL) average (SD) | CD8+ T cells $EC_{50}$ (μg/mL) average (SD) | CD4+ T cells $EC_{50}$ (μg/mL) average (SD) | CD8+ T cells $EC_{50}$ (μg/mL) average (SD) |
| bsG1-huCD3-FEALxCD30-MDX060-FERR | 0.029 (0.004) | 52.328 (3.929) | 0.023 (0.004) | 0.020 (0.005) | 0.025 (0.006) | 0.023 (0.009) |
| bsG1-huCD3-FEALxCD30-MDX060-FEAR | 0.033 (0.004) | 53.703 (5.949) | 0.024 (0.004) | 0.020 (0.005) | 0.024 (0.006) | 0.027 (0.009) |
| bsG1-huCD3-FEALxCD30-hAC10-FEAR | 0.032 (0.006) | 37.765 (5.340) | 0.046 (0.011) | 0.054 (0.021) | 0.056 (0.021) | 0.057 (0.031) |
| bsG1-huCD3-FEALxCD30-HRS-3-FEAR | 0.068 (0.011) | 47.472 (6.539) | 0.089 (0.031) | 0.079 (0.031) | 0.123 (0.046) | 0.112 (0.047) |
| bsG1-huCD3-FEALxCD30-HeFi-I-FEAR | 0.052 (0.011) | 42.987 (6.603) | 0.069 (0.013) | 0.076 (0.016) | 0.075 (0.024) | 0.083 (0.023) |
| bsG1-huCD3-FEALxCD30-T105-FEAR | 0.042 (0.007) | 52.582 (5.344) | 0.056 (0.010) | 0.060 (0.017) | 0.064 (0.021) | 0.065 (0.024) |
| bsG1-huCD3-FEALxCD30-T405-FEAR | 0.078 (0.023) | 41.667 (4.560) | 0.093 (0.027) | 0.080 (0.056) | 0.138 (0.054) | 0.140 (0.126) |
| bsG1-huCD3-FEALxCD30-T408-FEAR | 0.226 (0.112) | 41.295 (5.482) | 0.172 (0.046) | 0.134 (0.077) | 0.286 (0.104) | 0.220 (0.126) |
| bsG1-huCD3-FEALxCD30-T215-FEAR | 0.077 (0.032) | 42.840 (6.464) | 0.092 (0.036) | 0.105 (0.063) | 0.355 (0.476) | 0.281 (0.308) |

Example 9—Induction of T-Cell Mediated Cytotoxicity, T-Cell Proliferation, and T-Cell Activation In Vitro by bsG1-huCD3-FEAL×CD30-MDX060-FERR T-cell mediated cytotoxicity of tumor cells and associated T-cell proliferation and activation by bsG1-huCD3-FEAL×CD30-MDX060-FERR was evaluated in HL and ALCL cell lines.

T cells were obtained from healthy human donor buffy coats (Sanquin, Amsterdam, The Netherlands) and isolated using a RosetteSep™ human T-cell enrichment cocktail (Stemcell Technologies, France, cat. no. 15061) according to the manufacturer's instructions. T cells were labelled with Celltrace Violet (Invitrogen, cat. no. C34557A; final concentration 5 μM) for 15 min at 37° C. In parallel, tumor cells L-428, KI-JK, KM-H2, or SUP-M2 were labelled with Celltrace FarRed (Invitrogen, cat. no. C34564A; final concentration 2 μM) for 15 min at 37° C. After labeling, 5×the volume of ice cold DBSI was added and incubated for 5 minutes at RT. Cells were pelleted, resuspended in medium, and tumor cells were seeded into 96-well plates (Greiner-bio-one, The Netherlands, cat. no. 655180) at a density of 50,000 cells/well. Serial dilutions of bsG1-huCD3-FEAL×CD30-MDX060-FERR or control antibodies IgG1-huCD3-FEAL, bsG1-huCD3-FEAL×b12-FERR, IgG1-CD30-MDX060-FERR, bsG1-b12-FEAL×CD30-MDX060-FERR, IgG1-b12-FEAL were added (final concentration ranging from 1,000 to 0.051 ng/mL; 3-fold dilutions) and plates were incubated for 15 min at RT. T cells were added to tumor cells at an effector to target (E:T) ratio of 4:1 and plates were incubated for 72 hours at 37° C. After washing 2 times with PBS/0.1% BSA/0.02% azide (staining buffer), cells were stained for T-cell markers CD4 (1:50; Biolegend, cat. no. 300521, conjugated to Pacific Blue), CD8 (1:100; BD Biosciences, cat. no. 345772, conjugated to FITC) and T cell activation markers CD69 (1:50; Biolegend, cat. no. 310934, conjugated to BV650), CD25 (1:100; Invitrogen, cat. no. 25-0259-42, conjugated to PE-Cy7) and CD279/PD-1 (1:50; Biolegend, cat. no. 329930, conjugated to BV605). Single stained samples with Ultracomp beads (5 μL; Invitrogen, cat. no. 01-2222-42) were included and used for compensation adjustments of the flow cytometer. After 30 min of incubation at 4° C., plates were washed twice with staining buffer and cells were stained with 7-AAD (diluted 1:100 in staining buffer) for 10 min at 4° C. Cells were analyzed using a FACS Celesta (BD Biosciences) and data were processed using FlowJo (BD Biosciences).

The percentage of live target cells was calculated using the following equation:

% live target cells=(absolute number of live,single Celltrace FarRed-labeled cells in each condition/absolute number of live,single Celltrace FarRed labeled cells in the condition containing only target cells and T cells without adding any antibodies)×100.

T-cell proliferation was evaluated by gating CD4$^+$ or CD8$^+$ T cells with diluted Celltrace Violet staining. The expansion index was calculated using the proliferation modeling tool from FlowJo.

Generation peaks were automatically fitted and expansion index values were calculated according the following equation:

Expansion index=Total amount of cells/amount of cells at start of culture=($G0+G1+G2+G3+G4+G5+G6$)/($G0+G1$:$2+G2$:$4+G3$:$8+G4$:$16+G5$:$32+G6$:$64$).

Gn=number of cells in generation n peak (with n=0 to 6).

Dose-response curves were generated using non-linear regression analysis (sigmoidal dose-response with variable slope) using GraphPad Prism V7.02 software (GraphPad Software, San Diego, CA, USA).

Results

FIG. 14 shows that bsG1-huCD3-FEAL×CD30-MDX060-FERR induced dose-dependent T-cell mediated cytotoxicity in L-428 (HL), KM-H2 (HL), SUP-M2 (ALCL), and KI-JK (ALCL) cell lines in vitro. The average IC50 concentrations of T-cell mediated cytotoxicity induced by bsG1-huCD3-FEAL×CD30-MDX060-FERR in L-428 and KI-JK cells are summarized in Table 10. No cytotoxicity was observed in cells incubated with control antibodies IgG1-huCD3-FEAL, bsG1-huCD3-FEAL×b12-FERR, IgG1-CD30-MDX060-FERR, bsG1-b12-FEAL×CD30-MDX060-FERR, IgG1-b12-FEAL or in samples incubated without antibody.

FIGS. 15, 16, 17, and 18 show that T-cell mediated cytotoxicity of L-428 and KI-JK cells induced by bsG1-huCD3-FEAL×CD30-MDX060-FERR was associated with CD4$^+$ and CD8$^+$ T cell proliferation (FIG. 15) and expression of T-cell activation markers CD69 (FIG. 16), CD25 (FIG. 17) and PD-1 (FIG. 18). The average EC50 concentrations of T-cell proliferation and activation induced by bsG1-huCD3-FEAL×CD30-MDX060-FERR in these experiments are summarized in Table 10.

Hence, bsG-huCD3-FEAL×CD3-MDX060-FERR induced dose-dependent T-cell mediated cytotoxicity in HL and ALCL cell lines in vitro, which was associated with T-cell proliferation and activation.

TABLE 10

EC$_{50}$ concentrations of T-cell mediated cytotoxicity induced by bsG1-huCD3-FEAL×CD30-MDX060-FERR in L-428 and KI-JK cells and associated T-cell proliferation and activation of CD4$^+$ and CD8$^+$ cells.

| | Tumor Cell line | L-428 | | KI-JK | |
|---|---|---|---|---|---|
| | | Cytotoxicity | | | |
| | Average IC50 (μg/mL) | 0.002 | | 0.0015 | |
| | Range IC50 (μg/mL) | 0.001216-0.003439 | | 0.0008858-0.001904 | |
| | T cell type | CD4$^+$ | CD8$^+$ | CD4$^+$ | CD8$^+$ |
| | | T cell proliferation | | | |
| PI | Average EC50 (μg/mL) | 0.0051 | 0.00096 | 0.00606 | 0.00213 |
| | Range EC50 (μg/mL) | 0.003727-0.006534 | 0.0002052-0.002255 | 0.00338-0.007501 | 0.001103-0.002715 |
| | | T cell activation | | | |
| CD69 | Average CD69 EC50 (μg/mL) | 0.00083 | 0.00121 | 0.00146 | 0.00171 |
| | Range CD69 EC50 (μg/mL) | 0.0001221-0.001647 | 3.252E-14-0.002421 | 0.0004487-0.002086 | 4.694E-11-0.005097 |
| CD25 | Average CD25 EC50 (μg/mL) | 0.00261 | 0.00061 | 0.00599 | 0.00656 |
| | Range CD25 EC50 (μg/mL) | 0.002164-0.002898 | 0.000298-0.001006 | 0.004483-0.007791 | 0.001901-0.01562 |

TABLE 10-continued

EC$_{50}$ concentrations of T-cell mediated cytotoxicity induced by bsG1-huCD3-FEALxCD30-MDX060-FERR in L-428 and KI-JK cells and associated T-cell proliferation and activation of CD4$^+$ and CD8$^+$ cells.

| Tumor Cell line | | L-428 | | KI-JK | |
|---|---|---|---|---|---|
| PD-1 | Average PD-1 EC50 (µg/mL) | 0.00491 | 0.00257 | 0.0112 | 0.00696 |
| | Range PD-1 EC50 (µg/mL) | 0.004387-0.005433 | 0.001302-0.003412 | 0.009616-0.01222 | 0.005845-0.009151 |
| | n test | 3 | | 3 | |

Example 10—Induction of Cytokine Production In Vitro by bsG1-huCD3-FEALxCD30-MDX060-FERR Cytokine and Granzyme B production induced by bsG1-huCD3-FEALxCD30-MDX060-FERR was evaluated in supernatants that were collected during an in vitro T cell-mediated cytotoxicity experiment using L-428 target cells and healthy donor T cells, as described in example 9. Supernatants were stored at −20° C. and thawed for analysis. The concentration of 14 different cytokines (CD40, IFNγ, IL-10, IL-12, IL-13, IL-1b, IL-2, IL-4, IL-6, IL-8, IP-10, MCP-1, PDL-1, TNFα) and Granzyme B were measured using a bead-based multiplex immuno-assay (luminex) custom made by R&D systems.

Results

Increased concentrations were primarily observed for Granzyme B and cytokines IFNγ, IL-13 and TNFα (>2000 µg/mL) in supernatants from co-cultures of L-428 cells and T cells in the presence of bsG1-huCD3-FEALxCD30-MDX060-FERR. A moderate increase was observed for CD40, IL-10, IL-12, IL-1p, IL-2, IL-4, IL6, and IP-10 cytokine concentrations, when compared to the control antibody IgG1-b12-FEAL. Levels of IL-8, MCP-1, and PDL1 were not modulated compared to the control antibody IgG1-b12-FEAL (FIG. 19).

Thus, T-cell mediated cytotoxicity and T-cell activation by bsG1-huCD3-FEALxCD30-MDX060-FERR was associated with dose-dependent production of cytokines and Granzyme B.

Example 11—Induction of T-Cell Mediated Cytotoxicity In Vitro by bsG1-huCD3-FEALxCD30-MDX060-FERR Using Purified T Cells as Effector Cells at Varying Effector to Target Ratios To determine the optimal effector to target cell ratio of T cell-mediated tumor cell kill in the presence of bispecific antibody bsG1-huCD3-FEALxCD30-MDX060-FERR, an in vitro cytotoxicity assay was performed using the CD30-positive tumor cell line L-428 as target cells and purified T cells as effector cells at varying effector to target cell (E:T) ratios.

T-cell mediated cytotoxicity was evaluated essentially as described in Example 9, except that T cells were added to tumor cells at varying effector to target (E:T) cell ratios of 1:1, 2:1, 4:1 or 8:1.

Results

FIG. 20A shows that dose-dependent T-cell mediated cytotoxicity was induced by bsG1-huCD3-FEALxCD30-MDX060-FERR at all E:T ratios, with maximum tumor cell kill (less than 20% viable tumor cells) observed at E:T ratios of 4:1 and 8:1. In line with this, CD4$^+$ and CD8$^+$ T cell proliferation was observed at all E:T cell ratios, most prominently at E:T ratios of 4:1 and 8:1 (FIG. 20B-C). No specific T-cell mediated cytotoxicity or T-cell proliferation was induced by control antibody bsG1-huCD3-FEALxb12-FERR at any of the E:T ratios tested.

Together, these data indicate that bsG1-huCD3-FEALxCD30-MDX060-FERR-induced T-cell mediated cytotoxicity of L-428 tumor cells in vitro was most effective at E:T ratios of 4:1 and 8:1.

Example 12—Kinetics of T-Cell Mediated Cytotoxicity and T-Cell Proliferation In Vitro by bsG1-huCD3-FEALxCD30-MDX060-FERR To evaluate the kinetics of T cell-mediated tumor cell kill in the presence of bsG1-huCD3-FEALxCD30-MDX060-FERR, an in vitro cytotoxicity assay was performed at varying incubation periods using the CD30-positive tumor cell line L-428 as target cells and purified T cells as effector cells.

T-cell mediated cytotoxicity was evaluated essentially as described in Example 9, except that tumor cell cytotoxicity and T-cell proliferation was evaluated after 24 h, 48 h and 72 h.

Results

FIG. 21 shows that bsG1-huCD3-FEALxCD30-MDX060-FERR induced dose-dependent T-cell mediated cytotoxicity after 48 h and 72 h, while no significant T-cell mediated cytotoxicity was observed after 24 h. Dose-dependent CD4$^+$ and CD8$^+$ T cell proliferation was induced by bsG1-huCD3-FEALxCD30-MDX060-FERR after 72 h, while no T-cell proliferation was observed after 24 h or 48 h (FIGS. 21B and C).

Together, these data show that bsG1-huCD3-FEALxCD30-MDX060-FERR induced T-cell mediated cytotoxicity of tumor cells and T-cell proliferation in a time-dependent manner.

Example 13—Correlation of CD30 Expression Level with bsG1-huCD3-FEALxCD30-MDX060-FERR-Induced T-Cell Mediated Cytotoxicity In Vitro T-cell mediated kill by bsG1-huCD3-FEALxCD30-MDX060-FERR of eight CD30 expressing tumor cell lines was determined in an in vitro cytotoxicity assay as described in example 9, using an E:T ratio of 4:1. The following cell lines were used: L-428, KM-H2, DEL, KI-JK, KARPAS-299, SUP-M2, NCEB-1, and JVM-2. For these tumor cell lines, CD30 expression levels were evaluated by quantitative flow cytometry as detailed in example 2.

Results

FIG. 22 shows that bsG1-huCD3-FEALxCD30-MDX060-FERR induced T-cell mediated cytotoxicity in all cell lines in vitro with maximum target cell kill between 68% and 98%. Maximum T-cell mediated tumor cell kill by bsG1-huCD3-FEALxCD30-MDX060-FERR significantly correlated with the level of CD30 expression (FIG. 22A).

In FIG. 22B the $EC_{50}$ of T cell-mediated kill in the presence of bsG1-huCD3-FEALxCD30-MDX060-FERR for each cell line is plotted against CD30 expression levels, showing a negative, but nonsignificant, trend.

Thus, these data show a positive correlation between CD30 expression levels and bsG1-huCD3-FEALxCD30-MDX060-FERR-induced maximum T-cell mediated cytotoxicity in vitro.

Example 14—Fratricide of Activated T Cells by BsG1-huCD3-FEALxCD30-MDX060-FERR

BsG1-huCD3-FEALxCD30-MDX060-FERR-induced T-cell fratricide of activated-$CD30^+$ T-cells was evaluated in vitro.

A 96-well plate (Greiner-bio-one, The Netherlands, cat. no. 655180) was coated with 100 μL of a solution of 1 μg/mL anti-human CD3 (clone OKT3, Invitrogen, cat. no. 16-0037-85) in PBS. The plate was incubated for 4 hours at 37° C. After removing the antibody solution, wells were washed with 100 μL of PBS. T cells were obtained from healthy human donor buffy coats (Sanquin, Amsterdam, The Netherlands) and isolated using aRosetteSep™ human T cell enrichment cocktail (Stemcell Technologies, France, cat. no. 15061) according to the manufacturer's instructions. Purified T cells were resuspended in T-cell medium (Roswell Park Memorial Institute [RPMI]-1640 medium with 25 mM HEPES and L-glutamine (Lonza, cat. no. BE12-115F), supplemented with 10% heat-inactivated donor bovine serum with iron (DBSI; Gibco, cat. no. 20731-030) and penicillin/streptomycin (pen/strep; Lonza, cat. no. DE17-603E) at a concentration of $2 \times 10^6$ cells/mL 100 μL of T-cell suspension (containing 200,000 T-cells) was added to each well of the anti-CD3 coated plate. Furthermore, 100 μL of T cell culture medium supplemented with 2 μg/mL anti-CD28 (clone CD28.2, Invitrogen, cat. no. 16-0289-85) and 0.05 μg/mL IL-15 (ThermoFisher, cat. no. PHC9151) was added to each well. T-cells were then incubated for 96 hours at 37° C.

After 96 hours, T cells were collected and resuspended in T-cell medium at a concentration of $2 \times 10^6$ cells/mL. Flow cytometry analysis was performed to measure the expression of CD30 and T-cell activation markers. In brief, an aliquot of cells was washed with PBS/0.1% BSA/0.02% azide (staining buffer), stained with 50 μl of 1000× diluted FVS510 viability dye (BD Biosciences, cat. no. 564406) and incubated at room temperature for 15 minutes. Then the cells were washed with staining buffer, and stained for CD30 (1:50; Biolegend, cat. no. 333906, conjugated to PE), T-cell markers CD4 (1:50; Biolegend, cat. no. 300506, conjugated to FITC), CD8 (1:100; Biolegend, cat. no. 301028, conjugated to AF700) and T-cell activation markers CD69 (1:50; Biolegend, cat. no. 310910, conjugated to APC), CD25 (1:100; Invitrogen, cat. no. 25-0259-42, conjugated to PE-Cy7) and CD279/PD1 (1:50; Biolegend, cat. no. 329924, conjugated to BV605). Single stained samples with Ultracomp beads (5 μL; Invitrogen, cat. no. 01-2222-42) were included and used for compensation adjustments of the flow cytometer. After 30 min of incubation at 4° C., plates were washed twice with staining buffer. Cells were analyzed using a FACS Celesta (BD Biosciences) and data were processed using FlowJo (BD Biosciences).

To assess whether the BsG1-huCD3-FEALxCD30-MDX060-FERR can induce fratricide of activated T cells, stimulated T cells were seeded in a 96-well plate at a density of 200,000 cells/well. Subsequently, 50 μL of BsG1-huCD3-FEALxCD30-MDX060-FERR, or control antibodies, i.e. bsG1-b12-FEALxCD30-MDX060-FERR, bsG1-huCD3-FEALxb12-MDX060-FERR, or IgG1-b12 were added to each well (final concentration ranging from 0.003 to 3.3 μg/mL in 3-fold dilution steps in T-cell medium). Plates were incubated at 37° C. for 48 hours.

After washing 2 times with staining buffer, cells were stained with FVS510 viability dye and consequently stained for T-cell markers CD4 and CD8 and T cell activation markers CD69, CD25 and CD279/PD1. Flow cytometric analysis was performed using a FACS Celesta (BD Biosciences) and data were processed using FlowJo (BD Biosciences).

Dose-response curves were generated using GraphPad Prism V7.02 software (GraphPad Software, San Diego, CA, USA).

Results

FIG. 23 shows that cell markers CD25 (T-cell activation) (A) and CD30 (B) were expressed in 54-63% and 21-27% of T cells respectively after 72 hours of incubation. Expression of CD25 and CD30 was further induced after 96 hours of incubation (CD25: 80-83% and CD30: 27-33%). FIG. 23C shows that increasing doses of BsG1-huCD3-FEALxCD30-MDX060-FERR, bsG1-b12-FEALxCD30-MDX060-FERR, bsG1-huCD3-FEALxb12-MDX060-FERR, or IgG1-b12 were not associated with reduced viability of activated T cells.

Therefore, CD30 expression on a subpopulation of activated T cells did not result in fratricide of T cells upon incubation with BsG1-huCD3-FEALxCD30-MDX060-FERR.

Example 15—Interference of sCD30 with the Anti-Tumor Activity of BsG1-huCD3-FEALxCD30-MDX060-FERR Shedding of cell surface CD30 and generation of soluble CD30 (sCD30) were evaluated in 17 different hematological $CD30^+$ tumor cell lines.

The concentration of sCD30 in 25 μL of undiluted supernatant collected from cell cultures three days after seeding cells in the fresh medium was measured by an ELISA assay for quantitative detection of human CD30, using the "Human sCD30 ELISA Kit" (Invitrogen, cat. no. BMS240), following the manufacturer's instructions.

Results

FIG. 24A shows the concentration of sCD30 in the cell culture supernatant. As shown, varying concentrations of sCD30 were detected in the cell culture supernatants from different cell lines. FIG. 24B shows that the concentration of sCD30 in the cell culture supernatants significantly correlated with CD30 membrane expression levels, as measured by quantitative flow cytometry as described previously in example 2 (Human IgG Calibrator kit, Biocytex, cat no. CP010).

To evaluate whether sCD30 can block potent BsG1-huCD3-FEALxCD30-MDX060-FERR-induced T-cell mediated cytotoxicity, T-cell mediated cytotoxicity by BsG1-huCD3-FEALxCD30-MDX060-FERR was assessed in DEL tumor cells (ALCL), which showed high levels of sCD30 in the supernatant (129 ng/mL). The T-cell mediated cytotoxicity assay was performed as described previously (example 8). FIG. 24C shows that BsG1-huCD3-FEALxCD30-MDX060-FERR induced potent T-cell mediated cytotoxicity in this cell line, with maximum tumor cell kill of 86% indicating that BsG1-huCD3-FEALxCD30-MDX060-FERR was still able to induce potent T-cell-mediated cytotoxicity in vitro in the presence of sCD30.

Thus, sCD30 concentrations varied between cell types, and correlated with the level of CD30 expression on the cell surface. Furthermore, BsG1-huCD3-FEALxCD30-MDX060-FERR was still able to induce potent T-cell mediated cytotoxicity in vitro in the presence of sCD30.

Example 16—Ex Vivo Cytotoxicity of bsG1-huCD3-FEALxCD30-MDX060-FERR Using Patient-Derived Peripheral Blood Mononuclear T Cells as Effector Cells CD3xCD30 bispecific antibodies were tested in an ex vivo cytotoxicity assay using a CD30-positive tumor cell line as target cells and primary patient-derived T cells as effector cells. As a source of T cells, Hodgkin lymphoma (HL), non-Hodgkin lymphoma (NHL) and acute myeloid leukemia (AML) patient-derived peripheral blood mononuclear cells (PBMCs, Discovery Life Sciences, Table 11) were used to evaluate CD3-dependent tumor cell kill.

L-428 tumor cells were labeled with Celltrace FarRed (Invitrogen, cat. no. C34564A; final concentration 2 μM) for 15 min at 37° C. After labeling, 5×the volume of ice cold DBSI was and incubated for 5 minutes at RT. Cells were pelleted, resuspended in medium, and tumor cells were seeded into 96-well plates (Greiner-bio-one, The Netherlands, cat. no. 655180) at a density of 50,000 cells/well. Serial dilutions of bsG1-huCD3-FEALxCD30-MDX060-FERR and control antibody IgG1-b12-FEAL were added (final concentration ranging from 1,000 to 0.051 ng/mL; 3-fold dilutions) and plates were incubated for 15 min at RT. PBMCs were thawed, counted and resuspended in medium (RPMI1640/10% FBS/1% penicillin-streptomycin/1% glutamate), before adding to tumor cells at an effector to target (E:T) ratio of 8:1 and plates were incubated for 72 hours at 37° C. After washing 2 times with PBS/0.1% BSA/0.02% azide (staining buffer), cells were stained to distinguish different cell populations using CD3 (T cells; Invitrogen, cat. no. 48-0037), CD14 (monocytes/macrophages; Biolegend; cat. no. 301834), CD19 (B cells; Biolegend; cat. no. 302246), CD16 (monocytes/macrophages; BD Biosciences; cat. no. 556618), CD56 (NK cells; BD Biosciences; cat. no. 564849) and CD66b (granulocytes; Biolegend; cat. no. 305116). Cells were additionally stained for T cell markers CD4 (1:50; Biolegend, cat. no. 300521, conjugated to Pacific Blue), CD8 (1:100; BD Biosciences, cat. no. 345772, conjugated to FITC) and T cell activation markers CD69 (1:50; Biolegend, cat. no. 310934, conjugated to BV650), CD25 (1:100; Invitrogen, cat. no. 25-0259-42, conjugated to PE-Cy7) and CD279/PD1 (1:50; Biolegend, cat. no. 329930, conjugated to BV605). Single stained samples with Ultracomp beads (5 μL; Invitrogen, cat. no. 01-2222-42) were included and used for compensation adjustments of the flow cytometer. After 30 min of incubation at 4° C., plates were washed twice with staining buffer, and cells were stained with 7-AAD (diluted 1:100 in staining buffer) for 10 min at 4° C. Cells were analyzed using a FACS Celesta (BD Biosciences) and data were processed using FlowJo (BD Biosciences). Dose-response curves were generated using non-linear regression analysis (sigmoidal dose-response with variable slope) using GraphPad Prism V7.02 software (GraphPad Software, San Diego, CA, USA).

The percentage of live target cells was calculated using the following equation:% live target cells=(absolute number of live, single Celltrace FarRed-labeled cells in each condition/absolute number of live, single Celltrace FarRed labeled cells in the condition containing only target cells and T cells without adding any antibodies)×100.

Results

FIG. 25A shows that bsG1-huCD3-FEALxCD30-MDX060-FERR induced dose-dependent cytotoxicity of L-428 tumor cells after 72 h, mediated by T cells derived from both a healthy control donor and different HL and NHL patient donors. Cytotoxicity was associated with T-cell activation and proliferation, illustrated by upregulation of CD69, CD25 and PD-1 (FIG. 25 B-D). No T-cell mediated cytotoxicity was observed for control antibody IgG1-b12-FEAL. No T-cell mediated cytotoxicity of L-428 tumor cells was observed for donor E (AML), which could be attributed to the low frequency of T cells within the PBMC sample (Table 11).

Together, these data illustrate that peripheral blood T cells from HL and NHL patients are capable of inducing T-cell mediated cytotoxicity of tumor cell lines in the presence of bsG1-huCD3-FEALxCD30-MDX060-FERR.

TABLE 11

Primary patient PBMC sample characteristics.

| Sample # | Code | Origin | Treatment (Tx) status | Company | Cell viability (%) | Frequency of T cells (%) |
|---|---|---|---|---|---|---|
| A | 100000537 | Hodgkin, Nodular Sclerosis Hodgkin Lymphoma | stage IV, pre-Tx | Discovery Life Sciences | 63.5 | 71.1 |
| B | 120328910 | Hodgkin lymphoma | pre-Tx | | 81.7 | 56.1 |
| C | 17A0D69A3 | Hodgkin, Mixed Cellularity Hodgkin Lymphoma | pre-Tx | | 87.5 | 35.6 |
| D | D4931CBAB | Hodgkin, Nodular Lymphocyte Predominance Hodgkin Lymphoma | stage II-A, pre-Tx, CD20+ | | 63.95 | 59.9 |

TABLE 11-continued

Primary patient PBMC sample characteristics.

| Sample # | Code | Origin | Treatment (Tx) status | Company | Cell viability (%) | Frequency of T cells (%) |
|---|---|---|---|---|---|---|
| E | 200003963 | Acute Myeloid Leukemia (AML) | active-Tx, EBV tested | | 65.55 | 17.4 |
| F | 121426858 | NHL, Peripheral T-Cell Lymphoma (PTCL) - Unspecified | stage III, post_Tx, treatment CHP + Adcetris/Adriamycin | | 66.2 | 68 |
| HC | | Healthy control PBMCs | N.A. | Sanquin | 86.55 | 48.4 |

Example 17—Evaluation of Pharmacokinetic Properties of BsG1-huCD3-FEAL×CD30-MDX060-FERR in SCID Mice 11-12 weeks old, female tumor-free SCID mice (C.B-17/IcrHan®Hsd-Prkdcscid mice, Envigo) (3 mice per group) were injected intravenously (IV) injected with a single dose of 1 µg (0.05 mg/kg) 10 µg (0.5 mg/kg) or 100 µg (5 mg/kg) of BsG1-huCD3-FEAL×CD30-MDX060-FERR. The experiment was set up to study antibody clearance in absence of target-mediated clearance, as BsG1-huCD3-FEAL×CD30-MDX060-FERR does not cross-react with mouse proteins.

40 µL blood samples were collected from the via cheek vena puncture or vena saphena puncture at 10 minutes, 4-6 hours, 24 hours, 2 days, 7 days, 14 days and 21 days after antibody administration. Blood was collected into K2-EDTA containing vials (Sarstedt, Microvette CB300, cat. No. 16.444.100) and centrifuged for 10 minutes at 10,000 g. Plasma supernatants were transferred to labeled Eppendorf vials and stored at −80° C. until plasma IgG concentration determination.

Human IgG concentrations were determined using a total human IgG enzyme-linked immunosorbent assay (ELISA). Mouse anti-human IgG-kappa clone MH16 (CLB Sanquin, The Netherlands; cat. no. M1268), coated in 100 µL PBS (BioTrading, cat. no. K654F500PP) overnight at 4° C. to 96-well Microlon ELISA plates (Greiner, Germany) at a concentration of 2 µg/mL, was used as capturing antibody. After blocking plates with PBSA (PBS with 0.2% bovine serum albumin [BSA]) for 1 hour at room temperature (RT), samples were added, serially diluted in PBSA, and incubated on a plate shaker for 1 hour at RT. Plates were washed three times with 300 µL PBST (PBS supplemented with 0.05% Tween 20) and subsequently incubated for 1 hour at RT with goat anti-human IgG immunoglobulin (Jackson, West Grace, PA; cat. no. 109-035-098; 1:10.000 in PBST supplemented with 0.2% BSA). Plates were washed three times with 300 µL PBST before incubation with 2,2'-azino-bis (3-ethylbenzthiazoline-6-sulfonic acid) (ABTS; Roche, cat. no. 11112422001 and 11112597001) protected from light. The reaction was stopped by adding 100 µL 2% oxalic acid (Sigma-Aldrich, cat. no. 33506), incubated for 10 min at RT. Absorbance was measured at 405 nm on an ELx808 Absorbance microplate reader (Biotek, Winooski, VT).

From the reference antibody human IgG1A (pure protein 30C, cat. No. BP078) a standard curve was generated (concentration range: 1 mg/mL [3 µL]) to be further diluted in 3-fold dilutions in PBSTA. The injected material was used to generate a second standard curve and was prepared from the 5 mg/kg dose with a concentration of 1 mg/mL (3.6 µL of antibody) to be further diluted in 3-fold dilutions in PBSTA.

Results

From the reference standards a calibration curve was calculated by interpolation of unknowns using a 4-parameter logistic fit curve in Microsoft Excel. Human IgG1 concentrations in the plasma samples were calculated from the equation of the calibration curve, plotted (FIG. 26A), and the area under the curve (AUC) was calculated using GraphPad Prism software. IgG clearance until the last day of blood sampling (day 21) was determined by the formula D*1.000/AUC, in which D is the dose of injection (1 mg/kg) (FIG. 26B).

BsG1-huCD3-FEAL×CD30-MDX060-FERR does not cross-react with mouse proteins and pharmacokinetic properties would thus be expected to be comparable to other non-binding wild-type human IgG1 molecules. The expected human IgG plasma concentration for all dose groups was calculated to be approximately 100 µg/mL (~5 mg/kg), 10 µg/mL (~0.5 mg/kg) or 1 µg/mL (~0.05 mg/kg). For all time points, samples from animals treated with 0.05 mg/kg were not measurable.

The plasma clearance rate of BsG1-huCD3-FEAL× CD30-MDX060-FERR was comparable to the predicted plasma clearance rate of regular human IgG1. The mean maximum human IgG plasma concentration (Cmax) was comparable to the predicted Cmax of regular human IgG1.

Thus, the pharmacokinetic profile of BsG1-huCD3-FEAL×CD30-MDX060-FERR is comparable with that predicted for regular human IgG1 in non-tumor bearing SCID mice in absence of target binding.

Example 18—Evaluation of C1q Binding to BsG1-huCD3-FEAL×CD30-MDX060-FERR

The binding of complement protein C1q to membrane-bound BsG1-huCD3-FEAL×CD30-MDX060-FERR, or the parental antibodies from which BsG1-huCD3-FEAL× CD30-MDX060-FERR was generated, i.e., IgG1-huCD3-FEAL and IgG1-CD30-MDX060-FERR, was assessed using either CD3- or CD30-expressing cells.

A. C1q Binding to BsG1-huCD3-FEALxCD30-MDX060-FERR Bound to CD3-Expressing Cells Binding of complement protein C1q to CD3-bound BsG1-huCD3-FEALxCD30-MDX060-FERR and IgG1-huCD3-FEAL was tested using stimulated human CD8+ T-cells. IgG1-CD52-E430G was included as a positive control, which has VH and VL domains based on the CD52 antibody CAMPATH-1H and has an Fc-enhanced backbone that is known to efficiently bind C1q when bound to the cell surface. As non-binding negative control antibodies, IgG1-b12-FERR and IgG1-b12 were included.

Human CD8+ T cells were purified (enriched) from buffy coats obtained from healthy volunteers (Sanquin) by negative selection using the RosetteSep™ Human CD8+ T Cell Enrichment Cocktail (Stemcell Technologies, cat. No. 15023C.2) according to the manufacturer's instructions. Purified T cells were resuspended in T-cell medium (Roswell Park Memorial Institute [RPMI]-1640 medium with 25 mM HEPES and L-glutamine (Lonza, cat. No. BE12-115F), supplemented with 10% heat-inactivated donor bovine serum with iron (DBSI; Gibco, cat. No. 20731-030) and penicillin/streptomycin (pen/strep; Lonza, cat. No. DE17-603E).

Anti-CD3/CD28 beads (Dynabeads™ Human T-Activator CD3/CD28; ThermoFisher Scientific, cat. No. 11132D) were washed with PBS and resuspended in T-cell medium. The beads were added to the enriched human CD8+ T cells at a 1:1 ratio and incubated at 37° C., 5% $CO_2$ for 48 h. Next, the beads were removed using a magnet, and the cells were washed twice in PBS and counted again.

Binding of BsG1-huCD3-FEALxCD30-MDX060-FERR and IgG1-huCD3-FEAL to the activated CD8+ T cells was confirmed by flow cytometry, using BsG1-huCD3-FEALxCD30-MDX060-FERR and IgG1-huCD3-FEAL (30 μg/mL), and R-phycoerythrin (PE)-conjugated goat-anti-human IgG F(ab')$_2$ (diluted 1:200 in GMB FACS buffer; Jackson ImmunoResearch, cat. no. 109-116-098).

Activated CD8+ T cells were seeded in a round-bottom 96-well plate (30,000 cells/well), pelleted, and resuspended in 30 μL assay medium (RPMI-1640 with 25 mM HEPES and L-glutamine, supplemented with 0.1% [w/v] bovine serum albumin fraction V (BSA; Roche, cat. no. 10735086001) and penicillin/streptomycin). Subsequently, 50 μL of BsG1-huCD3-FEALxCD30-MDX060-FERR, IgG1-huCD3-FEAL, IgG1-b12-FERR, IgG1-CD52-E430G, or IgG1-b12 (final concentrations of $1.7 \times 10^{-4}$-30 μg/mL in 3-fold dilution steps in assay medium) was added to each of the wells and incubated at 37° C. for 15 min to allow the antibodies to bind to the cells.

Human serum (20 μL/well; Sanquin, lot 20L15-02), as a source of C1q, was added to a final concentration of 20%. Cells were incubated on ice for 45 min, followed by two washes with cold GMB FACS buffer and incubation with 50 μL fluorescein isothiocyanate (FITC)-conjugated rabbit anti-human C1q (final concentration of 20 μg/mL (DAKO, cat no. F0254); diluted 1:75 in GMB FACS buffer) in the presence or absence of allophycocyanin-conjugated mouse-anti-CD8 (BD Biosciences, cat. no. 555369; diluted 1:50 in GMB FACS buffer) in the dark at 4° C. for 30 min. Cells were washed twice with cold GMB FACS buffer, resuspended in 20 μL of GMB FACS buffer supplemented with 2 mM ethylenediaminetetraacetic acid (EDTA; Sigma-Aldrich, cat. no. 03690) and 4',6-diamidino-2-phenylindole (DAPI) viability dye (1:5,000; BD Pharmingen, cat. no. 564907). C1q binding to viable cells (as identified by DAPI exclusion) was analyzed by flow cytometry on an iQue3 Screener (Intellicyt Corporation). Data were analyzed using iQue software (Intellicyt Corporation, ForeCyt® Enterprise Client Edition 6.2 [R3], Version 6.2.652). Binding curves were analyzed using non-linear regression analysis (sigmoidal dose-response with variable slope) using GraphPad Prism software.

Results

FIG. 27A shows that whereas dose-dependent C1q binding was observed to membrane-bound IgG1-CD52-E430G, no C1q binding was observed to membrane-bound BsG1-huCD3-FEALxCD30-MDX060-FERR or IgG1-huCD3-FEAL, or to the non-binding control antibodies.

B. C1q Binding to BsG1-huCD3-FEALxCD30-MDX060-FERR Bound to CD30-Expressing Cells Binding of complement protein C1q to CD30-bound BsG1-huCD3-FEALxCD30-MDX060-FERR and IgG1-huCD30-MDX060-FERR was tested using NCEB-1 mantle cell lymphoma cells. As a positive control, IgG1-7D8-E430G (anti-CD20) was included, which does not contain the inertness mutations and retains the capacity of binding to C1q. As non-binding negative control antibodies, IgG1-b12-FERR was included.

NCEB-1 cells were suspended at a concentration of $2 \times 10^6$ cells/mL in assay medium (RPMI-1640 (Lonza, Switzerland, cat. no. BE12-115F) containing 0.1% bovine serum albumin (BSA, fraction V, Roche, cat. no. 10735086001) and 1% penicillin/streptomycin (Gibco, cat. no. 15140-122). Tumor cells (100,000 cells in 50 μL) were added to 96-wells round bottom plates (Greiner Bio, cat no. 650180,). Next, 30 μL of BsG1-huCD3-FEALxCD30-MDX060-FERR, IgG1-CD30-MDX060-FERR, or control antibodies (final concentrations of 5.6×10-5-10 μg/mL in 3-fold dilution steps diluted in assay medium) is added to each of the wells and incubated at 37° C. for 15 min to allow the antibodies to bind to the cells.

Half of the cells (40 μL of cell suspension, containing antibodies) were plated in a different plate for checking the antibody binding. Binding of BsG1-huCD3-FEALxCD30-MDX060-FERR and IgG1-CD30-MDX060-FERR to NCEB-1 cells was confirmed by flow cytometry, using R-phycoerythrin (PE)-conjugated goat-anti-human IgG F(ab')2 (diluted 1:500 in FACS buffer; Jackson ImmunoResearch, cat. no. 109-116-098).

Human serum (10 μL/well; Sanquin, lot 21K04-01) was added to the remaining 40 μL of cell suspension (20% of final concentration) and incubated on ice for 45 min, followed by washing with FACS buffer and incubation with 25 μL FITC-conjugated rabbit anti-C1q antibodies (final concentration of 20 μg/mL (DAKO, cat no. F0254); diluted in FACS buffer) in the dark at 4° C. for 30 min. Cells were washed with cold FACS buffer, resuspended in 30 μL of FACS buffer—supplemented with TO-PRO™-3 viability stain (1:5000; ThermoFisher, cat. no. T3605) and measured on the iQue3 Screener (Intellicyt Corporation). Data were analyzed using iQue software (Intellicyt Corporation, ForeCyt® Enterprise Client Edition 6.2 [R3], Version 6.2.652). Binding curves were analyzed using non-linear regression analysis (sigmoidal dose-response with variable slope) using GraphPad Prism software.

Results

FIG. 27B shows that while dose-dependent C1q binding was observed to membrane-bound IgG1-CD20-E430G, no C1q binding was observed to membrane-bound BsG1-huCD3-FEALxCD30-MDX060-FERR or IgG1-CD30-MDX060-FERR, or to the non-binding control antibodies.

Thus, these results demonstrated that bsG1-huCD3-FEALxCD30-MDX060-FERR does not bind C1q, confirming the functionally inert backbone.

The invention claimed is:

1. A bispecific antibody comprising a CD30 binding region comprising a first heavy chain comprising the amino acid sequence of SEQ ID NO: 17 and a first light chain comprising the amino acid sequence of SEQ ID NO: 18, and a CD3 binding region comprising a second heavy chain comprising the amino acid sequence of SEQ ID NO: 19 and a second light chain comprising the amino acid sequence of SEQ ID NO: 20.

2. A nucleic acid construct, or a combination of nucleic acid constructs, encoding the bispecific antibody according to claim 1.

3. An expression vector, or a combination of expression vectors, comprising the nucleic acid construct(s) according to claim 2.

4. A delivery vehicle comprising the expression vector, or combination of expression vectors, according to claim 3.

5. A recombinant host cell capable of producing the bispecific antibody according to claim 1.

6. A method for producing a bispecific antibody comprising
   (i) culturing the recombinant host cell according to claim 5 under conditions wherein the antibody is produced, and
   (ii) isolating the produced bispecific antibody from the culture.

7. A pharmaceutical composition comprising the bispecific antibody according to claim 1 and a pharmaceutically-acceptable carrier.

8. A method of treating cancer comprising administering to a subject in need thereof an effective amount of the bispecific antibody according to claim 1.

9. The method according to claim 8, wherein the cancer is Hodgkin's lymphoma or Non-Hodgkin's lymphoma (NHL).

10. The method according to claim 9, wherein the Non-Hodgkin's lymphoma is T cell Non-Hodgkin's lymphoma (T-NHL).

11. The method according to claim 9, wherein the Hodgkin's lymphoma is classical Hodgkin's lymphoma (cHL).

12. The method according to claim 8, wherein the bispecific antibody is administered intravenously and/or subcutaneously.

13. The method according to claim 12, wherein the bispecific antibody is administered subcutaneously.

14. A method for producing a bispecific antibody comprising
   a) providing a first antibody comprising a CD30 binding region and a second antibody comprising a CD3 binding region, wherein both the CD30 binding region and CD3 binding region comprise the amino acid sequences described in claim 1,
      wherein the first and second antibodies comprise an Fc region, and
      wherein the amino acid sequences of the first and second CH3 regions of the first and second antibodies are different and are such that the heterodimeric interaction between the first and second CH3 regions is stronger than each of the homodimeric interactions of the first and second CH3 regions;
   b) incubating the first antibody together with the second antibody under reducing conditions sufficient to allow the cysteines in the hinge regions to undergo disulfide-bond isomerization; and
   c) obtaining the bispecific antibody comprising the first immunoglobulin heavy chain and the first immunoglobulin light chain of the first antibody and the second immunoglobulin heavy chain and the second immunoglobulin light chain of the second antibody.

15. A kit-of-parts comprising the bispecific antibody according to claim 1, and instructions for use.

16. A diagnostic composition comprising the bispecific antibody according to claim 1.

* * * * *